US008063270B2

(12) United States Patent
Jacquot et al.

(10) Patent No.: US 8,063,270 B2
(45) Date of Patent: Nov. 22, 2011

(54) METHODS FOR DETECTING ISOLATES OF THE POTATO VIRUS (PVY) RESPONSIBLE FOR NECROSES

(75) Inventors: Emmanuel Jacquot, Saint Peran (FR); Camille Kerlan, Breteil (FR); Valérie Balme, Marseilles (FR); Mathieu Rolland, Plouhinec (FR)

(73) Assignees: Institut National de la Recherche Agronomique, Paris (FR); Federation Nationale des Producteurs de Plants de Pomes de Terre, Paris (FR); Goupement National Interprofessionnel des Semences, Graines et Plants, Paris (FR)

(*) Notice: Subject to any disclaimer, the term of this patent is extended or adjusted under 35 U.S.C. 154(b) by 811 days.

(21) Appl. No.: 11/910,948

(22) PCT Filed: Mar. 31, 2006

(86) PCT No.: PCT/EP2006/061232
§ 371 (c)(1),
(2), (4) Date: Oct. 8, 2007

(87) PCT Pub. No.: WO2006/106082
PCT Pub. Date: Oct. 12, 2006

(65) Prior Publication Data
US 2008/0172766 A1    Jul. 17, 2008

(30) Foreign Application Priority Data
Apr. 8, 2005  (FR) .................................. 05 03519
Apr. 12, 2005  (FR) .................................. 05 03610

(51) Int. Cl.
*A01H 5/00* (2006.01)
(52) U.S. Cl. ..................................... 800/301; 800/317.2
(58) Field of Classification Search .................. None
See application file for complete search history.

(56) References Cited

U.S. PATENT DOCUMENTS
7,001,739 B2 * 2/2006 Mirkov et al. ............... 435/7.91

OTHER PUBLICATIONS

Balme-Sinibaldi, V., et al., "Characterization of Potato Virus Y (PVY) Molecular Determinanats Involved in Tobacco Vein Necrosis and Potato Tuber Necrosis," Giblot-Ducray Daniele: 12th EAPR Virology Section Meeting, 2004, Rennes, France. XP-002392026.
Bercks, R., "Methodische Untersuchungen über den serologischen Nachweis pflanzenpathogener Viren mit dem Bentonit-Flockunstest, dem Latex-Test and dem Bariumsulfat-Test," *Physopath. Z., Bd.*, vol. 58, pp. 1-17.
Blanco-Urgoiti, B., et al., "Characterization of potato potyvirus Y (PVY) isolates from seed potato batches. Situation of the NTN, Wilga and Z isolates," *European Journal of Plant Pathology*, 1998, vol. 104, pp. 811-819.
Boonham, N., et al., "Strain specific recombinant antibodies to potato virus Y potyvirus," *Journal of Virological Methods*, 1998, vol. 74, pp. 193-199.
Boonham, N., et al., "The detection of tuber necrotic isolates of *Potato virus Y*, and the accurate discrimination of $PVY^{\circ}$, $PVY^{N}$ and $PVY^{C}$ strains using RT-PCR," *Journal of Virological Methods*, 2002, vol. 102, pp. 103-112.
Brunt, A., et al., "Plant Viruses Online: Descriptions and Lists from the VIDE Database," Version 20th, 1996, http://biology.anu.edu.au/Groups/MES/vide/.
Chrzanowska, M., "New isolates of the necrotic strain of potato virus Y ($PVY^{N}$) found recently in Poland," *Potato Research*, 1991, vol. 34, pp. 179-182.
De Bokx, J.A., et al., "Potato virus Y," *Description of Plant Viruses*, 1981, vol. 242, CM1/AAB, Slough, England, 6 pp.
Dougherty, W., et al., "Expression and Function of Potyviral Gene Products," *Ann. Rev. Phytopathol.*, 1988, vol. 26, pp. 123-143.
Ellis, P., et al., "Production of monoclonal antibodies for detection and identification of strains of potato virus Y," *Canadian Journal of Plant Pathology*, 1996, vol. 18, pp. 64-70.
Fabre, F., et al., "Improvement of Barley *yellow dwarf virus*-PAV detection in single aphids using a fluorescent real time RT-PCR," *Journal of Virological Methods*, 2003, vol. 110, pp. 51-60.
Fakhfakh, H., et al., "Cell-free cloning and biolistic inoculation of an infectious cDNA of potato virus Y," *Journal of General Virology*, 1996, vol. 77, pp. 519-523.
Genbank Accession No. AF522296.1, "Potato virus Y strain N-Egypt, complete genome," 2004.
Glais, L., et al., "Molecular characterization of potato virus $Y^{N}$ isolates by PCR-RFLP: Differentiation of $PVY^{N}$ isolates by PCR-RFLP," 1996, vol. 102(7), pp. 655-662.
Glais, L., et al., "RFLP mapping of the whole genome of ten viral isolates representative of different biological groups of potato virus Y," *Arch Virol*, 1998, vol. 143, pp. 2077-2091.
Glais, L., et al., "Chapter 11—Variability and Evolution of *Potato Virus Potato Virus Y*, the Type Species of the *Potyvirus* Genus," *Plant Viruses As Molecular Pathogens*, 2001, pp. 225-253, Eds. Jawaid A. Khan and Jeanne Dijkstra, Food Products Press, The Haworth Press, Inc., New York.
Glais, L., et al., "Genomic variability in *Potato potyvirus Y* (PVY): evidence that $PVY^{N}W$ and $PVY^{NTN}$ variants are single to multiple recombinants between $PVY^{O}$ and $PVY^{N}$ isolates," *Arch Virol*, 2002, vol. 147, pp. 363-378.
Glais, L, et al., "$PVY^{N}$-605, The Reference $PVY^{N}$ Isolate, Displays a $PVY^{NTN}$ Non-Recombinant Genome," The 12th EAPR Virology Section Meeting, Rennes-France, 2004, abstracts, p. 50.
Glais, L., et al., "Specific detection of the $PVY^{N}$-W variant of *Potato virus Y*," *Journal of Virological Methods*, 2005, vol. 125, pp. 131-136.
Gugerli, P., "Characterization of Monoclonal Antibodies to Potato Virus Y and Their Use for Virus Detection," *J gen. Virol.*, 1983, vol. 64, pp. 2471-2477.
Heath, R, et al., "Biological Characterization of Six Australian Isolates of Potato Virus Y and their Serological Detection by ELISA," *Aust. J. Agric. Res.*, 1987, vol. 38, pp. 395-402.

(Continued)

*Primary Examiner* — Li Zheng
(74) *Attorney, Agent, or Firm* — Alston & Bird LLP

(57) ABSTRACT

The invention concerns a method for detecting the PVY virus which consists in a SNP test or an extension reaction specific to mutations corresponding to $R/K_{400}$ et $D/E_{419}$, the presence of at least one of said mutations inducting the presence of at least one virulent PVY strain capable of causing necrosis in plants of the Solanaceae family, in particular in potatoes.

34 Claims, 13 Drawing Sheets

OTHER PUBLICATIONS

Figure 2:
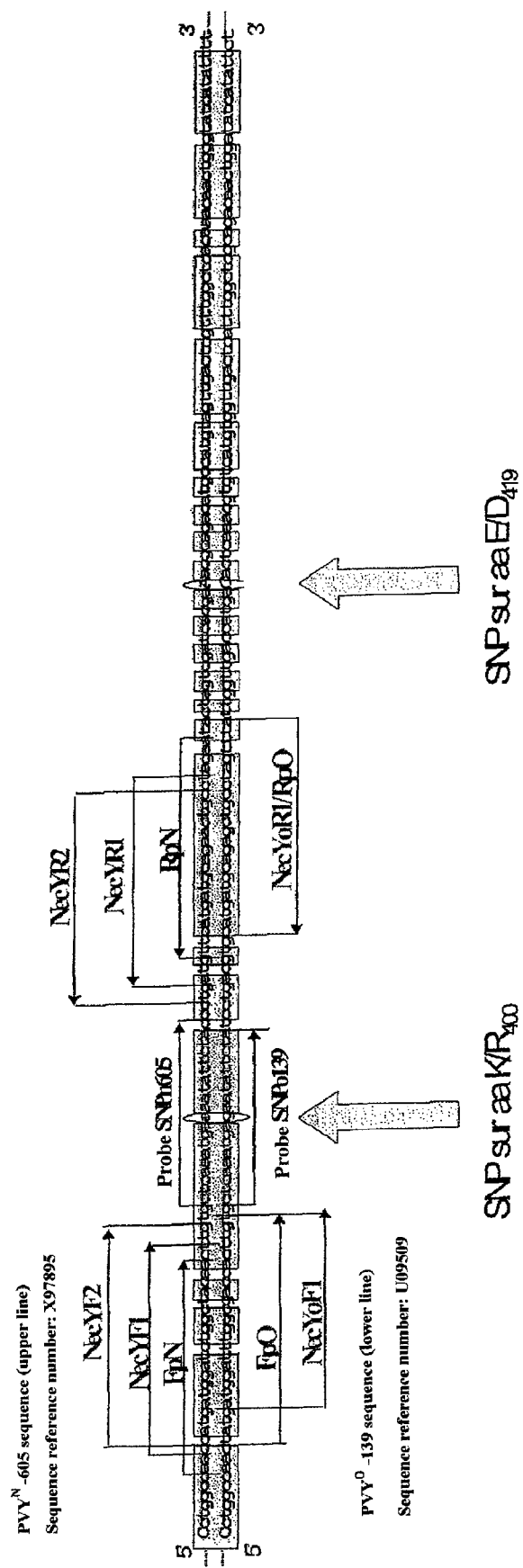

Jacquot, E., et al., "A single nucleotide polymorphism-based technique for specific detection and quantification of $Y^o$ and $Y^n$ isolates of *potato virus y (PVY)*," Phytopathologia Mediterranea & Joint Workshop on Molecular Diagnostics of Plant Pathogens, Lametia Terme, Catanzaro, Italy, 2003, XP001237410, pp. 198-299. Abstract Only.

Jacquot, E., et al., "A single nucleotide polymorphism-based technique for specific characterization of $Y^O$ and $Y^N$ isolates of Potato virus Y (PVY)," *Journal of Virological Methods*, 2005, vol. 125(1), pp. 83-93.

Jakab, G., et al., "Infectious in vivo and in vitro transcripts from a full-length cDNA clone of PVY-N605, a Swiss necrotic isolate of potato virus Y," *Journal of General Virology*, 1997, vol. 78, pp. 3141-3145.

Kerlan, C., et al., "Variability of Potato Virus Y in Potato Crops in France," *J. Phytopathology*, 1999, vol. 147, pp. 643-651.

Le Romancer, M., et al., "Biological characterisation of various geographical isolates of potato virus Y inducing superficial necrosis on potato tubers," *Plant Pathology*, 1994, vol. 43, pp. 138-144.

Maat, D., et al., "Serology," *Viruses of potatoes and seed-potato production*, 1987, Eds. Debokx, J.A. and van der Want, J.P.H., Pudoc Wageningen, NL.

Matoušek, J., et at, "Analysis of Variability of P1 Gene Region of N Strain of Potato Virus Y Using Temperature-Gradient Gel Electrophoresis and DNA Heteroduplex Analysis," *Acta virologica*, 2000, vol. 44, pp. 40-46.

McDonald, J., et al., "Properties of Strains of Potato Virus $Y^N$ in North America," *Plant Disease*, 1993, vol. 77(1), pp. 87-89.

McDonald, J., et al., "Host range, symptomatology, and serology of isolates of potato virus Y (PVY) that share properties with both the PVYN and PVYO strain groups," *American Potato Journal*, 1996, vol. 73(7), pp. 309-315. Abstract Only.

Milne, R.G., "The Plant Viruses-4," *The filamentous plant viruses*, 1988, Ed. R. G. Milne, Plenum Press New York & London.

Moravec, T., et al., "The detection of recombinant, tuber necrosing isolates of *Potato virus Y* ($PVY^{NTN}$) using a three-primer PCT based in the coat protein gene," *Journal of Virological Methods*, 2003, vol. 109, pp. 63-68.

Nie, X., et al., "A novel usage of random primers for multiplex RT-PCR detection of virus and viroid in aphids, leaves, and tubers," *Journal of Virological Methods*, 2001, vol. 91, pp. 37-49.

Nie, X., et al., "A new approach for the simultaneous differentiation of biological and geographical strains of *Potato virus Y* by uniplex and multiplex RT-PCR," *Journal of Virological Methods*, 2002, vol. 104, pp. 41-54.

Nie X., et al., "Specific differentiation of recombinant $PVY^{N:O}$ and $PVY^{NTN}$ isolates by multiplex RT-PCR," *Journal of Virological Methods*, 2003, vol. 113, pp. 69-77.

Oefner, Peter J., "Sequence variation and the biological function of genes: methodological and biological considerations," *Journal of Chromatography B*, 2002, vol. 782, pp. 3-25.

Ohshima, K., et al., "Production and application of monoclonal antibodies specific to ordinary strain and necrotic strain of potato virus Y," *Annals of the Phytopathological Society of Japan*, 1990, vol. 56(4), pp. 508-514. Abstract Only.

Ounouna, H., et al., "Production of monoclonal antibodies against synthetic peptides of the N-terminal region of *Potato virus Y* coat protein and their use in PVY strain differentiation," *Plant Pathology*, 2002, vol. 51, pp. 487-494.

Robaglia, C., et al., "Nucleotide Sequence of Potato Virus Y (N Strain) Genomic RNA," *J. gen. Virol.*, 1989, vol. 70, pp. 935-947.

Roberts, C, et al., " Real-time RT-PCR fluorescent detection of tomato spotted wilt virus," *Journal of Virological Methods*, 2000, vol. 88, pp. 1-8.

Rosner, A., et al., "Differentiating $PVY^{NTN}$ by unique single-restriction cleavage of PCR products," *Potato Research*, 1999, vol. 42, pp. 215-221.

Rosner, A., et al., "Differentiating $PVY^{NTN}$ from $PVY^N$ by annealing to reference RNA transcipts," *Journal of Virological Methods*, 2001, vol. 97, pp. 125-131.

Rosner, A., et al., "Tagging of viral RNA transcripts with strain-specific oligonucleotides: characterization and application," *Journal of Virological Methods*, 2003, vol. 110, pp. 105-109.

Sanz, A., et al., "Preparation of additional monoclonal antibodies for detection and discrimination of potato virus Y isolates infecting potato," *Potato Research*, 1990, vol. 33, pp. 365-375.

Shukla, D. et al., *The Potyviridae*, 1994, Cambridge University Press, Cambridge, 397 pp.

Sigvald, R., et al., "The relative efficiency of some aphid species as vectors of potato virus $Y^O$ ($PVY^O$)," *Potato Research*, 1984, vol. 27, pp. 285-290.

Singh, et al., "Selection of a monoclonal antibody to detect $PVY^N$ and its use in ELISA and DIBA assays," *Canadian Journal of Plant Pathology*, 1993, vol. 15, pp. 293-300.

Singh, et al., "Nucleotide sequence and genome organization of a Canadian isolate of the common strain of potato virus Y (PVYO)," *Canadian Journal of Plant Pathology-Revue Canadienne De Phytopathologie*, 1996, vol. 18(3), pp. 209-224. Abstract Only.

Smith, Kenneth M., "On the composite Nature of Certain Potato Virus Diseases of the Mosaic Group as Revealed by the use of Plant Indicators and Selective Methods of Transmission," *Proc. R. Soc. Land. B.*, 1931, vol. 109, pp. 251-267.

Szemes, M., et al., "Development of a multiplex AmpliDet RNA asay for simultaneous detection and typing of *potato virus Y* isolates," *Journal of Virological Methods*, 2002, vol. 100, pp. 83-96.

Talley, J., et al., "A simple kit for detection of plant viruses by the latex serological test," *Pl. Path.*, 1980, vol. 29, pp. 77-79.

Thole, V., et al., "Cloning and sequencing of potato virus Y (Hungarian isolate) genomic RNA," *Gene*, 1993, vol. 123, pp. 149-156. Abstract Only.

Tordo, V., et al., "Sequence polymorphism in the 5'NTR and in the P1 coding region of potato virus Y genomic RNA," *Journal of General Virology*, 1995, vol. 76, pp. 939-949.

Tribodet, M., et al., "Characterization of *Potato virus Y* (PVY) molecular determinants involved in the vein necrosis symptom induced by $PVY^N$ isolates in infected *Nicotiana tabacum* cv. Xanthi," *Journal of General Virology*, 2005, vol. 86, pp. 2101-2105.

Walkey, D., et al., "The Use of a Simple Electron-Microscope Serology Procedure to Observe Relationships of 7 Potyviruses," *Phytopathologische Zeitschrift-Journal of Phytopathology*, 1984, vol. 110(4), pp. 319-327. Abstract Only.

Walsh, K., et al., "Detection of different strains of *Potato virus Y* and their mixed infections using competitive fluorescent RT-PCR," *Journal of Virological Methods*, 2001, vol. 91, pp. 167-173.

\* cited by examiner codon polymorphism 738 (a2213 according to Jackab or a46 according to SEQ ID No 5)

```
PVY^N*  1   cctggccaaccatgatggatctggctacaacttgtgctcaaatgaaaatattctaccctg  60
            ||||||||||  |||||||||  ||||  ||  |||||||||||||||||  ||||||||||  ||||
PVY^O*  1   cctggccaactatgatggatttggcgaccacttgtgctcaaatgagaatattctatcctg  60
``` codon polymorphism 757 (a2271 according to Jackab or a104 according to SEQ ID No 5)

```
PVY^N   61  atgttcatgatgcagaactgcctagaatactagtcgatcacgaaacgcagacatgccatg  120
            |  ||  ||||||||||||  ||||||||  ||  |  ||  ||  ||  ||  ||  ||  ||  ||  ||||
PVY^O   61  acgtgcatgatgcagagctgcctagtttattggttgaccatgacactcaaacgtgtcatg  120
```

```
PVY^N  121  tagttgactcgtttggctcacaaacaactgggtatcatatt  161  (SEQ ID NO 5)
            |  |||||||||  |||||||||  ||  |||||||||  |||||||||
PVY^O  121  tggttgactcatttggctcgcagacaactggatatcatatt  161  (SEQ ID NO 6)
```

* sequences from PVY^N-605 and PVY^O-139 isolates

FIGURE 1

| | | Sample | | | |
|---|---|---|---|---|---|
| | | NTC | N-605 | O-139 | O/N mix |
| Primary fluorescence signal | FAM | 0.782+/-0.024 | 1.835+/-0.118 | 0.818+/-0.007 | 1.653;1.753 |
| | Vic | 0.424+/-0.008 | 0.464+/-0.026 | 1.277+/-0.040 | 1.198;1.117 |

PVY-N-K400-E419

$K_{400}$ 2168 cctggccaaccatgatggatctggctacaacttgtgctcaaatgaa[2213]aatattctaccctg 2227

$E_{419}$ 2228 atgttcatgatgcagaactgcctagaatactagtcgatcacgaa[2271]acgcagacatgccatg 2287

2288 tagttgactcgtttggctcacaaacaactgggtatcatatttt 2330 (SEQ ID No 14)

PVYo-R400-D419

$R_{400}$ 1 cctggccaactatgatggatttggcgaccacttgtgctcaaatgagaatattctatcctg 60

$D_{419}$ 61 acgtgcatgatgcagagctgcctagtttattggttgaccatgacactcaaacgtgtcatg 120

121 tggttgactcatttggctcgcagacaactggatatcatatt 161 (SEQ ID No 15)

PVY-NTPN-K400-D419

$K_{400}$ 2168 cctggccaaccatgatggatctggctacaacttgtgctcaaatgaa[2213]aatattctaccctg 2227

$D_{419}$ 2228 atgttcatgatgcagaactgcctagaatactagtcgatcacgac[2271]acgcagacatgccatg 2287

2288 tagttgactcgtttggctcacaaacaactgggtatcatatttt 2330 (SEQ ID No 16)

PVY-NTPN-R400-E419

$R_{400}$ 2168 cctggccaaccatgatggatctggctacaacttgtgctcaaatgag[2213]aatattctaccctg 2227

$E_{419}$ 2228 atgttcatgatgcagaactgcctagaatactagtcgatcacgaa[2271]acgcagacatgccatg 2287

2288 tagttgactcgtttggctcacaaacaactgggtatcatatttt 2330 (SEQ ID No 17)

PVY-NTPo-R400-E419

$R_{400}$ 1 cctggccaactatgatggatttggcgaccacttgtgctcaaatgagaatattctatcctg 60

$E_{419}$ 61 acgtgcatgatgcagagctgcctagtttattggttgaccatgaaactcaaacgtgtcatg 120

121 tggttgactcatttggctcgcagacaactggatatcatatt 161 (SEQ ID No 18)

PVY-NTPo-K400-D429

$K_{400}$ 1 cctggccaactatgatggatttggcgaccacttgtgctcaaatgaaaatattctatcctg 60

$D_{419}$ 61 acgtgcatgatgcagagctgcctagtttattggttgaccatgacactcaaacgtgtcatg 120

121 tggttgactcatttggctcgcagacaactggatatcatatt 161 (SEQ ID No 19)

FIGURE 6B

```
   1 aaattaaaac aactcaatac aacataagaa aatcaacgca aaaacactca caaaagcttt
  61 caactctaat tcaaacaatt tgttaagttt caatttcgat cttcatcaaa caaactcttt
 121 caatttcagt gtaagctatc gtaattcagt aagttatttc aaactctcgt aaattgcaga
 181 agatcatcca tggcaattta cacatcaaca atccagtttg gttccattga atgcaaactt
 241 ccatactcac ccgctccttt tgggctagtt gcggggaaac gagaagtttc aaccaccact
 301 gacccctttcg caagtttgga gatgcagctc agtgcgcgat tacgaaggca ggagtttgca
 361 actattcgaa catccaagaa tggtacttgc atgtatcgat acaagactga tgtccagatt
 421 gcgcgcattc aaaagaagcg cgaggaaaga gaaagagagg aatataattt ccaaatggct
 481 gcgtcaagtg ttgtgtcgaa gatcactatt gctggtggag agccaccttc aaaacttgaa
 541 tcacaagtgc ggaggggtgt catccacaca actccaagga tgcgcacagc aaaaacatat
 601 cacacgccaa agttgacaga gggacaaatg aaccaccttt tcaagcaggt gaagcaaatt
 661 atgtcaacca aggagggtc tgtccaactg attagcaaga aaagtaccca tgttcactat
 721 aaagaagttt tgggatcaca tcgcgcagtt gtttgcactg cacatatgag aggtttacga
 781 aagagagtgg actttcggtg tgataaatgg accgttgtgc gtctacagca tctcgccagg
 841 acggacaagt ggactaacca agttcgtgct actgatctac gcaagggcga tagtggagtt
 901 atattgagta atactaatct caaaggaaac tttgggagaa gctcggaggg cctattcata
 961 gtgcgtgggt cgcacgaagg aaaaatctat gatgcacgtt ccaaggttac tcaaggggtt
1021 atggattcaa tggttcagtt ctcaagcgct gaaagctttt ggaagggatt ggacggcaat
1081 tgggcacaaa tgagatatcc tacagatcat acatgtgtgg caggcttacc agttgaagac
1141 tgtggcagag ttgcagcgat aatgacacac agtattttac cgtgctataa gattacctgc
1201 cctacctgtg cccaacaata tgccaacttg ccagccagtg acttacttaa gatattacac
1261 aagcacgcaa gtgatggtct aaatcgattg ggggcagaca agatcgctt tgtgcatgtc
1321 aaaaagttct tgacaatctt agagcactta actgaaccgg ttgatctgag tctagaaatt
1381 ttcaatgaag tattcaagtc tataggggag aagcaacaat cacctttcaa aaacctgaat
1441 attctgaata atttctttt gaaaggaaag gaaaatacag ctcgtgaatg gcaggtggct
1501 caattaagct tacttgaatt ggcaagattc caaaagaaca gaacggataa tatcaagaaa
1561 ggagacatct cgttctttag gaataaacta tctgccaaag caaattggaa cttgtatctg
1621 tcatgtgata accagctgga taagaatgca agcttcctgt ggggacagag ggaatatcat
1681 gctaagcgat ttttctcgaa ctatttcgag gaaattgatc cagcgaaggg ctattcagca
1741 tacgaaaatc gtttgcatcc gaatgggaca agaaaacttg caattggaaa cctaattgta
1801 ccacttgatc tggctgagtt taggcggaag atgaaaggtg attataaaag acagccaggg
1861 gtgagtaaga agtgcacgag ctcgaaggat ggaaactacg tgtatccctg ttgttgcact
1921 acacttgatg atggctcagc tgttgaatca acatttttacc cgccaactaa gaagcacctc
1981 gtaataggta atagtggcga ccaaaagtat gttgacttac caaaagggaa ttctgagatg
2041 ttatatattg ccaggcaagg cttctgttac attaacattt cctcgcgat gttgattaac
2101 attagtgagg aagatgcaaa ggatttcact aagaaggttc gtgacatgtg tgtgccaaag
2161 cttggaacct ggccaaccat gatggatctg gctacaactt gtgctcaaat gaAaatattc
2221 taccctgatg ttcatgatgc agaactgcct agaatactag tcgatcacga Aacgcagaca
2281 tgccatgtag ttgactcgtt tggctcacaa acaactgggt atcatatttt gaaagcatct
2341 agcgtgtccc aacttatttt gtttgctaat gatgagttgg agtctgacat taagcactat
2401 agagttggtg gtattcctgg agcatgccct gagcttgggt ccacaatatc accttttaga
2461 gaaggaggaa tcataatgtc tgagtcagca gcgctaaaac tgctcctaaa gggaattttt
2521 aggcccaaag tgatgaagca attgctactg gatgaaccat atttgctcat ttatcgata
2581 ttatctcctg gtatacttat ggctatgtac aacaatggga tatttgagtt agcggtgaag
2641 ttgtggatca atgagaaaca atctatagcc atgatagcat cgttattgtc cgccttggct
2701 ttacgagtgt cagcagcaga aacactcgtt gcacagagga ttataattga cacggcagca
2761 acagatcttc tcgatgctac gtgtgatgga ttcaatttaa atctgacata tcccactgca
```

FIGURE 7A

MAIYTSTIQFGSIECKLPYSPAPFGLVAGKREVSTTTDPFASLEMQLSARLRRQEFATIRTSKNGTCMYRYKTDV
QIARIQKKREEREREEYNFQMAASSVVSKITIAGGEPPSKLESQVRRGVIHTTPRMRTAKTYHTPKLTEGQMNHL
IKQVKQIMSTKGGSVQLISKKSTHVHYKEVLGSHRAVVCTAHMRGLRKRVDFRCDKWTVVRLQHLARTDKWTNQV
RATDLRKGDSGVILSNTNLKGNFGRSSEGLFIVRGSHEGKIYDARSKVTQ

<u>GVMDSMVQFSSAESFWKGLDGNWAQMRYPTDHTCVAGLPVEDCGRVAAIMTHSILPCYKITCPTCAQQYANLPAS</u>
<u>DLLKILHKHASDGLNRLGADKDRFVHVKKFLTILEHLTEPVDLSLEIFNEVFKSIGEKQQSPFKNLNILNNEFLK</u>
<u>GKENTAREWQVAQLSLLELARFQKNRTDNIKKGDISFFRNKLSAKANWNLYLSCDNQLDKNASFLWGQREYHAKR</u>
<u>FFSNYFEEIDPAKGYSAYENRLHPNGTRKLAIGNLIVPLDLAEFRRKMKGDYKRQPGVSKKCTSSKDGNYVYPCC</u>
<u>CTTLDDGSAVESTFYPPTKKHLVIGNSGDQKYVDLPKGNSEMLYIARQGFCYINIFLAMLINISEEDAKDFTKKV</u>
<u>RDMCVPKLGTWPTMMDLATTCAQMK$_{400}$IFYPDVHDAELPRILVDHE$_{419}$TQTCHVVDSFGSQTTGYHILKASSVSQ</u>
<u>LILFANDELESDIKHYRVG</u>

GIPGACPELGSTISPFREGGIIMSESAALKLLLKGIFRPKVMKQLLLDEPYLLILSILSPGILMAMYNNGIFELA
VKLWINEKQSIAMIASLLSALALRVSAAETLVAQRIIIDTAATDLLDATCDGFNLNLTYPTALMVLQVVKNRNEC
DDTLFKAGFSHYNMSVVQIMEKNYLSLLGDAWKDLTWREKLSATWHSYKAKRSITQFIKPIGKADLKGLYNISPQ
AFLGQGVQRVKGTASGLNERLNNYINTKCVNISSFFIRRIFRRLPTFVTFINSLLVISMLTSVVAVCQAIILDQR
KYRKEIELMQIEKNEIVCMELYASLQRKLEREFTWDEYMEYLKSVNPQIVQFAQAQMEEYNVRHQRSTPGVKNLE
QVVAFITLIIMMFDAERSDCVFKTLNKFKGIVSSMDHEVKHQSLDDVIKNFDERNEVIDFELNEDTIKTSSVLDT
KFSDWWDRQIQMGHTLPHYRTEGHFMEFTRATAVQVANDIAHSEHLDFLVRGAVGSGKSTGLPVHLSAAGSVLLI
EPTRPLAENVFKQLSSEPFFKKPTLRMRGNSVFGSSPISIMTSGFALHYYANNRSQLTQFNFIIFDECHVLDPSA
MAFRSLLSVYHQTCKVLKVSATPVGREVEFTTQQPVKLVVEDTLSFQSFVDAQGSKTNADVVQHGSNILVYVSSY
NEVDTLAKLLTDRNMVVSKVDGRTMKHGCLEIVTKGTSAKPHFVVATNIIENGVTLDIDVVVDFGLKVSPFLDID
NRSIAYNKISVSYGERIQRLGRVGRFKKGVALRIGHTEKGIIEIPSMIASEAALACFAYNLPVMTGGVSTSLIGN
CTVRQVKTMQQFELSPFFIQNFVAHDGSMHPVIHDILKKYKLRDCMTPLCDQSIPYRASSTWLSVSEYERLGVVL
DIPKQIKIAFHIKDIPPKLHEMLWETVIKYKDVCLFPSIRASSISKIAYTLRTDLFAIPRTLILVERLIEEERVK
QSQFRSLIDEGCSSMFSIVNLTNTLRARYAKDYTAENIQKLEKVRSQLKEFSNLNGSACEENLMKRYESLQFVHH
QATTSLAKDLKLKGVWKKSLVVQDLLIAGAVAIGGIGLIYSWFTQSVETVSHQGKNKSKRIQALKFRHARDKRAG
FEIDNNDDTIEEFFGSAYRKKGKGKGTTVGMGKSSRRFVNMYGFDPTEYSFIQFVDPLTGAQIEENVYADIRDIQ
ERFSDVRKKMVEDDEIELQALGSNTTIHAYFRKDWSDKALKIDLMPHNPLKICDKSNGIAKFPERELELRQTGPA
IEVDVKDIPKQEVEHEAKSLMRGLRDFNPIAQTVCRVKVSVEYGTSEMYGFGFGAYIIVNHHLFKSFNGSMEVRS
MHGTFRVKNLHSLSVLPIKGRDIIIIKMPKDFPVFPQKLHFRAPVQNERICLVGTNFQEKHASSIITETSTTYNV
PGSTFWKHWIETNDGHCGLPVVSTADGCLVGIHSLANNVQTTNYYSAFDEDFESKYLRTNEHNEWTKSWVYNPDT
VLWGPLKLKESTPKGLFKTTKLVQDLIDHDVVVEQAKHSAWMYEALTGNLQAVATMKSQLVTKHVVKGECRHFKE
FLTVDSEAEAFFRPLMDAYGKSLLNREAYIKDIMKYSKPIDVGIVDCDAFEEAINRVIIYLQVHGFQKCNYITDE
QEIFKALNMKAAVGAMYGGKKKDYFEHFTEADKEEIVMQSCFRLYKGSLGIWNGSLKAELRCKEKILANKTRTFT
AAPLDTLLGGKVCVDDFNNQFYSKNIECCWTVGMTKFYGGWDKLLRRLPENWVYCDADGSQFDSSLTPYLINAVL
IIRSTYMEDWDLGLQMLRNLYTEIIYTPISTPDGTIVKKFRGNNSGQPSTVVDNSLMVVLAMHYALIKECVEFEE
IDSTCVFFVNGDDLLIAVNPEKESILDRMSQHFSDLGLNYDFSSRTRRKEELWFMSHRGLLIEDMYVPKLEEERI
VSILQWDRADLPEHRLEAICAAMIESWGYFELTHQIRRFYSWLLQQQPFSTIAQEGKAPYIASMALKKLYMNRTV
DEEELKAFTEMMVALDDEFECDTYEVHHQGNDTIDAGGSTKKDAKQEQGSIQPNLNKEKEKDVNVGTSGTHTVPR
IKAITSKMKMPKSKGATVLNLEHLLEYAPQQIDISNTRATQSQFDTWYEAVQLAYDIGETEMPTVMNGLMVWCIE
NGTSPNINGVWVMMDGNEQVEYPLKPIVENAKPTLRQIMAHFSDVAEAYIEMRNKKEPYMPRYGLVRNLRDGSLA
RYAFDFYEVTSRTPVRAREAHIQMKAAALKSAQSRLFGLDGGISTQEENTERHTTEDVSPSMHTLLGVKNM

FIGURE 7B

```
   1 aattaaaaca actcaataca acataagaaa aacagcgcaa aaacactcat aaacgcttat
  61 tctcactcaa gcatcttgct aagtttcagt ttaaatcatt tccttgcaat tctcttaaac
 121 aatattggaa accatttcaa ctcaacaagc aatttcatca cttccaacca atttaaaatc
 181 ctcgatggca acttacatgt caacgatctg tttcggttcg tttgaatgca agctaccata
 241 ctcacccgcc tcttgcgggc ttattgtgaa ggaacgagaa gtgctggctt ccgttaatcc
 301 tttcgcagat ctggaaacac aacttagtgc acgattgctc aagcaagaat atgctactgt
 361 tcgtgtgctc aagaacggta cttttacgta tcgatacaag actgatgccc agataaagcg
 421 cattcagaag aaactggaga ggaaggatag ggaagaatat cacttccaaa tggccgctcc
 481 tagtattgtg tcaaaaatta ctatagctgg tggagatcct ccatcaaagt ctgagccaca
 541 agcaccaaga gggatcattc atacaactcc aagggtgcgt aaagtcaaga cacgccccat
 601 aataaagttg acagaaggcc agatgaatca tttcattaag caggtaaagc agattatgtc
 661 ggagaagaga gggtctgtcc acttaattaa taagaagacc actcatgttc aatataagga
 721 gatacttggt gcatactccg ccacggttcg aactgcacat atgatgggtt tgcgacggag
 781 agtggacttc cgatgtgata tgtggacagt tggactttg caacgtctcg ctcggacgga
 841 caaatggtcc aatcaagtcc gcactatcaa catacgaagg ggtgatagtg gagtcatctt
 901 gaacacaaaa agcctcaaag gccactttgg tagaagttca ggagacttgt tcatagtgcg
 961 cggatcacat gaagggaaat tgtacgatgc acgttctaga gttactcaga gtgttttgga
1021 ctcaatgatc cagttttcga atgctgataa tttttggaag ggtctggacg gcaattgggc
1081 acgaatgaga tatccttcgg atcacacatg tgtagctggt ttacctgtcg aagattgtgg
1141 tagggttgct gcattgatgg cacacagtat cctccatgc tataagataa cctgcccac
1201 ctgtgctcaa cagtatgcca gcttgccggt tagcgatctg tttaagctgt tgcataaaca
1261 tgcaagagat ggtttgaacc gattgggagc agataaagac cggtttatac atgttaataa
1321 gttcttgata gcgttagagc atctaactga accggtggat ttgaatctcg agcttttcaa
1381 tgagatattt aaatccatag gggagaagca gcaagcaccg ttcaagaatt taaatgtctt
1441 gaataatttc ttcctgaaag gaaaagaaaa tacagctcat gaatggcagg tggctcaatt
1501 gagtttgctc gaattagcaa ggttccagaa gaatagaact gataacatca agaaaggtga
1561 tatatccttc ttcagaaata aattatttgc caaggcaaat tggaatctgt atttgtcgtg
1621 cgacaaccaa ttggacaaaa atgcaaattt cctgtgggga caagggagt atcatgctaa
1681 gcggttttc tcaaacttct tgaggaaat tgatccagca aagggatact cagcatatga
1741 aatccgcaag catccaagtg gaacaaggaa gctctcaatt ggtaacttag ttgtcccact
1801 tgatttagct gagtttaggc agaagatgaa aggtgactat aggaaacaac caggggtcag
1861 cagaaagtgc acgagttcga aagatggtaa ttatgtgtat ccctgttgtt gcacaacact
1921 tgatgatggt tcagccattg aatcaacatt ctatccacca actaaaaagc acttgtaat
1981 aggcaatagt ggtgaccaaa agtttgttga tttaccaaaa ggggattcag agatgttata
2041 cattgccaag cagggttatt gttatattaa cgtgtttctt gcaatgctaa ttaacattgg
2101 cgaggaggat gcaaaggatt tcacaaagaa agtccgcgac atgtgtgtgc cgaagcttgg
2161 aacctggcca actatgatgg atttggcgac cacttgtgct caaatgaGaa tattctatcc
2221 tgacgtgcat gatgcagagc tgcctagttt attggttgac catgaCactc aaacgtgtca
2281 tgtggttgac tcatttggct cgcagacaac tggatatcat attctaaaag catccagcgt
2341 gtctcaactt atcttgtttg caaatgatga attagaatct gatataaaac attatagagt
2401 tggtggcgtt cctaatgcat gccctgaact tgggtccacg atatcacctt ttagagaagg
2461 aggagttata atgtctgagt cggcagcgct gaaactgctt ttgaagggaa ttttagacc
2521 taaggtgatg agacagttgc tgttagatga gccttacctg ttgattctat caatattatc
2581 ccctggcata ctgatggcta tgtataataa tgggattttt gaacttgcgg taagattgtg
2641 gattaatgag aaacaatcca tagctatgat agcatcgcta ctatcagctt tagcctacg
2701 agtgtcagcg gcagaaacac tcgtcgcaca gagaattata attgatgctg cagctacaga
2761 cctccttgat gctacgtgtg atggattcaa cctacatcta acgtacccca ctgcattaat
```

FIGURE 8A

METISTQQAISSLPTNLKSSMATYMSTICFGSFECKLPYSPASCGLIVKEREVLASVNPFADLETQLSARLLKQE
YATVRVLKNGTFTYRYKTDAQIKRIQKKLERKDREEYHFQMAAPSIVSKITIAGGDPPSKSEPQAPRGIIHTTPR
VRKVKTRPIIKLTEGQMNHFIKQVKQIMSEKRGSVHLINKKTTHVQYKEILGAYSATVRTAHMMGLRRRVDFRCD
MWTVGLLQRLARTDKWSNQVRTINIRRGDSGVILNTKSLKGHFGRSSGDLFIVRGSHEGKLYDARSRVTQ

<u>SVLDSMIQFSNADNFWKGLDGNWARMRYPSDHTCVAGLPVEDCGRVAALMAHSILPCYKITCPTCAQQYASLPVS
DLFKLLHKHARDGLNRLGADKDRFIHVNKFLIALEHLTEPVDLNLELFNEIFKSIGEKQQAPFKNLNVLNNFFLK
GKENTAHEWQVAQLSLLELARFQKNRTDNIKKGDISFFRNKLFAKANWNLYLSCDNQLDKNANFLWGQREYHAKR
FFSNFFEEIDPAKGYSAYEIRKHPSGTRKLSIGNLVVPLDLAEFRQKMKGDYRKQPGVSRKCTSSKDGNYVYPCC
CTTLDDDGSAIESTFYPPTKKHLVIGNSGDQKFVDLPKGDSEMLYIAKQGYCYINVFLAMLINIGEEDAKDFTKKV
RDMCVPKLGTWPTMMDLATTCAQMR$_{400}$IFYPDVHDAELPSLLVDHD$^{429}$TQTCHVVDSFGSQTTGYHILKASSVSQ
LILFANDELESDIKHYRVG</u>

GVPNACPELGSTISPFREGGVIMSESAALKLLLKGIFRPKVMRQLLLDEPYLLILSILSPGILMAMYNNGIFELA
VRLWINEKQSIAMIASLLSALALRVSAAETLVAQRIIIDAAATDLLDATCDGFNLHLTYPTALMVLQVVKNRNEC
DDTLFKAGFPSYNTSVVQIMEKNYLSLLDDAWKDLTWREKLSATWYSYRAKRSITRYIKPTGRADLKGLYNISPQ
AFLGRSAQVVKGTASGLSERFNNYFNTKCVNISSFFIRRIFRRLPTFVTFVNSLLVISMLTSVVAVCQAIILDQR
KYRREIELMQIEKNEIVCMELYASLQRKLERDFTWDEYIEYLKSVNPQIVQFAQAQMEEYDVRHQRSTPGVKNLE
QEVAFMALVIMVFDAERSDCVFKTLNKFKGVLSSLDHEVRHQSLDDVIKNFDERNEIIDFELSEDTIRTSSVLDT
KFSDWWDRQIQMGHTLPHYRTEGHFMEFTRATAVQVANDIAHSEHLDFLVRGAVGSGKSTGLPVHLSVAGSVLLI
EPTRPLAENVFKQLSSEPFFKKPTLRMRGNSIFGSSPISVMTSGFALHYFANNRSQLAQFNFVIFDECHVLDPSA
MAFRSLLSVYHQACKVLKVSATPVGREVEFTTQQPVKLIVEDTLSFQSFVDAQGSKTNADVVQFGSNVLVYVSSY
NEVDTLAKLLTDKNMMVTKVDGRTMKHGCLEIVTKGTSARPHFVVATNIIENGVTLDIDVVVDFGLKVSPFLDID
NRSIAYNKESVSYGERIQRLGRVGRFKKGVALRIGHTEKGIIEIPSMVATEAALACFAYNLPVMTGGVSTSLIGN
CTVRQVKTMQQFELSPFFIQNFVAHDGSMHPVIHDILKKYKLRDCMTPLCDQSIPYRASCTWLSVSEYERLGVAL
EIPKQIKIAFHIKEIPPKLHEMLWETVVKYKDVCLFPSIRASSISKIAYTLRTDLFAIPRTLILVERLLEEERVK
QSQFRSLIDEGCSSMFSIVNLTNTLRARYAKDYTAENIQKLEKVRSQLKEFSNLDGSACEENLIKRYESLQFVHH
QAATSLAKDLKLKGTWKKSLVAKDLIIAGAVAIGGIGLIYSWFTQSVETVSHQGKNKSKRIQALKFRHARDKRAG
FEIDNNDDTIEEFFGSAYRKKGKGKGTTVGMGKSSRKFINMYGFDPTEYSFIQFVDPLTGAQIEENVYADIRDIQ
DRFSEVRKKMVENDDIEMQALGSNTTIHAYFRKDWSDKALKIDLMPHNPLKVCDKTNGIAKFPERELELRQTGPA
VEVNVKDIPAQEVEHEAKSLMRGLRDFNPIAQTVCRLKVSVEYGTSEMYGFGFGAYIIANHHLFRSYNGSMEVQS
MHGTFRVKNLHSLSVLPIKGRDIILIKMPKDFPVFPQKLHFRAPIQNERVCLVGTNFQEKYASSIITETSTTYNI
PGSTFWKHWIETDNGHCGLPVVSTADGCLVGIHSLANNAHTTNYYSAFDEDFESKYLRANEHNEWVKSWKYNPDT
VLWGFLKLKDSTPKGLFKTTKLVQDLIEHDVVVEQAKHSAWMFEALTGNLQAVATMKSQLVTKHVVKGECRHFKE
FLTVDAEAEAFFRPLMDAYGKSLLNRDAYIKDIMKYSKPIDVGIVDCDAFEEAINRVIIYLQVHGFKKCAYVTDE
QEIFKALNMKAAVGAMYGGKKKDYFEHFTDADKEEIVMQSCLRLYKGLLGIWNGSLKAELRCKEKILANKTRTFT
AAPLDTLLGGKVCVDDFNNQFYSKNIECCWTVGMTKFYGGWDKLLRRLPENWVYCDADGSQFDSSLTPYLFNAVL
TIRSTYMEDWDVGLQMLRNLYTEIVYTPISTPDGTIVKKFRGNNSGQPSTVVDNSLMVVLAMHYAFIREGIEFEE
TDSTCVFFVNGDDLLIAVNPDKEDILDRLSQHFSDLGLNYDFSSRTRNKEELWFMSHRGLLIEGMYVPKLEEERI
VSILQWDRADLAEHRLEAICARMIESWGYSELTHQIRRFYSWLLQQQPFATIAQEGKAPYIASMALRKLYMDRAV
DEEELRAFTEMMVALDDEFEFDSYEVYHQANDTIDAGGSNKKDTKPEQSSIQSNPNKGKDKDVNAGTSGTHTVPR
IKAITSKMRMPKSKGAAVLNLEHLLEYAPQQIDISNTRATQSQFDTWYEAVRMAYDIGETEMPTVMNGLMVWCIE
NGTSPNVNGVWVMMDGNEQVEYPLKPIVENAKPTLRQIMAHFSDVAEAYIEMRNKKEPYMPRYGLIRNLRDMGLA
RYAFDFYEVTSRTPVRAREAQIQMKAAALKSAQPRLFGLDGGISTQEENTERHTTEDVSPSMHTLLGVKNM

FIGURE 8B

METHODS FOR DETECTING ISOLATES OF THE POTATO VIRUS (PVY) RESPONSIBLE FOR NECROSES

The present invention relates to a method for detecting potato virus PVY comprised of a SNP test or an extension reaction specific for the mutations corresponding to $R/K_{400}$ and $D/E_{419}$, the presence of at least one said mutations being an indication of the presence of a virulent strain of PVY capable of causing necrosis in plants of the Solanaceae family, the potato in particular.

Potato virus Y (PVY), after which the potyvirus group is named, is one of most important plant pathogens from an economic point of view (Milne, 1988; Shukla et al., 1994). First reported in the 1930's in the potato (Smith, 1931), PVY is now distributed throughout the world on a number of different hosts. The virus is transmitted by aphids in a non-persistent manner (Sigvald, 1984) and infects several species of crop plants belonging to the Solanaceae family (De Bokx and Hutting a, 1981; Brunt et al., 1996).

The viral genome consists of a single-stranded positive-sense RNA molecule approximately 10 kb in length, with a VPg protein covalently bound at its 5' end and a poly-A tail at its 3' end. The viral RNA codes for a polyprotein subsequently cleaved into nine products by three proteases coded by the virus (Dougherty and Carrington, 1988). Depending on the host from which they were initially collected, the PVY isolates were categorized into four different strains, potato, pepper, tobacco and tomato. Within the potato strain, the isolates were characterized on the basis of their biological properties (symptoms and responses to various sources of resistance). This characterization led to the definition of various virus groups. Thus, three groups of potato strains, $PVY^N$, $PVY^O$ and $PVY^C$ (De Bokx and Hutting a, 1981) were identified. These groups are defined by the systemic or local character of the symptoms induced on *Nicotiana tabacum* and *Solanum tuberosum*.

The isolates belonging to the $PVY^N$ group induce brown spot disease on the leaves of *N. tabacum* cv. *Xanthi* and a very light mottling, with only rarely necrotic leaves in the potato. $PVY^O$ isolates induce only symptoms of mottling and mosaic on tobacco and a light to serious mosaic and leaf drop in the potato. Finally, $PVY^C$ isolates induce symptoms of necrotic streaking in certain potato cultivars.

$PVY^N$ and $PVY^O$ isolates are responsible for high-yield losses, up to 40% to 70% in the case of the potato. Thus, the efficient detection and identification of necrotic and non-necrotic PVY isolates in potato crops are a major problem for producers.

The characterization of PVY "potato" isolates first relied on biological tests. However, such an approach requires both time and space and is not easily adaptable for a rapid diagnosis or for a large-scale test.

Next, to meet the need for a reliable and rapid test, double- or triple-antibody sandwich enzyme-linked immunosorbent assays (DAS- or TAS-ELISA) using polyclonal and/or monoclonal antibodies (Gugerli and Fries, 1983; Matt and Hutting a, 1987; Oshima et al., 1990; Sanz et al., 1990; Singh et al., 1993; Ellis et al., 1996) and an approach by immunoelectron microscopy (Walkey and Webb, 1984) and by agglutination with latex (Berckx, 1967; Tallay et al., 1980) were developed.

Nevertheless, none of these tests proves able to distinguish the isolates capable and incapable of inducing necrosis (Mac Donald and Singh, 1996; Boonham and Barker, 1998; Ounouna, 2002).

Indeed, the recent emergence of new variants of $PVY^N$ including tubular ring necrosis $PVY^{NTN}$ (Le Romancer et al., 1994; Kerlan et al., 1999) and $PVY^N$-W isolates (Chrzanowska, 1991) highlights the limits of the serological tools available. Indeed, PVY-specific monoclonal and/or polyclonal antibodies place $PVY^N$-W isolates in the $PVY^O$ group. Moreover, serological tools are not able to make the distinction between $PVY^{NTN}$ and $PVY^N$ isolates.

Four complete sequences of $PVY^N$ (Robaglia et al., 1989; Jakab et al., 1997; Abdelmaksoud and Gamal Eldin, 2002; Deny and Singh, 2003), two complete sequences of $PVY^{NTN}$ (Thole et al., 1993; Deny and Singh, 2003) and a complete sequence of $PVY^O$ (Singh and Singh, 1996) (reference number: PVYN-Fr: Do00441; PVYN-605: X97895; PVYN-Egypt: AF522296; PVYN-Jg: AY166867; PVYNTN-H: M95491; PVYNTN-Tu660: AY16866; PVYO-139: U09509) were published.

In addition to the serological tools described above, molecular tests were developed by various teams. None of these tools, however, is capable of precisely characterizing the PVY isolates that induce necrosis. To solve this problem, we have developed molecular tools that are faster, more reliable and more specific for the detection of viruses capable of inducing necrosis in an infected plant. In other words, the invention provides, for the first time, a test enabling such discrimination between various isolates and, more particularly, highly sensitive detection of PVY according to its various biological properties [for example, necroses ($Y^N$) or mottling ($Y^O$)] with respect to the actual biological properties used in the classification of PVY.

Within the framework of our investigations, we have discovered two mutations in these various isolates directly implicated in necrosis, in particular tuber necrosis in the potato, and other plants of the Solanaceae family.

This discovery was only made possible by a reverse genetics approach in which mutations of amino acids located in the carboxy-terminus portion of the HC-Pro protein were identified as being responsible for necrosis.

The invention now opens the way for the systematic detection of necrotic and non-necrotic PVY isolates, which will enable producers to significantly decrease the risk of crop loss.

DESCRIPTION

Thus, the present invention relates to a method for detecting the presence or absence of PVY strains responsible for veinal, foliar or tubercular necrosis in plants of the Solanaceae family, characterized such that it comprises the following steps:

a) extraction of nucleic acids from a plant sample, b) RT-PCR amplification of a region of PVY viral RNA comprising codons 738 and 757 (SEQ ID No 1 and 3), which correspond to amino acids 400 and 419, respectively, of the HC-Pro protein (SEQ ID No 2 and 4, 7A and 7B), c) detecting the presence or absence of the $R/K_{400}$ and $D/E_{419}$ mutations, the detection of at least one said mutation being an indication of a virulent strain of PVY capable of causing necrosis in plants of the Solanaceae family.

In the description, reference will be made to the numbering of NCBI sequence X97895 (Jakab G., Droz E., Brigneti G., Baulcombe D. and Malnoe P., *Infectious in vivo and in vitro transcripts from a full-length cDNA clone of PVY-N605, a Swiss necrotic isolate of potato virus*, Y. J. Gen. Virol. 78 (Pt 12), 3141-3145 (1997)). The nucleotide and peptide sequences are presented in SEQ ID No 1 and 2, respectively. For $PVY^O$ strains, a reference sequence is available at NCBI under number U09509 [Singh M. and Singh R. P., *Nucleotide sequence and genome organization of a Canadian isolate of*

*the common strain of potato virus Y (PVYo). Can. J. Plant Pathol.* 18, 209-214 (1996)] (SEQ ID NO 3 and 4), but the numbering will be according to Jakab et al. (1997) by alignment.

In a first embodiment, the invention relates to a method described above for detecting the presence or absence of PVY strains responsible for veinal, foliar or tubercular necrosis in plants of the Solanaceae family, characterized such that step c) comprises the detection on the cDNA obtained in step b) of the presence or absence of mutations corresponding to $R/K_{400}$ and $D/E_{419}$ by means of i) at least one labeled probe specific to a polymorphism on codon 738 and ii) at least one labeled probe specific to a polymorphism on codon 757, said probes i) and ii) carrying labels that emit a different fluorescent signal, the presence of at least one of said $R/K_{400}$ and $D/E_{419}$ mutations being an indication of the presence of a virulent strain of PVY responsible for necrosis in plants of the Solanaceae family.

In a second embodiment, the invention relates to a method described above, characterized such that step c) comprises the detection on the cDNA obtained in step b) of the presence or absence of mutations corresponding to $R/K_{400}$ and $D/E_{419}$ by means of an oligonucleotide primer extension reaction using ddNTP labeled differentially and i) of an unlabeled primer that hybridizes specifically upstream or downstream (±1 nt) of polymorphic nucleotide 2213 of codon 738 and ii) of an unlabeled primer that hybridizes specifically upstream or downstream (±1 nt) of polymorphic nucleotide 2271 of codon 757, the presence of at least one of said $R/K_{400}$ and $D/E_{419}$ mutations being an indication of the presence of a virulent strain of PVY responsible for necrosis in plants of the Solanaceae family.

Using this method, the following genotypes/phenotypes are detected in a single test:
- [$R_{400}$, $D_{419}$] (strain incapable of inducing necrosis)
- [$R_{400}$, $E_{419}$] (strain capable of inducing necrosis)
- [$K_{400}$, $D_{419}$] (strain capable of inducing necrosis)
- [$K_{400}$, $E_{419}$] (strain inducing necrosis)

Examples of detected sequences containing one of these combinations of polymorphisms are presented in FIG. 6B (SEQ ID No 14 to 19).

Figure 6A:
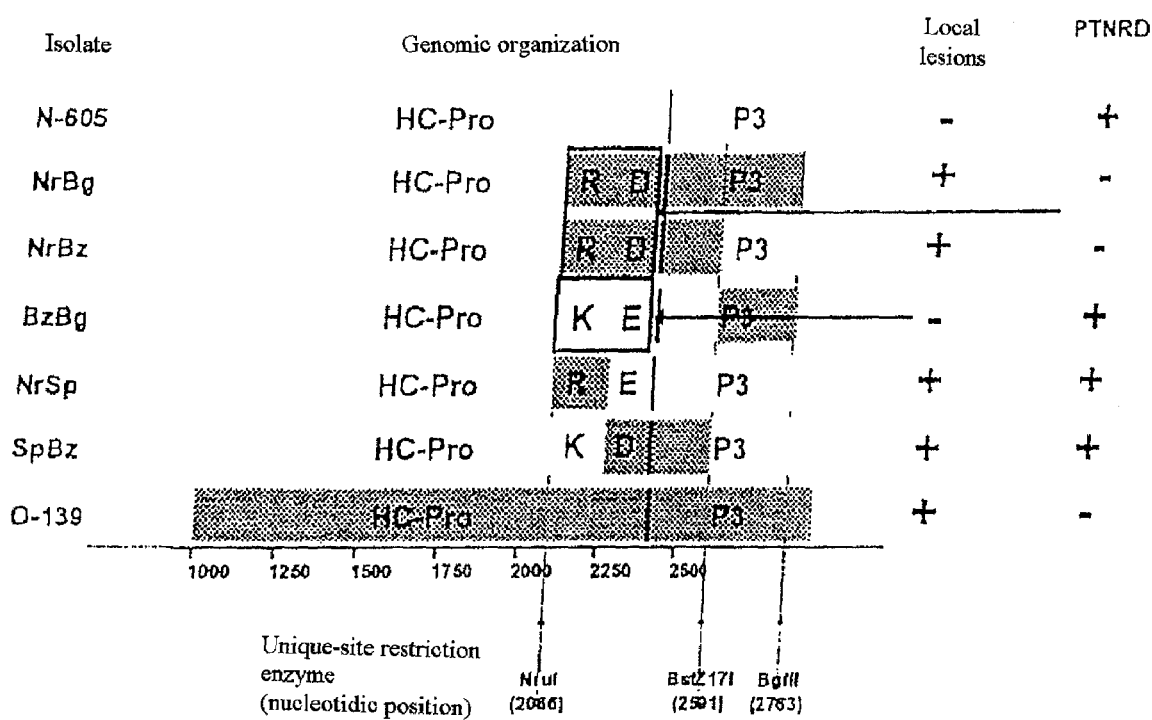

As an example, this method can be implemented with the potato. In this case, the detection in step c) of PVY [$R_{400}$, $E_{419}$] and/or [$K_{400}$, $D_{419}$] strains and/or [$K_{400}$, $E_{419}$] is an indication that the potato plant is contaminated with one or more strains capable of inducing tubercular necrosis (FIG. 6A).

In the first embodiment, the probe i) used in step c) comprises at least one probe specific to a polymorphism on codon 738 (corresponding to $R/K_{400}$), in particular a probe that hybridizes specifically with the target sequence when codon 738 is AAA with polymorphism $A_{2213}$. The test can be supplemented with other probes according to other polymorphisms on this codon: K (Lysine): AAA, AAG.

Preferably, a probe is used containing from 14 to 40, 15 to 25, 18 to 22 or 20 consecutive nucleotides of a sequence capable of hybridizing with sequence SEQ ID NO 5 (FIG. 1) and comprising the nucleotide in position 2213, in particular SEQ ID No 7: ctcaaatgaaaatattctac.

A control probe i) can also be used in step c), in particular a probe that hybridizes specifically with the target sequence when codon 738 is AGA with polymorphism $G_{2213}$. The test can be supplemented with other probes according to other polymorphisms on this codon: R (Arginine) CGT, CGC, CGA, CGG, AGA, AGG.

To this end, a control probe can be used containing from 14 to 40, 15 to 25, 18 to 22 or 20 consecutive nucleotides of a sequence capable of hybridizing with sequence SEQ ID No 6 (FIG. 1) and comprising the nucleotide in position 2213, in particular SEQ ID No 8: ctcaaatgagaatattcta.

Advantageously, probe i) and control probe i) are labeled differently.

Also in a preferred embodiment, probe ii) in step c) comprises at least one probe specific to a polymorphism on codon 757 (corresponding to $D/E_{419}$), in particular a probe that hybridizes specifically with the target sequence when codon 757 is GAA with polymorphism $A_{2271}$. The test can be supplemented with other probes according to other polymorphisms on this codon: E (Glutamic): GAA, GAG.

Preferably, a probe is used containing from 14 to 40, 15 to 25, 18 to 22 or 20 consecutive nucleotides of a sequence hybridizing with sequence SEQ ID NO 5 (FIG. 1) and comprising the nucleotide in position 2271, in particular with SEQ ID No 9 or SEQ ID No 10, which are specific YN probes: 5'-cgatcacgaaacgcagaca-3' (SEQ ID No 9) 5'-atcacga aacgcagaca-3' (SEQ ID No 20).

A control probe ii) can also be used in step c), in particular a probe that hybridizes specifically with the target sequence when codon 757 is GAC with polymorphism $C_{2271}$. The test can be supplemented with other probes according to other polymorphisms on this codon: D (Aspartic): GAT, GAC.

To this end, a control probe ii) can be used containing from 14 to 40, 15 to 25, 18 to 22 or 20 consecutive nucleotides of a sequence hybridizing with sequence SEQ ID No 6 (FIG. 1) and comprising the nucleotide in position 2271, in particular with SEQ ID No 10: 5'-accatgacactcaaa-3' or with SEQ ID No 21: 5'-tgaccatgacactcaa-3'.

Advantageously, probe ii) and control probe ii) are labeled differently.

Probes as described above containing a fluorescent label (reporter) and a molecule capturing the signal when it is near the fluorescent label (quencher) can be used.

In the second embodiment, the method described above is characterized such that the primer i) used in step c) is comprised of at least one primer that hybridizes specifically upstream or downstream of the polymorphic nucleotide of codon 738 (corresponding to $R/K_{400}$), in particular a primer that hybridizes specifically with the target sequence when codon 738 is AAA with polymorphism $A_{2213}$.

Preferably, primer i) contains from 10 to 120 or 20 consecutive nucleotides of a sequence hybridizing with sequence SEQ ID NO 5 (FIG. 1) and comprising the nucleotide in position 2212 or 2214.

In the second embodiment, the primer ii) used in step c) can also be at least one primer that hybridizes specifically upstream or downstream of the polymorphic nucleotide of codon 757 (corresponding to $D/E_{419}$), in particular a primer that hybridizes specifically with the target sequence when codon 757 is GAA with polymorphism $A_{2271}$.

Preferably, primer ii) contains from 10 to 120 or 20 consecutive nucleotides of a sequence hybridizing with sequence SEQ ID NO 5 (FIG. 1) and comprising the nucleotide in position 2270 or 2272.

As examples, in the second embodiment, the detection and identification of the polymorphic nucleotide in position 2213 is carried out with a sense primer selected among:

a sense primer selected among:
Oli1:
SEQ ID No 34
5'-GACAACTTGTGCTCAAATGA-3'

Oli2:
SEQ ID No 35
5'-CTGGCGACAACTTGTGCTCAAATGA-3'

-continued

Oli3:
SEQ ID No 36
5'-TGGATCTGGCGACAACTTGTGCTCAAATGA-3'

Oli4:
SEQ ID No 37
5'-CATGATGGATCTGGCGACAACTTGTGCTCAAATGA-3'

Oli5:
SEQ ID No 38
5'-CCAACCATGATGGATCTGGCGACAACTTGTGCTCAAATGA-3' and an antisense primer selected among:
Oli6:
SEQ ID No 39
5'-GAACATCAGGGTAGAATATT-3'

Oli7:
SEQ ID No 40
5'-ATCATGAACATCAGGGTAGAATATT-3'

Oli8:
SEQ ID No 41
5'-TCTGCATCATGAACATCAGGGTAGAATATT-3'

Oli9:
SEQ ID No 42
5'-GCAGTTCTGCATCATGAACATCAGGGTAGAATATT-3'

Oli10:
SEQ ID No 43
5'-TCTAGGCAGTTCTGCATCATGAACATCAGGGTAGAATATT-3'

In addition, the detection and identification of the polymorphic nucleotide in position 2271 are carried out with a sense primer selected among:

Oli11:
SEQ ID No 44
5'-GCCTAGAATACTAGTCGATCACGA-3'

Oli12:
SEQ ID No 45
5'-GAACTGCCTAGAATACTAGTCGATCACGA-3'

Oli13:
SEQ ID No 46
5'-GAACTGCCTAGAATATTGGTTGACCATGA-3'

Oli14:
SEQ ID No 47
5'-ATGCAGAACTGCCTAGAATACTAGTCGATCACGA-3'

Oli15:
SEQ ID No 48
5'-ATGCAGAACTGCCTAGAATATTGGTTGACCATGA-3' and an antisense primer selected among:
Oli16:
SEQ ID No 49
5'-GTCGACCACATGGCATGTCTGAGT-3'

Oli17:
SEQ ID No 50
5'-AACGAGTCGACCACATGGCATGTCTGAGT-3'

Oli18:
SEQ ID No 51
5'-AACGAGTCAACTACATGGCATGTCTGCGT-3'

Oli19:
SEQ ID No 52
5'-AACCAAACGAGTCGACCACATGGCATGTCTGAGT-3'

Oli20:
SEQ ID No 53
5'-AGCCAAACGAGTCAACTACATGGCATGTCTGCGT-3'

Regardless of the embodiment of step c), step b) can be defined as follows:

The RT and PCR steps take place one after the other in the same tube. For step b), reverse transcription is carried out with at least two or four pairs of sense and antisense primers, more particularly at least a first pair enabling the amplification of nucleotide sequences including codons 738 and 757 of PVY-N strains, at least a second pair enabling the amplification of nucleotide sequences including codons 738 and 757 of $PVY^{O}$ strains.

Said first pair of primers (FpN and RpN) preferably comprises an FpN sense primer and an RpN antisense primer that can contain a sequence of 20 to 40 consecutive nucleotides of a sequence that hybridizes with sequence SEQ ID No 1 or 5. The FpN sense primer is preferably located upstream of polymorphic codon 738 and the RpN primer is preferably located downstream of polymorphic codon 757.

Alternately, two first pairs can be used as follows:

FpN1 upstream of codon 738

RpN1 downstream of codon 738

FpN2 upstream of codon 757

RpN2 downstream of codon 757

Said second pair of primers (FpO and RpO) preferably comprises an FpO sense primer and an RpO antisense primer that can contain a sequence of 20 to 40 consecutive nucleotides of a sequence that hybridizes with sequence SEQ ID NO 3 or 6. The FpO sense primer is preferably located upstream of polymorphic codon 738 and the RpO primer is preferably located downstream of polymorphic codon 757.

In another alternative, two second pairs can be used as follows:

FpO1 upstream of codon 738

RpO1 downstream of codon 738

FpO2 upstream of codon 757

RpO2 downstream of codon 757

This preferred embodiment is not limiting. Indeed, the invention also relates to a method such as defined above in which step b) comprises the use of a number of pairs of primers covering the entire PVY virus spectrum.

An example of an embodiment is presented in FIG. 2. Among these primers, SEQ ID No 11 and 12 can be cited.

In a preferred embodiment, the two pairs of primers are selected among:

Sense primers for YN:

Sense primers for YN:
SEQ ID No 22
F1: 5'-ATGATGCAGAACTGCCTAGAATACTAGT-3'

SEQ ID No 23
F2: 5'-ATGATGCAGAACTGCCTAGAATACTAGTC-3'

SEQ ID No 24
F3: 5'-CATGATGCAGAACTGCCTAGAATACTA-3'

Antisense primers for YN:
SEQ ID No 28
R1: 5'-GTGAGCCAAACGAGTCAACTACAT-3'

SEQ ID No 29
R2: 5'-TTTGTGAGCCAAACGAGTCAACTA-3'

SEQ ID No 30
R3: 5'-TTGTGAGCCAAACGAGTCAACT-3'

```
-continued
Sense primers for YO:
                                      SEQ ID No 25
F1:   5'-GCAGAGCTGCCTAGTTTATTGGTT-3'

SEQ ID No 26
F2:   5'-ATGATGCAGAGCTGCCTAGTTTATT-3'

SEQ ID No 27
F3:   5'-TGCAGAGCTGCCTAGTTTATTGG-3'

Antisense primers for YO:
                                      SEQ ID No 31
R1:   5'-GCCAAATGAGTCAACCACATGA-3'

SEQ ID No 32
R2:   5'-AGCCAAATGAGTCAACCACATG-3'

SEQ ID No 33
R3:   5'-CCAAATGAGTCAACCACATGACA-3'
```

The invention also relates to a sanitary method for selecting seedlings belonging to the Solanaceae family contaminated by PVY strains responsible for veinal, foliar or tubercular necrosis, in particular tubercular necrosis in the potato, comprising the systematic implementation of the detection method mentioned above on seeds, seedlings and/or plants to be cultivated and then proceeding with the destruction or quarantine of said seeds, seedlings or plants contaminated with a strain exhibiting at least one of the polymorphisms corresponding to:

[$R_{400}$, $E_{419}$] (strain capable of inducing necrosis)

[$K_{400}$, $D_{419}$] (strain capable of inducing necrosis)

[$K_{400}$, $E_{419}$] (strain inducing necrosis)

Sanitary control can be carried out as mentioned above with seeds, seedlings and/or plants imported into a given region, for example those entering the European Union or Canada or those arriving from risk regions.

In another aspect, the invention relates to a kit for detecting the presence or absence of PVY viruses responsible for veinal, foliar or tubercular necrosis in plants of the Solanaceae family, characterized such that it comprises:

- at least a first pair of primers enabling the amplification of nucleotide sequences including codons 738 and 757 of $PVY^N$ strains, at least a second pair of primers enabling the amplification of nucleotide sequences including codons 738 and 757 of $PVY^O$ strains,
- at least one labeled probe i) specific of a polymorphism on codon 738 and at least one labeled probe ii) specific for a polymorphism on codon 757, said probes i) and ii) being such as described above and carrying labels that emit different fluorescent signals.

The kit can also include control probes i) and ii) as described above, control probes i) and ii) being labeled with different fluorescent labels, probes ii) and controls ii) being labeled with different fluorescent labels.

In the case where the step corresponds to the second embodiment, the kit for detecting the presence or absence of PVY virus isolates responsible for veinal, foliar or tubercular necrosis in plants of the Solanaceae family is characterized such that it comprises:

- at least a first pair of primers enabling the amplification of nucleotide sequences including codons 738 and 757 of $PVY^N$ strains, at least a second pair of primers enabling the amplification of nucleotide sequences including codons 738 and 757 of $PVY^O$ strains,
- an unlabeled primer that hybridizes specifically upstream or downstream (±1 nt) from polymorphic nucleotide 2213 of codon 738 and ii) of an unlabeled primer that hybridizes specifically upstream or downstream (±1 nt) of polymorphic nucleotide 2271 of codon 757. Numerous examples of sense primers and antisense primers specific polymorphs 2213 and 2271, respectively, have been previously described.

The kit can also include a means for extracting the nucleic acids of a plant sample, for example viral RNA crushing buffer and extraction buffer as described below. The kit can also include the reagents necessary for amplification and/or a device for the qualitative and quantitative detection of fluorescent signals.

As an example, the kit can include a solution comprising the primers for use at an optimal concentration between 400 nM and 1200 nM, in particular 800 nM, and a solution comprising the probes at a concentration between 100 nM and 300 nM, in particular 200 nM.

In another aspect, the invention relates to a probe or primer and to the probe and primer collections mentioned above.

In another aspect, the invention relates to the use of said probes, primers, probe collections and primer collections for detecting the presence or absence of PVY viruses responsible for veinal, foliar or tubercular necrosis in plants of the Solanaceae family, the potato in particular, and also eggplant, tomato, pepper or tobacco.

Thus, in the present invention, we propose a nucleotide polymorphism assay for the detection of $PVY^N$ and $PVY^O$ isolates that targets a specific molecular label related to the capacity of the members of the $PVY^N$ group to cause necrosis. The protocol developed comprises a rapid procedure for sampling plants, a rapid nucleic acid extraction process ("wet leaf") and a single-step fluorescent RT-PCR reaction (using at least two TaqMan® probes), which does not require post-PCR handling.

Such characteristics make it possible to perform up to 96 tests in less than three hours, starting with plant sampling and ending with the generation of diagnostic results.

The single nucleotide polymorphism (SNP) diagnostic test described above reliably detected 42 PVY isolates from 13 countries and was able to correctly assign them to the $PVY^N$ or $PVY^O$ group. The samples containing more than $10^4$ copies of the $PVY^N$ and/or $PVY^O$ RNA were detected efficiently by this test, the latter enabling co-detection of $PVY^N$ and $PVY^O$ in mixed infections.

This new detection tool combines the high sensitivity of molecular detection techniques with speed (RT-PCR series performed in roughly two hours), simplicity (no extraction kit required for sample preparation and a gel-free procedure) and compatibility with robotic apparatuses used for serological assays. The principal improvements provided by this PVY detection test are, firstly, the choice of using SNP technology, typically used for allelic discrimination assays, genetic segregation analyses and chromosomal mapping of diploids (for a review, see Oefner, 2002).

In addition, we provide for the first time a test that specifically detects PVY isolates that induce necrosis from a virulent isolates by virtue of the identification of the characteristics of the polymorphic nucleotides cited above. Applied to haploids (such as single-stranded RNA viruses), the inventive technology has the potential to identify samples containing only one (visualized as a homozygote) or a combination of two variants (considered by the test as a heterozygote) of the targeted polymorphic sequence.

Thus, the invention also relates to a lot of seeds, seedlings and/or plants of the Solanaceae family, characterized such that it is free of seeds, seedlings or plants contaminated by PVY and that it exhibits at least one of the polymorphisms corresponding to:

[$R_{400}$, $E_{419}$] (strain capable of inducing necrosis)

[$K_{400}$, $D_{419}$] (strain capable of inducing necrosis)

[$K_{400}$, $E_{419}$] (strain inducing necrosis)

Among these lots, the invention relates to lots of tomatoes, peppers, tobacco, sweet peppers and eggplants. Preferably, the invention relates to a lot of seedlings or potato tubers, characterized such that that it is free of seedlings or tubers contaminated with a PVY strain and such that it exhibits at least one of the polymorphisms corresponding to:

[$R_{400}$, $E_{419}$] (strain capable of inducing necrosis)
[$K_{400}$, $D_{419}$] (strain capable of inducing necrosis)
[$K_{400}$, $E_{419}$] (strain inducing necrosis)

The above-mentioned lots are obtained by the implementation of the method or of the kit described above.

Figure legends will be referred to in the subsequent description.

FIGURE LEGENDS

FIG. 1: Sequences surrounding the polymorphisms responsible for necrosis

FIG. 2: Sequences of $PVY^N$-605 (SEQ ID NO: 5) and $PVY^O$-139 (SEQ ID NO: 6) used as a target in a nucleotide polymorphism assay. The binding sites for the sense primers (FpN and FpO), the antisense primers (RpN and RpO) and the two TAQMAN probes (Probe$^N$ and Probe$^O$) are presented. Polymorphic nucleotide $A/G_{2213}$ is indicated. The specific indicators (reporters) for the probes (FAM and Vic for Probe$^N$ and Probe$^O$, respectively) are illustrated by a gray square and a circle, respectively. Quenchers, non-fluorescent binding molecules (MGB [Applied Biosystems]) incorporated at the 3' end of the fluorescent probes, are indicated by gray stars.$^a$ Nucleotide positions given are as in Jakab et al., (1997).

FIG. 3: Raw fluorescence signal (RFS) obtained using positive (mixed $PVY^N$, $PVY^O$ and $Y^N/Y^O$) and negative (control without matrix) control samples.

A. RFS data for probes specific to $PVY^N$ (FAM) and $PVY^O$ (Vic). The average values and standard deviations calculated with four replications of NTC, pure $PVY^N$-605 and pure $PVY^O$-139 are indicated. The values obtained with both replicates of mixed $Y^N/Y^o$ samples are listed.

B. Schematic representation of RFS data. Each point corresponds to the data (FAM, Vic) associated with one of the samples tested. Four non-overlapping regions were defined according to the nature of the samples tested.

Figure 4A:
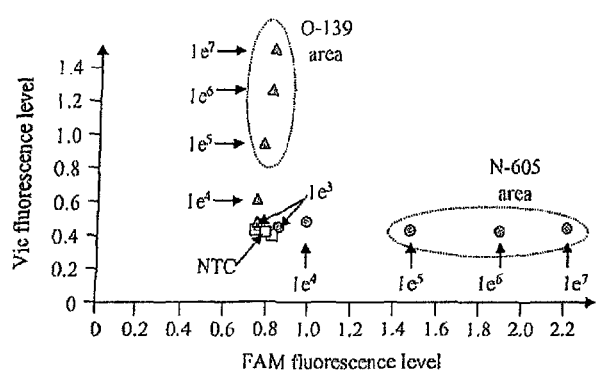
Figure 4B:
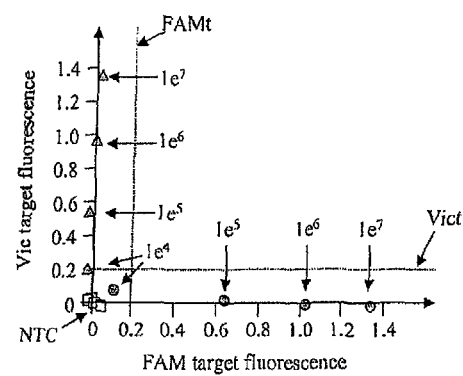
Figure 4C:
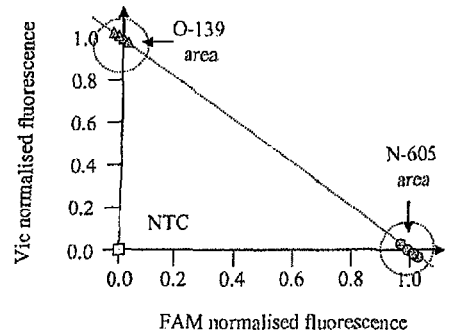

FIG. 4: Schematic representation of the raw (A), target (B) and normalized (C) fluorescent data. The triangles, squares and circles correspond to the pure $PVY^O$, NTC and pure $PVY^N$ samples. The theoretical quantity of PVY RNA present in each sample tested is indicated. FAMt and Vict correspond to the thresholds for effective detection of $PVY^N$ and $PVY^O$, respectively. The regions of detection and characterization are indicated on the raw (A) and normalized (C) graphs.

Figure 5:
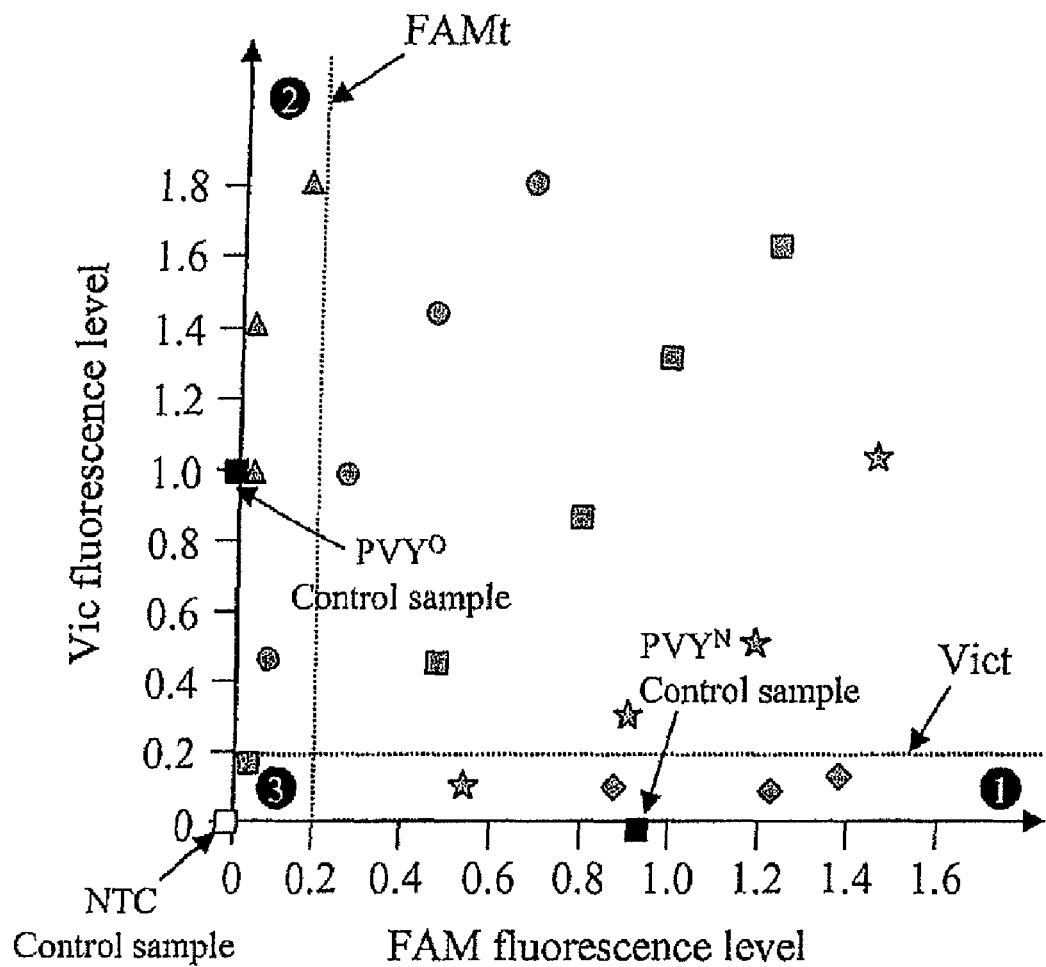

FIG. 5: Graphical representation of the co-detection of $PVY^N$ and $PVY^O$ using SNP fluorescent target data. The detection thresholds for $PVY^N$ and $PVY^O$ are indicated by FAMt and Vict, respectively. The single detection of $PVY^N$ and or $PVY^O$ corresponds to regions ❶ and ❷, respectively. The groups of region ❸ were not detected in the sample. $Y^N/Y^O$ ratios of 1/100, 1/10, 1, 10/1 and 100/1 are represented by triangles, circles, squares, stars and diamonds, respectively.

FIG. 6: Analysis of necrotic properties of chimeric PVY isolates in the potato.

FIG. 7: Sequence $PVY^N$-605, region of interest, HC-PRO

A. Nucleotide sequence (first 2820 nucleotides of SEQ ID NO: 1) (translation initiation codon in bold, polymorphic bases of interest in bold italics)

B. Polyprotein amino acid sequence (SEQ ID NO: 2) (containing the underlined HC-Pro protein sequence), the amino acid of interest in bold.

FIG. 8: $PVY^O$-139 sequence, region of interest and HC-PRO

A. Nucleotide sequence (first 2820 nucleotides of SEQ ID NO: 3) (translation initiation codon in bold, polymorphic bases of interest in bold italics)

B. Polyprotein amino acid sequence (SEQ ID NO: 4) (containing the underlined HC-Pro protein sequence), amino acid of interest in bold.

FIG. 9: Schematic diagram of the method for characterizing polymorphic nucleotides using the single nucleotide primer extension technique. The steps (extraction, RT-PCR, SNaPshot extension and polyacrylamide gel electrophoresis) ranging from the plant sample to the result obtained by computer analysis of the fluorescent signal are presented. Primers linked to fluorescent ddNTP are visualized using laser excitation after migration in a polyacrylamide gel.

FIG. 10: Electropherograms obtained using the technique of labeling specific primers with ddNTP for the various polymorphic sites to be characterized. Each site is studied using a specific primer that hybridizes upstream (or downstream; the antisense primer is not illustrated) of the polymorphic site. The various primers have various lengths in order to enable their characterization for migration. The peaks obtained reveal the presence of fluorescent primers in expected sizes. The nature of the fluorescence enables the characterization of the nucleotide of the polymorphic site of interest.

EXAMPLE 1

Origin of PVY Strains and Sample Preparation 1.1 Viruses and Host Plants

Forty-two PVY isolates, characterized serologically and molecularly, belonging to the various PVY groups ($PVY^N$ or $PVY^O$) and variants ($Y^{NTN}$ or $Y^N$-W, table 1) were used in this study. $PVY^N$-605 (Jakab et al., 1997) and $PVY^O$-139 (Singh and Singh, 1996) were used as reference isolates for groups $PVY^N$ and $PVY^O$, respectively. They were used to develop the test whereas other PVY isolates were used in the process of evaluating the assay developed. The isolates were maintained in a greenhouse by mechanical inoculation on *Nicotiana tabacum* cv. *Xanthi*, which was used as a test plant in a biological test for characterizing $PVY^N$ and $PVY^O$ isolate on the basis of their capacity or incapacity to induce symptoms of leaf necrosis.

TABLE I

Origin of and references for PVY isolates tested within the framework of the invention

| Strain | Isolate | Origin | Reference |
|---|---|---|---|
| N | 605 | Switzerland | Jakab et al., 1997 |
| | C3VN | Scotland | Glais et al., 1996 |
| | Irl | Ireland | Glais et al., 1996 |
| | 607 | The Netherlands | Glais et al., 1996 |
| | P21 | Tunisia | Fakhfakh et al., 1996 |
| | B203 | France | Glais et al., 1998 |
| | Sp20 | Spain | Blanco-Urgoiti et al., 1998 |
| | Sp125 | Spain | Blanco-Urgoiti et al., 1998 |
| | TVNQ | Canada | Mc Donald and Kristjansson, 1993 |
| | B4 | France | From this report |
| | B7 | France | From this report |
| | B8 | France | From this report |
| O | 139 | Canada | Singh and Singh, 1996 |
| | Irl | Ireland | Glais et al., 1998 |

TABLE I-continued

Origin of and references for PVY isolates tested within the framework of the invention

| Strain | Isolate | Origin | Reference |
|---|---|---|---|
| | Sc | Scotland | Glais et al., 1998 |
| | N1702 | The Netherlands | Glais et al., 1998 |
| | Lw | Poland | Glais et al., 1998 |
| | B18 | France | From this report |
| N-W | i-P | Poland | Glais et al., 1998 |
| | N242 | France | Glais et al., 1998 |
| | B11 | France | Glais et al., 2002 |
| | Sp17 | Spain | Blanco-Urgoiti et al., 1998 |
| | B15 | France | From this report |
| | N5 | France | From this report |
| | N10 | France | From this report |
| | N12 | France | From this report |
| | N15 | France | From this report |
| | N324 | France | From this report |
| | N341 | France | From this report |
| | N362 | France | From this report |
| NTN | Lb | Lebanon | Glais et al., 1996 |
| | FrOrl | France | Glais et al., 1996 |
| | H | Hungary | Glais et al., 1996 |
| | CzLuk1 | Czech Republic | Glais et al., 1996 |
| | Sp47 | Spain | Blanco-Urgoiti et al., 1998 |
| | Lx2 | Tunisia | From this report |
| | B6 | France | From this report |
| | B9 | France | From this report |
| | N4 | France | From this report |
| | N18 | France | From this report |
| | May2 | France | From this report |
| | Dk | Denmark | From this report |

1.2 Sample Preparation

Raw juice was extracted from *N. tabacum* plants, healthy or infected by PVY, by pressing the leaves (0.5 g) in a cylinder press, in the presence of 1 ml of cold crushing buffer (PBS; 0.05% (v/v) Tween 20). These samples were used immediately to perform an ELISA or a nucleic acid extraction.

A rapid "wet leaf" extraction procedure adapted from Robert et al., 2000, was performed using three leaf disks (0.2 cm² each, collected using a microtube stopper as a perforation device) from each plant. The material collected was incubated for 15 min at 95° C. in 100 µl of crushing buffer and then placed at 4° C. for 10 min. After centrifugation (8,000 g for 5 min), the supernatant was collected, transferred to a new tube and diluted 10× in RNase-free water. Extracts were stored at −20° C. until use.

1.3 Immunoenzymatic Assay (ELISA).

PVY was detected in a plant using a double-antibody enzyme-linked immunosorbent assay (DAS-ELISA) protocol. Microtiter plate wells were filled with 1 µg/ml of PVY polyclonal antibody (FNPPPT-INRA, France) in a carbonate buffer (pH 9.6) for 2 h at 37° C. Between each stage of the ELISA protocol, the plates were washed three times with PBST buffer (PBS, 0.05% (v/v) Tween 20). 100 µl of raw plant juice were added to the wells which were left until the following day at 4° C. Mouse monoclonal antibodies conjugated with alkaline phosphatase and directed against $PVY^N$ [Bioreba, Switzerland] or $PVY^{O/C}$ [Adgen, UK] were diluted to 1/1000 or 1/2000, respectively, in a crushing buffer supplemented with 0.2% egg albumin (w/v). According to expected detection specificity, 100 µl of these monoclonal antibodies were added to the plate wells for 2 hours at 37° C. The plate wells were filled with 100 µl of p-nitrophenyl phosphate (1 mg/ml) in a substrate buffer (1 N diethanolamine, pH 9.6) After incubation for one hour at room temperature, the absorbance of the samples was read at 405 nm using a microtiter plate reader (Titertek Multiscan [MCC]).

1.4 Preparation of the Standard of Viral RNA for the Test by SNP

Total nucleic acid was extracted from 100 µl of raw juice taken from plants infected by $PVY^N$-605 or $PVY^O$-139, using a phenol/chloroform procedure, and suspended in 50 µl of nuclease-free water. Reverse transcription of viral RNA was performed using 3 U of AMV reverse transcriptase [Promega], 10 µmol of the oligonucleotide 5'-$^{9702}$GTCTC-CTGATTGAAGTTTAC$^{9682}$-3' (SEQ ID No 13) (nucleotide positions according to isolate $PVY^N$-605), 20 nmol of dNTP, 20 U of RNasin [Promega] and 10 µl of the total nucleic acid extract. The reaction was performed according to the enzyme manufacturer's instructions in a final volume of 20 µl. The cDNA regions corresponding to part of the HC-Pro/P3 genes of $PVY^N$-605 or $PVY^O$-139 were then amplified by PCR using 2.5 U of the AmpliTaq polymerase [Applied Biosystems], 40 pmol of the forward primer 5'-aacgtgtttctcgcgat-gctaattaacattggcgaggagg-3' (SEQ ID No 11 corresponding to nt 2079 to 2108 of $PVY^O$-139 and comprising an NruI site) and the reverse primer 5'-agccatcagtataccagggggataatat-tgatagaatcaac-3' (SEQ ID No 12 corresponding to nt 2592 to 2561 of $PVY^O$-139, and comprising a BstZ17I site), 20 nmol of dNTP, 75 nmol of $MgCl_2$ and 10 µl of cDNA adjusted a final volume of 50 µl with sterile water. The reaction was cycled using a Hybaid Express® thermal cycler for 40 cycles at 94° C. for 1 min, 52° C. for 1 min and 72° C. for 1 min. Separately, the PCR products corresponding to the $PVY^N$ or $PVY^O$ sequences were cloned into the NruI and BstZ17I sites in a modified pBluescript vector (pMTlink), in which the pBluescriptKS [Statagene] multiple cloning cassette was replaced between the KpnI and SacI sites by a short nucleotide sequence comprising the KpnI-NruI-BstZ17I-SacI unique restriction sites. The resulting $pMT_{NB}^N$ and $PMT_{NB}^O$ plasmids were used to produce viral RNA transcription products corresponding to nucleotides 2086 to 2591 of $PVY^N$-605 and $PVY^O$-139, respectively. Separately 1 µg of $pMT_{NB}^N$ and $PMT_{NB}^O$ was linearized by SacI, purified using a phenol/chloroform extraction protocol and suspended in 5 µl of nuclease-free water. PVY RNA transcription products were generated in the presence of 15 U of T3 RNA polymerase [Promega], 10 mM of rNTP and 5 mM of dithiotreitol (DTT) for 3 hours at 37° C. The in vitro transcription process was supplemented by the digestion of the plasmid using RNase-free DNase I for 15 min at 37° C. Viral transcription products were extracted using a phenol/chloroform extraction procedure and amyl alcohol, precipitated and suspended in 100 µl of RNase-free water. Final RNA concentration (µg/µl and copies/µl) was determined by spectrophotometry. $PVY^N$ and $PWY^O$ in vitro transcription products were diluted in order to obtain solutions containing $10^8$, $10^7$, $10^6$, $10^5$, $10^4$, $10^3$ or $10^2$ copies of the viral RNA produced in vitro in 2.5 µl.

EXAMPLE 2

Design of a Primer and a Probe and Detection SNP

PVY nucleotide 2213 (numbered according to Jakab et al., 1997), reported as being involved in tobacco brown-rib disease from $PVY^N$-605 (Balme-Sinibaldi et al., 2004), was chosen to define two probes labeled with TaqMan®-MGB FAM-(Probe$^N$) or Vic-(Probe$^O$) [Applied Biosystems] corresponding to $PVY^N$-605 or $PVY^O$-139 sequences, respectively (FIGS. 1 and 2). The sense (Fp) and antisense (Rp) primer pairs (FIG. 2) encompassing the sequences targeted by the probe for $PVY^N$-605 (FpN and RpN) and $PVY^O$-139 (FpO and RpO) were designed using Primer Express software [Applied Biosystems].

SNP Test Using TaqMan® Fluorescent Probes

TaqMan®-based SNP reactions were carried out in a final volume of 25 µl using the One-Step RT-PCR Master Mix Reagents Kit [Applied Biosystems] according to the manufacturer's instructions. RT-PCR reactions were carried out in a single step with 2.5 µl of "wet leaf" extracts from healthy or infected plants, or by using transcription products in vitro in the ABI PRISM 7700 Sequence Detection System [Applied Biosystems]. Viral RNA reverse transcription was carried out at 48° C. for 30 minutes. PCR was performed with a hot-start AmpliTaq polymerase [Applied Biosystems] using an enzymatic activation step (10 min at 95° C.), followed by denaturation/hybridization/extension cycles (15 sec at 95° C.; 1 min at 60° C.). For each sample, the fluorescent signals corresponding to FAM, Vic and to the internal control ROX of Applied Biosystems® were read at the end of the RT-PCR program. The data obtained (raw fluorescence) were transformed mathematically using SDS v1.7 software [Applied Biosystems] in order to produce data corresponding to the fluorescent signal of the target component (FAMm and Vicm) and to the normalized fluorescence data (FAMn and Vicn). The SNP test and the validation procedure were replicated in at least three independent experiments.

EXAMPLE 3

Detection of $PVY^N$-605 and $PVY^O$-139 in Pure and Mixed Samples Using an SNP Assay Following Example 2

Figures 3A, 3B:
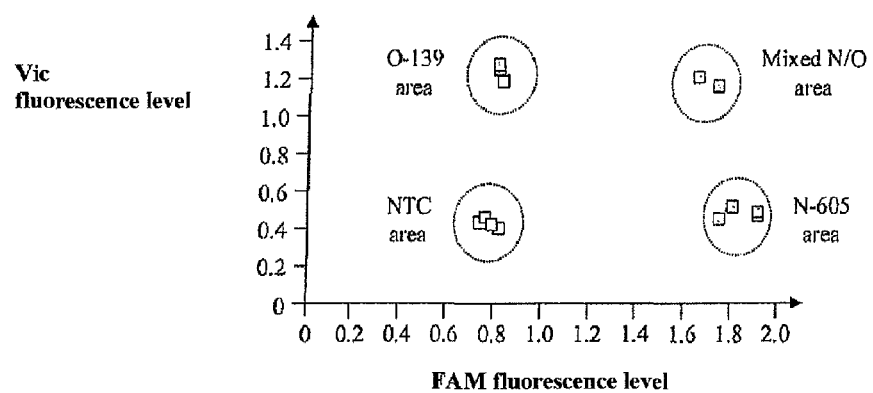

According to the manufacturer's recommendations, and taking into account previously published real-time RT-PCR protocols (Fabre et al., 2003; Roberts et al., 2000), the two TaqMan® probes (Probe$^N$ and Probe$^O$) and the primer pairs (FpN and RpN; FpO and RpO) were tested at various concentrations from 50 nM to 900 M. The fluorescent signals collected at the end of the PCR reactions were optimal when each probe was included at 200 nM and the four primers at 800 nM. Thirty-two PCR cycles were performed in all of the detection experiments in order to avoid the nonspecific probe cleavage observed in experiments using more than 35 PCR cycles. The SNP test was repeated four times, including a control without a matrix (NTC) or in vitro viral RNA transcription products ($10^6$ $PVY^N$ or $10^6$ $PVY^O$ copies/reaction) and with duplication of the mixed samples containing $PVY^N$ and $PVY^O$ ($10^6$ of each type of RNA). The raw fluorescence signals (RFS) associated with each probe were recorded at the end of the single-step RT-PCR reaction (FIG. 3). For the NTC samples, RFS corresponds to the baseline system fluorescence level (0.782±0.024 and 0.424±0.008 for the fluorescence of FAM and Vic, respectively), produced by the uncleaved probes (FIG. 3A). When the samples containing RNA transcription products were tested, the probe-associated RFS increased according to the type of RNA present in the samples tested [Probe$^N$ (FAM signal) and Probe$^O$ (Vic signal) for $PVY^N$ and $PVY^O$ respectively]. This result shows highly specific hybridization of the probes to their RNA targets and the absence of any significant level of nonspecific interaction. In the mixed $Y^N/Y^O$ samples, the fluorescent signals of both FAM and Vic increased significantly when compared with NTC data, reflecting the binding and cleaving of two probes for the PCR reaction. The graphical representation of raw fluorescent signal data (FIG. 3B) illustrates both the distinction of four regions corresponding to each sample tested and the variation in the fluorescence level within these regions recorded during each replication.

EXAMPLE 4

Test of the Sensitivity of the $PVY^{N/O}$ SNP Test

Fractions from a series of dilutions containing from $10^7$ to $10^3$ copies of RNA/2.5 µl of in vitro $PVY^N$ and $PVY^O$ transcripts were produced and tested using the SNP test protocol in order to establish the detection limit of this novel method (FIG. 4). Good correlation could be observed between decreasing viral quantity in the samples tested and the drop in fluorescent signal, for both $PVY^N$ and $PVY^O$ (FIG. 4A). The three most concentrated dilutions were effectively detected and identified as $PVY^N$ or $PVY^O$ by SNP assay (FIG. 4A); $10^7$, $10^6$ and $10^5$ fractions in the $PVY^N$ and $PVY^O$ regions). However, when the samples containing only $10^4$ and $10^3$ RNA molecules were tested, the fluorescent data obtained were either close to ($10^4$) or indistinguishable from ($10^3$) those associated with NTC samples. These data variations for the NTC replications (FIGS. 3A and 3B) indicate that it is difficult to clearly identify the fluorescent threshold that delimits PVY-positive detection from PVY-negative detection. In order to solve this problem, the SDS® software [Applied Biosystems] enables mathematical transformations of the raw fluorescent signal into target fluorescence data (FIG. 4B) and normalized fluorescence data (FIG. 5C). These data make it possible to precisely set the SNP assay evaluation criterion dilution in the range of $10^4$ to $10^5$ for $PVY^N$ and $PVY^O$.

EXAMPLE 5

Co-Detection of Mixed $PVY^N$ and $PVY^O$ in Samples (Mimicking a Co-Infection)

By using fractions containing between $10^4$ and $10^8$ $PVY^N$ or $PVY^O$ in vitro transcription products [NruI-BsZ17I], several mixed fractions were prepared by creating samples with $Y^N/Y^O$ ratios of 1/100 to 100/1 (table 2 and FIG. 5). These fractions were tested as unknown samples in an SNP assay comprising NTC, pure $PVY^N$ control samples ($10^6$ transcription products) and pure $PVY^O$ ($10^6$ transcription products). The raw fluorescence data obtained from the pure samples (FAM=1.753 and Vic=1.276 for $PVY^N$ and $PVY^O$, respectively) were equivalent to those obtained in the mixed samples containing $10^6$ copies of the two types of RNA (1/1 ratio; $10^6$ copies of $PVY^N$ and $PVY^O$; FAM=1.653 and Vic=1.198). This illustrates that single detection and co-detection of $PVY^N$ and/or $PVY^O$ in samples containing similar quantities of targeted RNA were effective for both targets. As previously shown, the quantity of PVY RNA present in the samples tested influences the raw fluorescence level directly. Fractions containing $10^8$ copies of both types of PVY RNA were associated with high RFS values (close to 2.000), whereas the fractions containing only $10^4$ copies of PVY RNA produced RFS data (FAM=0.860 and Vic=0.563) close to those expected for the negative control (NTC; FAM=0.754 and Vic=0.427). The use of target fluorescence data (table 2) with the FAMt and Vict detection threshold (FIG. 5) made it easy to distinguish single detection from co-detection. By taking the observations into account, the fractions with quantities of PVY RNA from $10^5$ to $10^8$ with a $Y^N/Y^O$ ratio of 1 were effectively characterized as mixed samples. When fractions containing one type of PVY RNA in excess (ratio=1/100, 1/10, 10/1 or 100/1) were tested, the RFS for a constant quantity of a type of PVY RNA is reduced according to the excess of the other type of PVY RNA (PVY$^N$=10$^6$: FAMm was 1.216, 0.970, 0.798, 0.454 and 0.68 for the samples containing 10$^4$, 10$^5$, 10$^6$, 10$^7$ and 10$^8$ PVY$^O$, respectively).

EXAMPLE 6

Validation of the SNP Test on a Wide Range of PVY Isolates

The SNP test developed was validated using a wide range of PVY isolates comprising 37 European isolates, two African isolates, two North-American isolates and one isolate from the Near East, belonging to the PVY$^N$ and PVY$^O$ groups, comprising the variants PVY$^{NTN}$ and PVY$^N$-W (table 1). The biological and serological properties of 42 isolates were characterized using observations of symptoms on *N. tabacum* cv. *Xanthi* and ELISAs (table 3). All of the results were in agreement with the expected results. "Wet leaf" extracts of *N. tabacum* cv. *Xanthi* infected by these PVY isolates were prepared and then tested using the SNP test developed. The target fluorescence data and the SNP diagnostic results associated with each sample tested are presented in table 3. All 42 of the PVY isolates tested could be correctly assigned by the SNP test to their respective PVY group. Variants PVY$^{NTN}$ and PVY$^N$-W were correctly characterized as members of the PVY$^N$ group. As was expected, none the samples tested from our collection of PVY isolates was identified by the SNP test as a co-infected sample.

EXAMPLE 7

Figure 9:
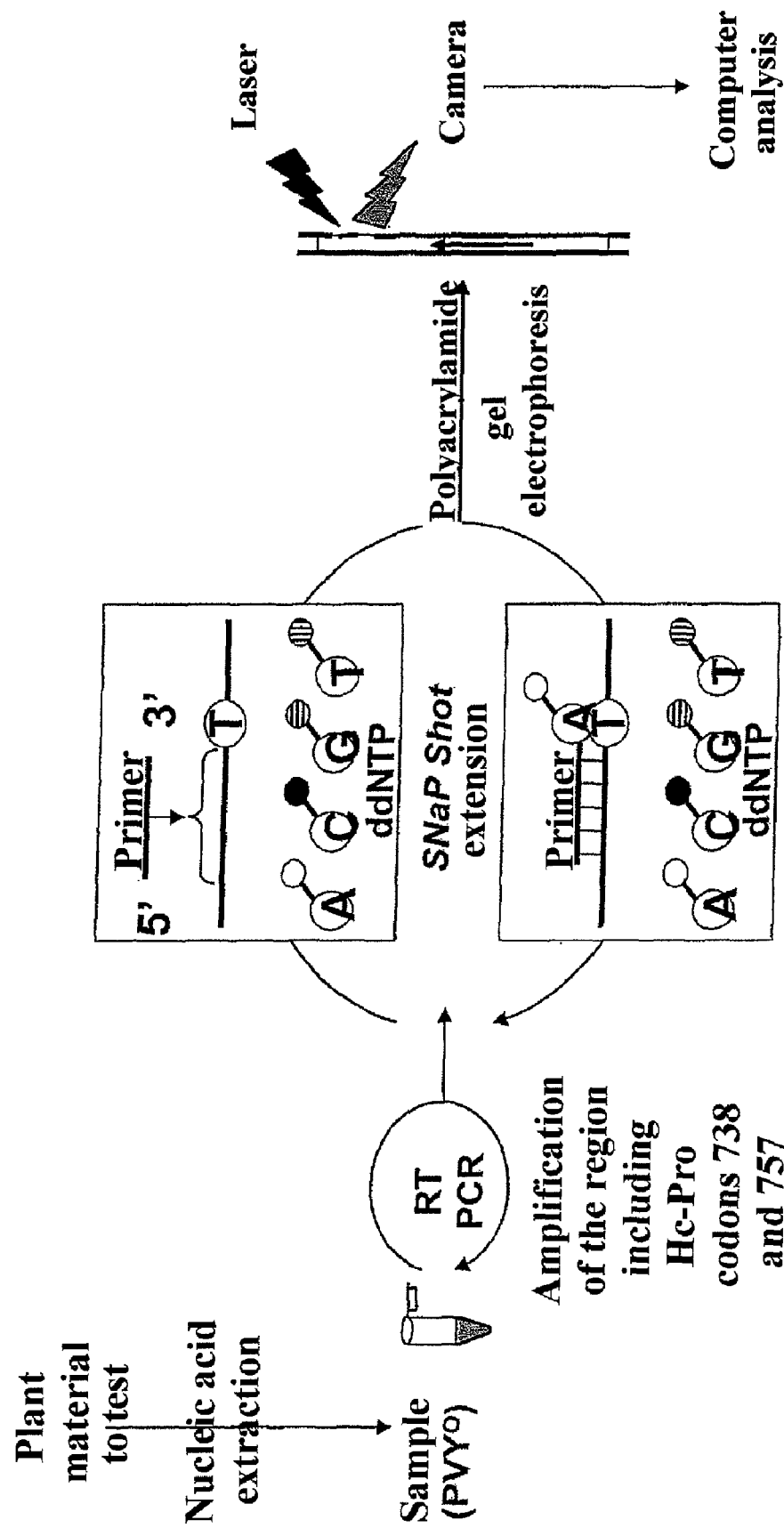
Figure 10:
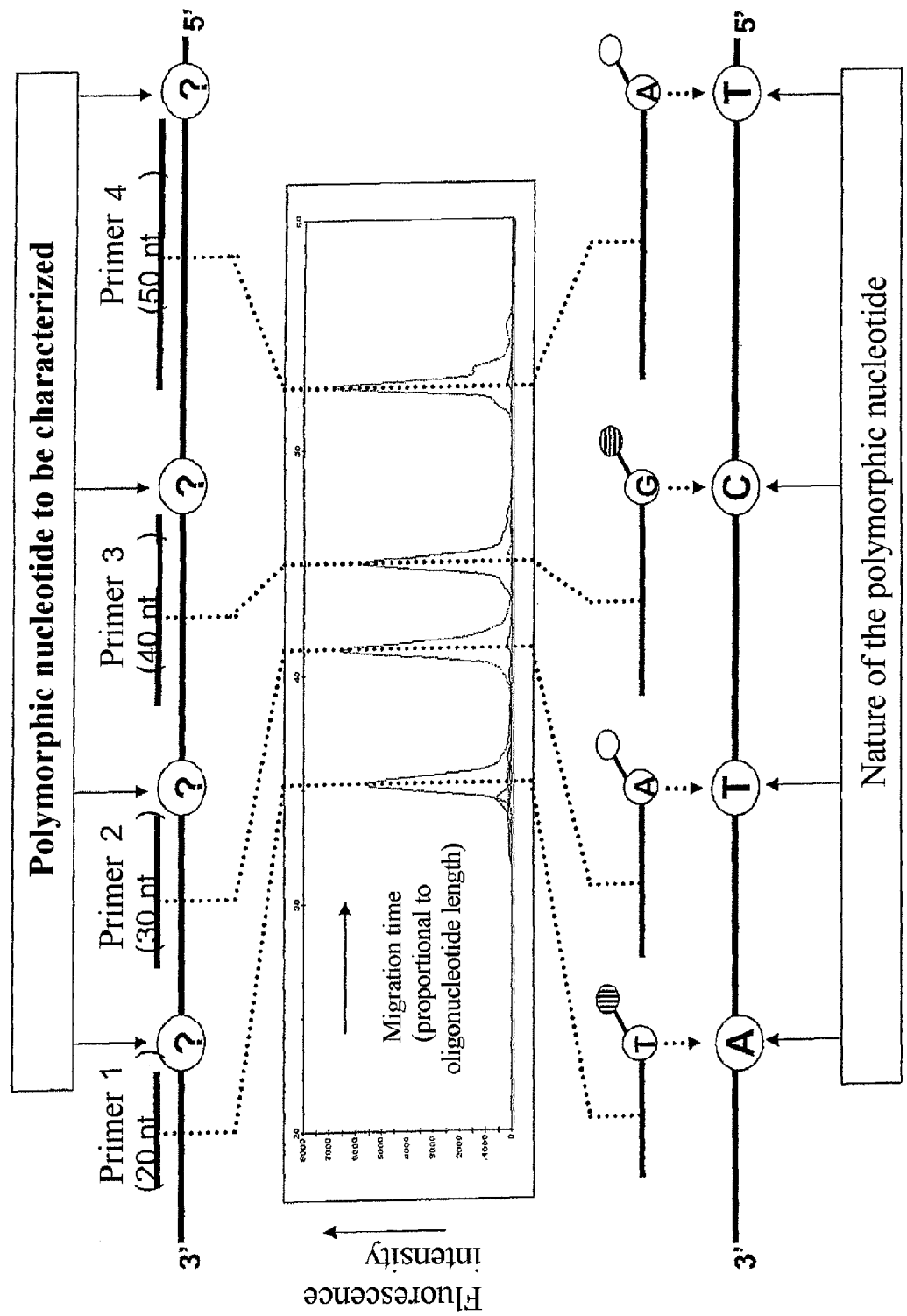

Specific Detection of PVY$^N$ and PVY$^O$ Isolates Using a Fluorescent Nucleotide (ddNTP) Primer Extension Technique After having extracted the nucleic acids from the plant to be tested, an RT-PCR step is carried in a way similar to that described in example 1.4. The amplification product obtained is then purified using a step of filtration on a Sephadex G-50 matrix in order to eliminate the free nucleotides and the components (enzyme, primers, etc.) still present in the sample. The purified PCR product (amplicon) then undergoes an extension step via a cyclic polymerization reaction (10 seconds at 96° C., 5 seconds at 50° C. and 30 seconds at 60° C.) performed 25 times in the presence of the primers that hybridize upstream or downstream of the polymorphic sites to be characterized and a Taq polymerase enzyme in the presence of ddNTP (having a differential fluorescent marking). At the end of this single extension phase, the samples are placed in the presence of one unit of alkaline phosphatase and incubated for one hour at 37° C. in order to limit the disturbance to the reading of the results by free ddNTP. The enzyme then is decontaminated by incubation of the sample for 15 minutes at 75° C. Lastly, the sample is deposited on a polyacrylamide gel and migrates under the effect of an electric field. In order to be able at the end to position the various fluorescent signals recorded during migration, a size marker (standard possessing fluorescent nucleotide fragments of various sizes from 10 to 120 nucleotides) was added to each sample before being deposited on the electrophoresis gel. Polyacrylamide gel migration rate being proportional to molecule size (length), the size marker makes it possible to identify the size of each primer observed during migration. The nature of the fluorescence of these primers makes it possible to identify the nature of the fluorescent ddNTP to which it is linked. This ddNTP fluorescence corresponds to the complementary base of the polymorphic nucleotide initially present on the target molecule present in the sample tested. The general principles of this test are diagrammed in FIGS. 9 and 10.

REFERENCES

Abdelmaksoud, H. M., Gamal Eldin, A. S., 2002. The complète nucleotide sequence of the Potato virus Y strain N-Egypt. Unpublished. Genbank Accession umber: AF522296

Berckx, R., 1967. Methodische untersuchungen über den serologischen nachweis pflanzenpathogener viren mit dem bentonit-flockungstest, den latex-text und dem bariumsulfat test. Phytopathologische Zeitschrift 58, 1-17.

Blanco-Urgoiti, B., Tribodet, M., Leclere, S., Ponz, F., Perez de San Roman, C, Legorburu, F J., Kerlan, C, 1998. Characterization of potato potyvirus Y (PVY) isolâtes from seed potato batches. Situation of the NTN, Wilga and Z isolates. Eur. J. Plant Pathol. 104: 811-819.

Boonham, N., Walsh, K., Preston, S., North, J., Smith, P., Barker, I., 2002. The detection of tuber necrotic isolates of Potato virus Y, and the accurate discrimination of PVY(O), PVY$^N$ and PVY$^C$ strains using RT-PCR. J. Virol. Methods 102(1-2):103-12

Boonham, N., Barker, I., 1998. Strain specific recombinant antibodies to potato virus Y potyvirus. J. Virol. Methods 74(2): 193-9.

Brunt, A. A., Crabtree, K., Dallwitz, M. J., Gibbs, A. J., Watson, L., Zurcher, E. J., 1996. "Plant Viruses Online: Descriptions and Lists from the VIDE Database. Version: 20 Aug. 1996." located at the website biology.anu.edu.au/Groups/MES/vide/.

Chrzanowska, M., 1991. New isolates of the necrotic strain of potato virus Y (PVY$^N$) found recently in Poland. Potato Res. 34:179-182.

De Bokx, J. A., Hutting a, H., 1981. Potato virus Y. CMI/AAB Description of plant viruses No. 242, CMI/AAB, Slough, England, 6 pp.

Dougherty, W. G., Carrington, J. C., 1988. Expression and function of potyviral gene products. Ann. Rev. Phytopathology 26:123-143

Ellis, P., Stace-Smith, R., Bowler, G., Mackenzie, D J., 1996. Production of monoclonal antibodies for détection and identification of strains of potato virus Y. Can. J. Plant Pathol. 18, 64-70.

Fabre, F., Kervarrec, C, Mieuzet, L., Riault, G., Vialatte, A., Jacquot, E., 2003. Improvement of Barley yellow dwarf virus-PAV detection in single aphids using a fluorescent real time RT-PCR. J. Virol. Methods 110(1):51-60

Fakhfakh, H., Vilaine, F., Makni, M., Robaglia, C, 1996. Cell-free cloning and biolistic inoculation of an infectious cDNA of potato virus Y. J. Gen. Virol. 77: 519-523.

Gugerli P., Fries, P., 1983. Characterization of monoclonal antibodies to potato virus Y and their use for virus detection. J. Gen. Virol. 64:2471-2477.

Glais, L., Tribodet, M., Gauthier, J. P., Astier-Manifacier, S., Robaglia, C, Kerlan, C, 1998. RFLP mapping of the whole genome of ten viral isolates representative of different biological groups of potato virus Y. Arch. Virol. 143: 2077-2091.

Glais, L., Kerlan, C, Robaglia, C, 2001. Variability and evolution of potato virus Y, the type species of the potyvirus genus. In Plant Viruses as molecular pathogens. Ed. Jawaid A. Khan and Jeanne Dijkstra, Food Products Press, The Haworth Press, Inc, New York.

Glais, L., Tribodet; M., Kerlan, C, 2002. Genomic variability in Potato potyvirus Y (PVY): evidence that PVY$^{(N)}$W and PVY$^{(NTN)}$ variants are single to multiple recombinants between PVY$^{(O)}$ and PVY$^{(N)}$ isolates. Arch. Virol. 147(2): 363-78.

Glais, L., Colombel, A. S., Tribodet, M., Kerlan, C, 2004. PVY$^N$-605, the reference PVYN isolate, displays a PVY$^{NTN}$ non-recombinant genome. The 12$^{th}$ EAPR virology section meeting, Rennes-France, 2004 Jun. 13-19$^{th}$, abstracts. pp 50

Health, R., Sward, R J., Moran, J. R., Mason, A. J., Hallam, N. D., 1987. Biological characterization of six Australian isolates of potato virus Y and their serological detection by ELISA. Australian Journal of Agricultural Research 38, 395-402.

Jakab, G., Droz, E., Brigneti, G., Baulcombe, D., Malnoe, P., 1997. Infectious in vivo and in vitro transcripts from a full-length cDNA clone of PVY-N605, a Swiss necrotic isolate of potato virus Y. J. Gen. Virol. 78(12):3141-5.

Kerlan, C, Tribodet, M., Glais, L., Guillet, M., 1999. Variability of potato virus Y in potato crops in France. J. Phytopathology 147:643-651.

Le Romancer, M., Kerlan, C, Nedellec, M., 1994. Biological characterization of various geographical isolates of potato virus Y inducing superficial necrosis on potato tubers. Plant Pathol. 43, 138-144.

Maat, D. Z., Hutting a, H., 1987. Serology. In Viruses of potatoes and seed-potato production. Ed. by De Bokx, J. A. and van der Want, J. P. H., Pudoc Wageningen, N L.

Marie-Jeanne Tordo, V., Chachulska, A. M., Fakhfakh, H., Le Romancer, M., Robaglia, C, Astier-Manifacier, S., 1995. Sequence polymorphism in the 5'NTR and in the P1 coding region of potato virus Y genomic RNA. J. Gen. Virol. 76:939-49.

Matousek, J., Ptacek, J., Dedic, P., Schubert, J., 2000. Analysis of variability of P1 gene region of N strain of potato virus Y using temperature-gradient gel electrophoresis and DNA heteroduplex analysis. Acta Virol. 44(1):41-6.

Mc Donald, J. G. and Kristjansson, G. T., 1993. Properties of strains of potato virus YN in North America, Plant Disease, 77(1): 87-89.

Mc Donald, J. G., Singh R. P., 1996. Host range, symptomatology, and serology of isolates of Potato virus Y (PVY) that share properties with both the PVY$^N$ and PVY$^O$ strain groups. American Potato Journal 73:309-315.

Milne, R. G., 1988. The Plant Viruses-4. The filamentous plant viruses, ed. by R. G. Milne, Plenum Press New York & London, 1988.

Moravec, T., Cerovska, N., Boonham, N., 2003. The detection of recombinant, tuber necrosing isolates of Potato virus Y (PVY$^{NTN}$) using a three-primer PCR based in the coat protein gene. J. Virol. Methods 109(1):63-8.

Nie, X., Singh, R. P., 2001. A novel usage of random primers for multiplex RT-PCR detection of virus and viroid in aphids, leaves, and tubers. J. Virol. Methods 91, 37-49.

Nie, X., Singh R. P., 2002. A new approach for the simultaneous differentiation of biological and geographical strains of Potato virus Y by uniplex and multiplex RT-PCR. J. Virol. Methods 104(1):41-54.

Nie, X., Singh, R. P., 2003. Specific differentiation of recombinant PVY$^{(N:O)}$ and PVY$^{(NTN)}$ isolates by multiplex RT-PCR. J. Virol. Methods 113(2):69-77.

Oefiier, P J. 2002. Sequence variation and the biological function of genes: methodological and biological considerations. J Chromatogr B Analyt Technol Biomed Life Sci. 25; 782(1-2):3-25.

Ounouna, H., Kerlan, C, Lafaye P., Loukili M. J., ElGaaied, A. 2002. Production of monoclonal antibodies against synthetic peptides of the N-terminal region of Potato virus Y coat protein and their use in PVY strain differentiation. Plant Pathol. 51: 487-494

Oshima, K., Inoue, A. K., Ishikawa, Y., Shikata, E., Takashi, H., 1990. Production and application of monoclonal antibodies specific to ordinary strain and necrotic strain of potato virus Y. Ann. Phytopathol. Soc. Jpn. 56: 508-514.

Robaglia, C, Durand-Tardif, M., Tronchet, M., Boudazin, G., Astier-Manifacier, S., Casse-Delbart, F., 1989. Nucleotide sequence of potato virus Y (N strain) genomic RNA. J. Gen. Virol. 70:935-947.

Roberts, C. A., Dietzgen, R. G., Heelan, L. A., Maclean, D. J., 2000. Real-time RT-PCR fluorescent detection of tomato spotted wilt virus. J. Virol. Methods 88, 1-8.

Rosner, A., Maslenin, L., 1999. Differentiating PVY$^{NTN}$ by unique single-restriction cleavage of PCR products. Potato Res. 42, 215-221.

Rosner, A., Maslenin, L., 2001. Differentiating PVY$^{(NTN)}$ from PVY$^{(N)}$ by annealing to reference RNA transcripts. J. Virol. Methods. 97(1-2):125-31.

Rosner, A., Maslenin, L., 2003. Tagging of viral RNA transcripts with strain-specific oligonucleotides: characterization and application. J. Virol. Methods. 110(1):105-9.

Sanz, A., Cambra, M., Perez de San Roman, C, Miguet, J. G., Cortés, E., Gorris, M. T., Vela., C, 1990. Preparation of additional monoclonal antibodies for detection and discrimination of potato virus Y isolates infecting potato. Potato Res. 33: 365-375.

Shukla, D. D., Ward, C. W., Brunt, A. A., 1994. The Potyviridae. Cambridge University Press, Cambridge, 516p.

Singh, R. P., Boucher, A., Somerville, T. H., Dhar, A. K., 1993. Selection of monoclonal antibody to detect PVY$^N$ and its use in ELISA and DIBA assays. Can. J. Plant Pathol. 15, 293-300.

Singh, M., Singh, R. P., 1996. Nucleotide sequence and genome organization of a Canadian isolate of the common strain of potato virus Y (PVYO). Can. J. Plant Pathol. 18:209-224.

Sigvald, R., 1984. The relative efficiency of some aphid species as vector of potato virus Y. Potato Res. 27, 285-290.

Smith, K. M., 1931. Composite nature of certain potato viruses of the mosaic group as revealed by the use of plant indicators. Proc. Royal Soc. London, B 109: 251-267.

Szemes, M., Klerks, M. M., van den Heuvel, J. F., Schoen, CD., 2002. Development of a multiplex AmpliDet RNA assay for simultaneous detection and typing of potato virus Y isolates. J. Virol. Methods 100(1-2):83-96.

Talley, J., Warren, F. H. J. B., Torrance, L., Jones, R. A. C. 1980. A simple kit for detection of plant viruses by the latex serological test. Plant Pathol. 29: 77-79.

Thole, V., Dalmay, T., Burgyan, J., Balazs, E., 1993. Cloning and sequencing of Potato virus Y (Hungarian isolate) genomic RNA. Gene 123:149-156.

Walsh, K., North, J., Barker, L, Boonham, N., 2001. Detection of different strains of Potato virus Y and their mixed infections using competitive fluorescent RT-PCR. J. Virol. Methods 91(2):167-73.

Walkey, D. G. A., Webb, M. J. W., 1984. The use of a simple electron microscope serology procedure to observe relationships of seven potyviruses. Phytopathologische Zeitschrift 110: 319-327.

TABLE 2

Raw data and results obtained for mixed PVY$^N$/PVY$^O$ samples

| Y$^N$/Y$^O$ Ratio | PVY quantity N-605 | PVY quantity O-139 | Raw fluorescence FAM | Raw fluorescence Vic | Target fluorescence FAMm | Target fluorescence Vicm | SNP result |
|---|---|---|---|---|---|---|---|
| 1/100 | 1e$^4$ | 1e$^6$ | 0.861 | 1.275 | 0.042 | 0.996 | Y$^O$ |
|  | 1e$^5$ | 1e$^7$ | 0.896 | 1.651 | 0.059 | 1.436 | Y$^O$ |
|  | 1e$^6$ | 1e$^8$ | 1.019 | 1.939 | 0.165 | 1.768 | Y$^O$ |
| 1/10 | 1e$^4$ | 1e$^5$ | 0.887 | 0.825 | 0.084 | 0.466 | Y$^O$ |
|  | 1e$^5$ | 1e$^6$ | 1.103 | 1.276 | 0.272 | 0.986 | Y$^N$/Y$^O$ |
|  | 1e$^6$ | 1e$^7$ | 1.326 | 1.677 | 0.468 | 1.447 | Y$^N$/Y$^O$ |
|  | 1e$^7$ | 1e$^8$ | 1.524 | 1.996 | 0.643 | 1.812 | Y$^N$/Y$^O$ |
| 1/1 | 1e$^4$ | 1e$^4$ | 0.860 | 0.563 | 0.068 | 0.160 | / |
|  | 1e$^5$ | 1e$^5$ | 1.276 | 0.816 | 0.454 | 0.438 | Y$^N$/Y$^O$ |
|  | 1e$^6$ | 1e$^6$ | 1.653 | 1.198 | 0.798 | 0.871 | Y$^N$/Y$^O$ |
|  | 1e$^7$ | 1e$^7$ | 1.850 | 1.601 | 0.970 | 1.335 | Y$^N$/Y$^O$ |
|  | 1e$^8$ | 1e$^8$ | 2.119 | 1.846 | 1.216 | 1.610 | Y$^N$/Y$^O$ |
| 10/1 | 1e$^5$ | 1e$^4$ | 1.354 | 0.542 | 0.540 | 0.113 | Y$^N$ |
|  | 1e$^6$ | 1e$^5$ | 1.729 | 0.724 | 0.889 | 0.310 | Y$^N$/Y$^O$ |
|  | 1e$^7$ | 1e$^6$ | 2.055 | 0.911 | 1.191 | 0.515 | Y$^N$/Y$^O$ |
|  | 1e$^8$ | 1e$^7$ | 2.322 | 1.384 | 1.427 | 1.059 | Y$^N$/Y$^O$ |
| 100/1 | 1e$^6$ | 1e$^4$ | 1.697 | 0.551 | 0.865 | 0.108 | Y$^N$ |
|  | 1e$^7$ | 1e$^5$ | 2.065 | 0.545 | 1.215 | 0.085 | Y$^N$ |
|  | 1e$^8$ | 1e$^6$ | 2.230 | 0.630 | 1.370 | 0.178 | Y$^N$ |
| NTC | / | / | 0.754 | 0.427 | −0.027 | 0.004 | / |
| Pure PVY$^N$ | 1e$^6$ | / | 1.753 | 0.451 | 0.912 | −0.020 | Y$^N$ |
| Pure PVY$^O$ | / | 1e$^6$ | 0.816 | 1.276 | −0.002 | 0.998 | Y$^O$ |

$^a$: the detection threshold using target fluorescence data was set at 0.02. The FAMm and Vicm values in bold correspond to the detection of PVY$^N$ and PVY$^O$.

TABLE 3

Comparison between the serological and biological results and the inventive method for detecting PVY isolates

| Group or variant | Isolate | ELISA Y$^N$ | ELISA Y$^{O/C}$ | TVN$^a$ | Target fluorescence FAM | Target fluorescence Vic | SNP result |
|---|---|---|---|---|---|---|---|
| N | 605 | + | − | + | 0.282 | 0.006 | Y$^N$ |
|  | C3VN | + | − | + | 0.270 | 0.008 | Y$^N$ |
|  | Irl | + | − | + | 0.296 | 0.009 | Y$^N$ |
|  | 607 | + | − | + | 0.212 | −0.003 | Y$^N$ |
|  | P21 | + | − | + | 0.286 | 0.040 | Y$^N$ |
|  | B203 | + | − | + | 0.319 | 0.077 | Y$^N$ |
|  | B8 | + | − | + | 0.408 | −0.004 | Y$^N$ |
|  | B7 | + | − | + | 0.409 | −0.006 | Y$^N$ |
|  | B4 | + | − | + | 0.444 | −0.016 | Y$^N$ |
|  | Sp20 | + | − | + | 0.565 | −0.009 | Y$^N$ |
|  | TVNQ | + | − | + | 0.584 | −0.010 | Y$^N$ |
|  | Sp125 | + | − | + | 0.875 | −0.018 | Y$^N$ |
| O | 139 | − | + | − | −0.001 | 0.612 | Y$^O$ |
|  | Irl | − | + | − | −0.021 | 0.612 | Y$^O$ |
|  | Sc | − | + | − | −0.004 | 0.370 | Y$^O$ |
|  | N1702 | − | + | − | −0.009 | 0.365 | Y$^O$ |
|  | Lw | − | + | − | 0.006 | 0.654 | Y$^O$ |
|  | B18 | − | + | − | −0.003 | 0.626 | Y$^O$ |
| N-W | i-P | − | + | + | 0.491 | −0.009 | Y$^N$ |
|  | N242 | − | + | + | 0.483 | −0.005 | Y$^N$ |
|  | B11 | − | + | + | 0.509 | −0.009 | Y$^N$ |
|  | Sp17 | − | + | + | 0.537 | 0.024 | Y$^N$ |
|  | B15 | − | + | + | 0.590 | −0.014 | Y$^N$ |
|  | N5 | − | + | + | 0.594 | −0.011 | Y$^N$ |
|  | N362 | − | + | + | 0.616 | −0.009 | Y$^N$ |
|  | N341 | − | + | + | 0.685 | −0.020 | Y$^N$ |
|  | N324 | − | + | + | 0.664 | −0.015 | Y$^N$ |
|  | N15 | − | + | + | 0.374 | −0.007 | Y$^N$ |
|  | N12 | − | + | + | 0.515 | −0.012 | Y$^N$ |
|  | N10 | − | + | + | 0.613 | −0.009 | Y$^N$ |
| NIN | Lb | + | − | + | 0.576 | −0.012 | Y$^N$ |
|  | FrOrl | + | − | + | 0.748 | 0.042 | Y$^N$ |
|  | H | + | − | + | 0.692 | −0.011 | Y$^N$ |
|  | Sp47 | + | − | + | 0.569 | 0.003 | Y$^N$ |
|  | Dk | + | − | + | 0.784 | 0.019 | Y$^N$ |
|  | Lx2 | + | − | + | 0.795 | −0.006 | Y$^N$ |
|  | CzLuk1 | + | − | + | 0.558 | −0.021 | Y$^N$ |
|  | B9 | + | − | + | 0.668 | 0.049 | Y$^N$ |
|  | B6 | + | − | + | 0.682 | −0.028 | Y$^N$ |
|  | N18 | + | − | + | 0.629 | −0.022 | Y$^N$ |
|  | N4 | + | − | + | 0.804 | −0.015 | Y$^N$ |
|  | May2 | + | − | + | 0.756 | −0.017 | Y$^N$ |

$^a$: Symptoms of tobacco vein necrosis (*N. tabacum* cv Xanthi)

The invention claimed is:

1. A method for detecting the presence or absence of PVY strains responsible for veinal, foliar or tubercular necrosis in plants of the Solanaceae family, characterized such that it comprises the following steps:
   a) extraction of nucleic acids from a plant sample,
   b) RT-PCR amplification of a region of PVY viral RNA comprising:
      i) codon 738 of SEQ ID NO: 1 or 3, corresponding to amino acid 400 of the HC-Pro protein of SEQ ID NO: 2 or 4, respectively; and
      ii) codon 757 of SEQ ID NO: 1 or 3, corresponding to amino acid 419 of the HC-Pro protein of SEQ ID NO: 2 or 4, respectively,
   c) detecting the presence or absence of each of the following:
      α) a codon encoding the K amino acid at position 400 of the HC-Pro protein; and
      β) a codon encoding the E amino acid at position 419 of the HC-Pro protein set forth in SEQ ID NO: 2 or 4, the detection of said codons set forth in α) and β) being an indication of a virulent strain of PVY capable of causing necrosis in plants of the Solanaceae family.

2. The method according to claim 1, wherein step c) comprises the detection on the cDNA obtained in step b) of the presence or absence of each of the following: (α) a codon encoding amino acid K at position 400; and (β) a codon encoding amino acid E at position 419, of the HC-Pro protein set forth in SEQ ID NO: 2 or 4 by means of i) at least one labeled probe specific to a polymorphism on codon 738 of SEQ ID NO: 1 or 3 and ii) at least one labeled probe specific to a polymorphism on codon 757 of SEQ ID NO: 1 or 3, said probes i) and ii) carrying labels that emit a different fluorescent signal, wherein the presence of said codon encoding amino acid K at position 400 and said codon encoding amino acid E at position 419 of the HC-Pro protein set forth in SEQ ID NO: 2 or 4 is an indication of the presence of a virulent strain of PVY responsible for necrosis in plants of the Solanaceae family.

3. The method according to claim 1, wherein step c) comprises the detection on the cDNA obtained in step b) of the presence or absence of each of the following: (α) a codon encoding amino acid K at position 400; and (β) a codon encoding amino acid E at position 419, of the HC-Pro protein set forth in SEQ ID NO: 2 or 4 by means of an oligonucleotide primer extension reaction using ddNTP labeled differentially and i) at least one unlabeled primer that hybridizes specifically upstream or downstream (±1 nt) of polymorphic nucleotide 2213 of codon 738 of SEQ ID NO: 1 or 3; and ii) at least one unlabeled primer that hybridizes specifically upstream or downstream (±1 nt) of polymorphic nucleotide 2271 of codon 757 of SEQ ID NO: 1 or 3, the presence of at least one of said codon encoding amino acid K at position 400 and said codon encoding amino acid E at position 419 of the HC-Pro protein set forth in SEQ ID NO: 2 or 4 being an indication of the presence of a virulent strain of PVY responsible for necrosis in plants of the Solanaceae family.

4. The method according to claim 1, wherein said method is implemented in the potato.

5. The method according to claim 4, wherein the detection in step c) of said codon encoding amino acid K at position 400 and said codon encoding amino acid E at position 419 of the HC-Pro protein set forth in SEQ ID NO: 2 or 4 is an indication that the potato plant is contaminated with one or more strains capable of inducing tubercular necrosis.

6. The method according to claim 2, wherein at least one of said at least one probe i) used in step c) hybridizes specifically with the target sequence when codon 738 is AAA with polymorphism $A_{2213}$.

7. The method according to claim 6, wherein said at least one probe i) contains from 14 to 40, 15 to 25, 18 to 22 or 20 consecutive nucleotides of a sequence capable of hybridizing with sequence SEQ ID NO 5 (FIG. 1) and comprising the nucleotide in position 2213, in particular SEQ ID No 7: ctcaaatgaaaatattctac.

8. The method according to claim 6, wherein in addition a control probe i) is used in step c), in particular a probe that hybridizes specifically with the target sequence when codon 738 is AGA with polymorphism $G_{2213}$.

9. The method according to claim 8, wherein said control probe i) contains from 14 to 40, 15 to 25, 18 to 22 or 20 consecutive nucleotides of a sequence capable of hybridizing with sequence SEQ ID No 6 (FIG. 1) and comprising the nucleotide in position 2213, in particular SEQ ID No 8: ctcaaatgagaatattcta.

10. The method according to claim 8, wherein probe i) and control probe i) are labeled differently.

11. The method according to claim 2, wherein at least one of said at least one probe ii) used in step c) hybridizes specifically with the target sequence when codon 757 is GAA with polymorphism $A_{2271}$.

12. The method according to claim 11, wherein said at least one probe ii) contains from 14 to 40, 15 to 25, 18 to 22 or 20 consecutive nucleotides of a sequence hybridizing with sequence SEQ ID NO 5 (FIG. 1) and comprising the nucleotide in position 2271, in particular with SEQ: 5'cgatcacga aacgcagaca-3' (SEQ ID No 9) or 5'-atcacgaaacgcagaca-3' (SEQ ID No 20).

13. The method according to claim 11, wherein in addition a control probe ii) is used in step c), in particular a probe that hybridizes specifically with the target sequence when codon 757 is GAC with polymorphism $C_{2271}$.

14. The method according to claim 13, wherein said control probe ii) contains from 14 to 40, 15 to 25, 18 to 22 or 20 consecutive nucleotides of a sequence hybridizing with sequence SEQ ID No 6 (FIG. 1) and comprising the nucleotide in position 2271, in particular with SEQ ID No 10: 5'-accatgacactcaaa-3' or with SEQ ID No 21: 5'-tgaccatga cactcaa-3'.

15. The method according to claim 13, wherein probe ii) and control probe ii) are labeled differently.

16. The method according to claim 6, wherein the probes contain a fluorescent label (reporter) and a molecule that captures the signal when near the fluorescent label (quencher).

17. The method according to claim 3, wherein at least one of said at least one primer i) used in step c) hybridizes specifically with the target sequence when codon 738 is AAA with polymorphism $A_{2213}$.

18. The method according to claim 17, wherein said at least one primer i) contains from 10 to 120 or 20 consecutive nucleotides of a sequence hybridizing with sequence SEQ ID NO 5 (FIG. 1) and comprising the nucleotide in position 2212 or 2214.

19. The method according to claim 3, wherein at least one of said at least one primer ii) used in step c) hybridizes specifically with the target sequence when codon 757 is GAA with polymorphism $A_{2271}$.

20. The method according to claim 19, wherein said at least one primer ii) contains from 10 to 120 or 20 consecutive nucleotides of a sequence hybridizing with sequence SEQ ID NO 5 (FIG. 1) and comprising the nucleotide in position 2270 or 2272.

21. The method according to claim 1, wherein in step b), reverse transcription is carried out with at least two pairs of sense and antisense primers.

22. The method according to claim 21, wherein reverse transcription is carried out with at least two or four pairs of sense and antisense primers, more particularly at least a first pair enabling the amplification of nucleotide sequences including codons 738 and 757 of $PVY^N$ strains, at least a second pair enabling the amplification of nucleotide sequences including codons 738 and 757 of $PVY^O$ strains.

23. The method according to claim 22, wherein the first pair of primers (FpN and RpN) preferably comprises an FpN sense primer and an RpN antisense primer that can contain a sequence of 20 to 40 consecutive nucleotides of a sequence that hybridizes with sequence SEQ ID No 1 or 5.

24. The method according to claim 22, wherein the FpN sense primer is located upstream of polymorphic codon 738 and the RpN primer is located downstream of polymorphic codon 757.

25. The method according to claim 22, wherein two first pairs can be used as follows:
FpN1 upstream of codon 738
RpN1 downstream of codon 738
FpN2 upstream of codon 757
RpN2 downstream of codon 757.

26. The method according to claim 22, wherein the second pair of primers (FpO and RpO) preferably comprises an FpO sense primer and an RpO antisense primer that can contain a sequence of 20 to 40 consecutive nucleotides of a sequence that hybridizes with sequence SEQ ID NO 3 or 6.

27. The method according to claim 26, wherein the FpO sense primer is located upstream of polymorphic codon 738 and the RpO primer is located downstream of polymorphic codon 757.

28. The method according to claim 26, wherein two second pairs are used as follows:
FpO1 upstream of codon 738
RpO1 downstream of codon 738
FpO2 upstream of codon 757
RpO2 downstream of codon 757.

29. The method according to claim 22, wherein the two pairs of primers are selected among:

```
Sense primers for YN:
SEQ ID No 22 F1: 5'-ATGATGCAGAACTGCCTAGAATACTAGT-3'

Antisense primers for YN:
SEQ ID No 28 R1: 5'-GTGAGCCAAACGAGTCAACTACAT-3'

Sense primers for YO:
SEQ ID No 25 F1: 5'-GCAGAGCTGCCTAGTTTATTGGTT-3'

Antisense primers for YO:
SEQ ID No 31 R1: 5'-GCCAAATGAGTCAACCACATGA-3'.
```

30. The method according to claim 3, wherein the detection and identification of the polymorphic nucleotide in position 2213 is carried out with sense primer selected among:

```
SEQ ID No 38 Oli5:
5'-CCAACCATGATGGATCTGGCGACAACTTGTGCTCAAATGA-3'
``` and an antisense primer selected among:

```
SEQ ID No 43 Oli10:
5'-TCTAGGCAGTTCTGCATCATGAACATCAGGGTAGAATATT-3'.
```

31. The method according to claim 3, wherein the detection and identification of the polymorphic nucleotide in position 2271 are carried out with a sense primer selected among:

```
SEQ ID No 48 Oli15:
5'-ATGCAGAACTGCCTAGAATATTGGTTGACCATGA-3'
``` and an antisense primer selected among:

```
SEQ ID No 53 Oli20:
5'-AGCCAAACGAGTCAACTACATGGCATGTCTGCGT-3'.
```

32. A sanitary method for selecting seedlings belonging to the Solanaceae family contaminated by PVY strains responsible for veinal, foliar or tubercular necrosis, in particular tubercular necrosis in the potato, comprising the systematic implementation of the detection method according to claim 1 on seeds, seedlings and/or plants to be cultivated and then proceeding with the destruction or quarantine of said seeds, seedlings or plants contaminated with a strain exhibiting the amino acid K at position 400 and amino acid E at position 419 of the HC-Pro protein set forth in SEQ ID NO: 2 or 4.

33. A kit for detecting the presence or absence of PVY viruses responsible for veinal, foliar or tubercular necrosis in plants of the Solanaceae family, comprising:
    at least a first pair of primers enabling the amplification of nucleotide sequences including codons 738 and 757 of SEQ ID NO: 1, at least a second pair of primers enabling the amplification of nucleotide sequences including codons 738 and 757 of SEQ ED NO: 3,
    at least one labeled probe i) specific of a polymorphism on codon 738 of SEQ ID NO: 1 or 3, and at least one labeled probe ii) specific for a polymorphism on codon 757 of SEQ ID NO: 1 or 3, said probes i) and ii) being such as described according to claim 2, and carrying labels that emit different fluorescent signals.

34. The detection kit according to claim 33 comprising in addition, control probes i) as defined as aerobe that hybridizes specifically with the target sequence when codon 738 is AGA with polymorphism $G_{2213}$ and control probe ii) as defined as a probe that hybridizes specifically with the target sequence when codon 757 is GAC with polymorphism $C_{2271}$, respectively, probes i) and controls probe i) being labeled with different fluorescent labels, probes ii) and controls probe ii) being labeled with different fluorescent labels.

* * * * *

UNITED STATES PATENT AND TRADEMARK OFFICE
CERTIFICATE OF CORRECTION

| | | |
|---|---|---|
| PATENT NO. | : 8,063,270 B2 | Page 1 of 1 |
| APPLICATION NO. | : 11/910948 | |
| DATED | : November 22, 2011 | |
| INVENTOR(S) | : Jacquot et al. | |

It is certified that error appears in the above-identified patent and that said Letters Patent is hereby corrected as shown below:

On the face of the Patent, on line 4 of the Abstract:

"inducting" should read --indicating--;

Column 86, claim 34, lines 23 and 24, both occurrences, "controls probe" should read --control probe--.

Signed and Sealed this
Fourteenth Day of February, 2012

David J. Kappos
*Director of the United States Patent and Trademark Office*

SEQUENCE LISTING

```
<160> NUMBER OF SEQ ID NOS: 53

<210> SEQ ID NO 1
<211> LENGTH: 9701
<212> TYPE: DNA
<213> ORGANISM: Potato virus
<220> FEATURE:
<223> OTHER INFORMATION: PVYN-605 sequence

<400> SEQUENCE: 1
aaattaaaac aactcaatac aacataagaa aatcaacgca aaaacactca caaaagcttt      60
caactctaat tcaaacaatt tgttaagttt caatttcgat cttcatcaaa caaactcttt     120
caatttcagt gtaagctatc gtaattcagt aagttatttc aaactctcgt aaattgcaga     180
agatcatcca tggcaattta cacatcaaca atccagtttg gttccattga atgcaaactt     240
ccatactcac ccgctccttt tgggctagtt gcggggaaac gagaagtttc aaccaccact     300
gaccccttcg caagtttgga gatgcagctc agtgcgcgat tacgaaggca ggagtttgca     360
actattcgaa catccaagaa tggtacttgc atgtatcgat acaagactga tgtccagatt     420
```

```
gcgcgcattc aaaagaagcg cgaggaaaga gaaagagagg aatataattt ccaaatggct    480
gcgtcaagtg ttgtgtcgaa gatcactatt gctggtggag agccaccttc aaaacttgaa    540
tcacaagtgc ggagggggtgt catccacaca actccaagga tgcgcacagc aaaaacatat   600
cacacgccaa agttgacaga gggacaaatg aaccacctta tcaagcaggt gaagcaaatt    660
atgtcaacca aggagggtc tgtccaactg attagcaaga aaagtaccca tgttcactat     720
aaagaagttt tgggatcaca tcgcgcagtt gtttgcactg cacatatgag aggtttacga    780
aagagagtgg actttcggtg tgataaatgg accgttgtgc gtctacagca tctcgccagg    840
acggacaagt ggactaacca agttcgtgct actgatctac gcaagggcga tagtggagtt    900
atattgagta atactaatct caaaggaaac tttgggagaa gctcggaggg cctattcata    960
gtgcgtgggt cgcacgaagg aaaaatctat gatgcacgtt ccaaggttac tcaagggggtt 1020
atggattcaa tggttcagtt ctcaagcgct gaaagctttt ggaagggatt ggacggcaat   1080
tgggcacaaa tgagatatcc tacagatcat acatgtgtgg caggcttacc agttgaagac  1140
tgtggcagag ttgcagcgat aatgacacac agtatttac cgtgctataa gattacctgc    1200
cctacctgtg cccaacaata tgccaacttg ccagccagtg acttacttaa gatattacac  1260
aagcacgcaa gtgatggtct aaatcgattg ggggcagaca agatcgcctt tgtgcatgtc  1320
aaaaagttct tgacaatctt agagcactta actgaaccgg ttgatctgag tctagaaatt  1380
ttcaatgaag tattcaagtc tatagggggag aagcaacaat ccctttcaa aaacctgaat   1440
attctgaata atttctttt gaaggaaag gaaaatacag ctcgtgaatg gcaggtggct     1500
caattaagct tacttgaatt ggcaagattc caaaagaaca gaacggataa tatcaagaaa  1560
ggagacatct cgttctttag aataaaacta tctgccaaag caaattggaa cttgtatctg  1620
tcatgtgata accagctgga taagaatgca agcttcctgt ggggacagag ggaatatcat  1680
gctaagcgat ttttctcgaa ctatttcgag gaaattgatc cagcgaaggg ctattcagca  1740
tacgaaaatc gtttgcatcc gaatgggaca agaaaacttg caattggaaaa cctaattgta  1800
ccacttgatc tggctgagtt taggcggaag atgaaaggtg attataaaag acagccaggg  1860
gtgagtaaga agtgcacgag ctcgaaggat ggaaactacg tgtatccctg ttgttgcact  1920
acacttgatg atggctcagc tgttgaatca acatttttacc cgccaactaa gaagcacctc  1980
gtaataggta atagtggcga ccaaaagtat gttgacttac caaaagggaa ttctgagatg  2040
ttatatattg ccaggcaagg cttctgttac attaacattt tcctcgcgat gttgattaac  2100
attagtgagg aagatgcaaa ggatttcact aagaaggttc gtgacatgtg tgtgccaaag  2160
cttgaaccct ggccaaccat gatggatctg gctacaactt gtgctcaaat gaaaatattc  2220
taccctgatg ttcatgatgc agaactgcct agaatactag tcgatcacga aacgcagaca  2280
tgccatgtag ttgactcgtt tggctcacaa acaactgggt atcatatttt gaaagcatct  2340
agcgtgtccc aacttatttt gtttgctaat gatgagttgg agtctgacat taagcactat  2400
agagttggtg gtattcctgg agcatgccct gagcttgggt ccacaatatc accttttaga  2460
gaaggaggaa tcataatgtc tgagtcagca gcgctaaaac tgctcctaaa gggaattttt  2520
aggcccaaag tgatgaagca attgctactg gatgaaccat atttgctcat tttatcgata  2580
ttatctcctg gtatacttat ggctatgtac aacaatggga tatttgagtt agcggtgaag  2640
ttgtggatca atgagaaaca atctatagcc atgatagcat cgttattgtc cgccttggct  2700
ttacgagtgt cagcagcaga aacactcgtt gcacagagga ttataattga cacggcagca  2760
acagatcttc tcgatgctac gtgtgatgga ttcaattaa atctgacata tcccactgca   2820
```

```
ctcatggtgt tgcaagttgt taagaacaga aatgaatgtg atgatacgtt gtttaaagca   2880 ggttttttcac attacaacat gagtgtcgtg cagattatgg aaaaaaatta tctaagcctc   2940
ttgggcgatg cctggaaaga tttaacctgg cgagaaaaat tatccgcaac atggcactca   3000
tacaaagcaa agcgctctat cactcagttc ataaaaccca taggcaaagc agatttaaaa   3060
gggttgtaca acatatcacc gcaagcattc ttgggtcagg gcgtacagag agtcaaaggc   3120
accgcctcag ggttgaatga gcgactcaat aattatatca atactaagtg tgtaaatatt   3180
tcatcctttt tcattcgtag aattttccgg cgcttgccaa cttttgtaac tttcattaat   3240
tcattattag ttattagtat gctaactagt gtagtagcag tgtgtcaagc ataattcta    3300 gatcaaagga agtatagaaa agaaattgag ttgatgcaga ttgagaagaa tgaaattgtt   3360
tgtatggagt tgtatgcgag tctgcagcgc aaacttgagc gtgaattcac atgggatgaa   3420
tatatggaat attgaaatc tgtgaatccc cagatagttc aattcgcgca agctcaaatg    3480
gaagaatata atgtgcgaca tcagcgctcc acaccaggtg ttaagaattt agagcaggtg   3540
gtagcattta aactctaat tatcatgatg tttgatgctg aaaggagcga ctgtgtattc    3600
aagactctca acaaattcaa aggcatcgtt tcttcaatgg atcatgaagt taaacaccag   3660
tccttggatg atgtaatcaa gaatttcgat gaaaggaacg aagttattga ttttgagcta   3720
aatgaggata caattaaaac atcatcagtg ttggacacga agtttagcga ctggtgggat   3780
cggcaaatcc aaatgggaca cacacttccc cattatagaa ctgagggaca cttcatggaa   3840
ttcacaaggg caactgctgt acaagtggcc aacgacatcg cgcatagtga gcacctagac   3900
tttctagtga ggggagctgt tgggtctgga aaatctactg gactgcctgt ccatctcagt   3960
gcagctggat ccgtgctttt gatagaacca actcgaccac ttgcagaaaa cgtgttcaag   4020
caattatcca gtgaaccgtt tttcaagaag ccaacactgc gcatgcgagg aaatagtgtg   4080
tttggttcct ctccaatctc catcatgact agcggctttg cgttcactta ctatgctaat   4140
aatcgctctc agctaactca gtttaatttc ataattttg atgaatgtca tgttttagat    4200
ccttctgcaa tggcatttcg tagcttgtta agtgtgtatc accaaacatg caaagtgtta   4260
aaggtgtcag ccactccagt gggaagggag gtcgagttca acacaacaa accagttaaa    4320 ttggtggttg aggatacact ttcattccaa tcttttgttg atgcgcaagg ctcaaaaacc   4380
aatgccgacg ttgttcagca tggttcgaac atactcgtgt atgtgtcgag ttacaatgaa   4440
gtggatacat tagccaagct tctaacagat aggaatatgg tagtctcaaa agttgatggc   4500
agaacaatga agcacggatg cttagaaatt gtaacgaaag ggactagtgc aaagccacat   4560
tttgtcgtag caaccaacat tattgaaaat ggagtaactt tagatataga tgtagttgta   4620
gattttggac ttaaagtctc accgtttta gatattgaca ataggagcat tgcatacaat    4680
aagattagtg ttagctatgg agaaagaatt cagaggttgg gccgtgttgg gcgctttaag   4740
aagggagtgg cattgcgtat tggacacacc gaaaagggaa ttattgagat tccaagtatg   4800
attgctagtg aagctgcgct tgcgtgcttt gcatacaatt tgccagtaat gacaggggggt   4860 gtttcaacta gcctcattgg caattgtact gttcgtcaag ttaaaactat gcaacaattt   4920
gagctgagtc cattctttat acaaaatttt gttgcccatg atggatcaat gcatcctgtc   4980
atacatgaca ttcttaagaa gtataaactg cgagattgta tgacgccctt gtgtgatcaa   5040 tccataccttt acagagcctc aagcacttgg ttgtctgtta gtgagtacga acgactcgga   5100
gtggttttgg acattccaaa acagatcaag attgcattcc acatcaagga catccctcct   5160
aagttgcatg aaatgctttg ggaaacagtt atcaaatata aggatgtttg tttgtttcca   5220
```

```
agtattcggg cttcatccat tagcaaaatt gcatacacac tgcgcactga tcttttgca      5280 attcccagaa ccctaattct agttgaaaga ttgatcgagg aggaacgagt gaaacagagt    5340
caattcagaa gtctcattga tgaaggatgc tcaagcatgt tttcaattgt taatttaaca   5400
aacactctta gagctagata tgcaaaggat tacactgcag aaaacataca gaagctcgag   5460
aaagtgagaa gtcagttaaa ggagttctca aatttaaatg gctctgcatg tgaggagaac   5520
ttaatgaaga ggtatgaatc tctacagttt gtgcatcatc aagcaacaac ttcactcgca   5580
aaggatttga agttgaaagg agtttggaag aagtcattag ttgtgcagga cttactcata   5640
gcgggtgccg ttgctattgg tggaataggg ctcatctata gttggtttac tcaatcagtt   5700
gaaactgtgt ctcaccaggg caagaacaaa tccaaaagaa ttcaagcatt gaagtttcga   5760
cacgcccgcg ataagagggc tggctttgaa attgataaca atgatgatac aatagaggaa   5820
ttctttggat ctgcatacag gaagaaggga aaggtaaagg caccactgt tggtatgggc    5880 aagtcaagca ggaggtttgt taatatgtat ggatttgacc caacagaata ttcattcatc   5940
cagttcgttg atccgctcac tggagctcaa attgaagaga cgtctatgc tgatattaga    6000 gacatccaag agcgctttag tgatgtccgc aagaaaatgg tagaggatga tgaaatcgaa   6060
ttgcaagcat tgggcagcaa cacaaccatt catgcttact tcaggaaaga ttggtctgac   6120
aaggctctaa aaattgattt gatgccacac aacccactca aaatctgtga taatcgaat    6180 ggcattgcta agtttcctga agagaacttt gagttgaggc aaactgggcc agcaatagag   6240
gttgatgtga aagacattcc aaaacaggaa gtggagcatg aagccaaatc actcatgaga   6300
ggtttaaggg atttcaatcc aattgctcaa acagtttgca gagtaaaagt gtctgttgaa   6360
tatggaacgt ctgaaatgta tgggttcggt tttggtgcgt atattatagt aaaccaccat   6420
ctattcaaga gcttcaatgg atccatggaa gtgcgatcaa tgcatggaac attcagagtg   6480
aagaatttgc atagcttgag cgttttaccg atcaaaggca gagacattat catcataaag   6540
atgccaaagg atttccctgt tttcccacaa aaactgcact tccgagctcc agtgcagaat   6600
gagaggattt gtttggttgg aactaatttt caagaaaaac atgcatcatc aatcatcaca   6660
gaaacgagta ctacatacaa tgtaccgggc agcacttttt ggaagcattg gattgaaaca   6720
aatgatgggc attgtggatt accagtagtg agtacagctg atggatgtct agttggaata   6780
cacagcttgg cgaataatgt gcaaaccacg aattattatt cagcctttga tgaggatttt   6840
gaaagtaagt atctccgaac taatgagcat aatgagtgga ccaaatcgtg ggtatataac   6900
ccagatactg tgttgtgggg tccattgaag ctcaaggaga gtaccctaa aggcctgttt    6960 aagacaacaa aacttgtaca ggattaatt gatcatgatg ttgttgtaga gcaagctaaa   7020
cattctgcgt ggatgtatga ggctctaaca gggaatttgc aagctgtggc gacaatgaag   7080
agtcagctag tgacaaagca cgtggtcaaa ggggagtgtc ggcacttcaa agagttctta   7140
actgtggatt cggaagcaga agctttcttc aggcctttga tggatgctta tgggaagagc   7200
ttgttaaata gagaagcata tataaaggac ataatgaaat actcaaagcc tattgatgtt   7260
ggaatagtag actgtgatgc ttttgaagag gctatcaata gggttatcat ttatctgcaa   7320
gtgcatggct tccagaaatg caattacatc accgatgagc aggaaatttt caaagctctc   7380
aatatgaaag ctgctgtcgg agctatgtat ggaggcaaga gaaagactac ttcgagcat    7440 tttactgagg cggataaaga ggaaattgtt atgcaaagtt gctttcgatt gtacaagggc   7500
tcgcttggca tatggaatgg atcattgaaa gcagaacttc ggtgcaaaga gaagatactc   7560
gcaaataaga caaggacatt cactgctgca cctttagata ctctactggg tggaaaggtg   7620
```

```
tgcgttgatg attttaataa tcaattctac tcaaagaaca ttgaatgctg ctggactgtt     7680
ggaatgacta agttttatgg aggttgggac aaattgcttc ggcgtctacc tgaaaattgg     7740
gtgtactgcg atgccgatgg ttcacaattc gatagttcac tcaccccata cctaattaat     7800
gctgttctca tcatcagaag cacatacatg gaagattggg acttggggtt gcaaatgttg     7860
cgcaatttgt acacagaaat aatttacaca ccaatctcaa ctccagatgg aacaattgtc     7920
aagaagttta gaggtaataa tagcggtcaa ccttctaccg ttgtggataa ttctctcatg     7980
gttgtccttg ctatgcatta cgctctcatt aaggagtgcg ttgagtttga agaaatcgac     8040
agcacgtgtg tattctttgt taatggtgat gacttattga ttgctgtgaa tccggagaaa     8100
gagagcattc tcgatagaat gtcacaacat ttctcagatc ttggttttgaa ctatgatttt     8160
tcgtcgagaa caagaaggaa ggaggaattg tggttcatgt cccatagagg cctgctaatc     8220
gaggatatgt acgtgccaaa gcttgaagaa gagagaattg tatccattct gcaatgggat     8280
agagctgatc tgccagagca cagattagaa gcgatttgtg cagcaatgat agaatcctgg     8340
ggttattttg agttaacgca ccaaatcagg agattctact catggttgtt gcaacagcaa     8400
ccttttttcaa cgatagcaca ggaaggaaaa gctccataca tagcgagcat ggcattgaag     8460
aagctgtaca tgaataggac agtagatgag gaggaactga aggctttcac tgaaatgatg     8520
gttgccttgg atgatgaatt tgagtgcgat acttatgaag tgcaccatca aggaaatgac     8580
acaatcgatg caggaggaag cactaaaaag gatgcaaaac aagagcaagg tagcattcaa     8640
ccaaatctca acaaggaaaa ggaaaaggac gtgaatgttg aacatctgg aactcatact     8700
gtgccacgaa ttaaagctat cacgtccaaa atgaaaatgc ccaagagtaa aggtgcaact     8760
gtactaaatt tggaacactt actcgagtat gctccacagc aaattgacat ctcaaatact     8820
cgagcaactc aatcacagtt tgatacgtgg tatgaagcag tacaacttgc atacgacata     8880
ggagaaactg aaatgccaac tgtgatgaat gggcttatgg tttggtgcat gaaaatgga     8940
acctcgccaa acatcaacgg agtttgggtt atgatggatg gaaatgaaca agtcgaatac     9000
ccactgaaac caatcgttga gaatgcaaaa ccaacactta gcaaatcat ggcacatttc     9060
tcagatgttg cagaagcgta tatagaaatg cgcaacaaaa aggaaccata tatgccacga     9120
tatggtttag ttcgtaatct gcgcgatgga agtttggctc gctatgcttt tgactttttat    9180
gaagttacat cacggacacc agtgagggct agagaggcac acattcaaat gaaggccgca    9240
gctttaaaat cagctcaatc tcgactttttc ggattggatg gtggcattag tacacaagag    9300
gaaaacacag agaggcacac caccgaggat gtttctccaa gtatgcatac tctacttgga    9360
gtgaagaaca tgtgattgta gtgtctttcc ggacgatata tagatattta tgtttgcagt    9420
aagtattttg gcttttcctg tactacttt atcgcaatta ataatcgttt gaatattact     9480
ggcagatagg ggtggtatag cgattccgtc gttgtagtga ccttagctgt cgtttctgta    9540
ttattatgtt tgtataaaag tgccgggttg ttgttgttgt ggctgatcta tcgattaggt     9600
gatgttgcga tttgtcgtag cagtgactat gtctggattt agttacttgg gtgatgctgt    9660
gattctgtca tagcagtgac tgtaaacttc aatcaggaga c                        9701
```

<210> SEQ ID NO 2
<211> LENGTH: 3061
<212> TYPE: PRT
<213> ORGANISM: Potato virus
<220> FEATURE:
<223> OTHER INFORMATION: Polyprotein containing HC-PRO of PVYN-605

<400> SEQUENCE: 2

```
Met Ala Ile Tyr Thr Ser Thr Ile Gln Phe Gly Ser Ile Glu Cys Lys
 1               5                  10                  15

Leu Pro Tyr Ser Pro Ala Pro Phe Gly Leu Val Ala Gly Lys Arg Glu
                20                  25                  30

Val Ser Thr Thr Thr Asp Pro Phe Ala Ser Leu Glu Met Gln Leu Ser
            35                  40                  45

Ala Arg Leu Arg Arg Gln Glu Phe Ala Thr Ile Arg Thr Ser Lys Asn
        50                  55                  60

Gly Thr Cys Met Tyr Arg Tyr Lys Thr Asp Val Gln Ile Ala Arg Ile
 65                  70                  75                  80

Gln Lys Lys Arg Glu Glu Arg Glu Arg Glu Glu Tyr Asn Phe Gln Met
                85                  90                  95

Ala Ala Ser Ser Val Val Ser Lys Ile Thr Ile Ala Gly Gly Glu Pro
                100                 105                 110

Pro Ser Lys Leu Glu Ser Gln Val Arg Arg Gly Val Ile His Thr Thr
            115                 120                 125

Pro Arg Met Arg Thr Ala Lys Thr Tyr His Thr Pro Lys Leu Thr Glu
        130                 135                 140

Gly Gln Met Asn His Leu Ile Lys Gln Val Lys Gln Ile Met Ser Thr
145                 150                 155                 160

Lys Gly Gly Ser Val Gln Leu Ile Ser Lys Lys Ser Thr His Val His
                165                 170                 175

Tyr Lys Glu Val Leu Gly Ser His Arg Ala Val Val Cys Thr Ala His
                180                 185                 190

Met Arg Gly Leu Arg Lys Arg Val Asp Phe Arg Cys Asp Lys Trp Thr
        195                 200                 205

Val Val Arg Leu Gln His Leu Ala Arg Thr Asp Lys Trp Thr Asn Gln
            210                 215                 220

Val Arg Ala Thr Asp Leu Arg Lys Gly Asp Ser Gly Val Ile Leu Ser
225                 230                 235                 240

Asn Thr Asn Leu Lys Gly Asn Phe Gly Arg Ser Ser Glu Gly Leu Phe
                245                 250                 255

Ile Val Arg Gly Ser His Glu Gly Lys Ile Tyr Asp Ala Arg Ser Lys
                260                 265                 270

Val Thr Gln Gly Val Met Asp Ser Met Val Gln Phe Ser Ser Ala Glu
            275                 280                 285

Ser Phe Trp Lys Gly Leu Asp Gly Asn Trp Ala Gln Met Arg Tyr Pro
        290                 295                 300

Thr Asp His Thr Cys Val Ala Gly Leu Pro Val Glu Asp Cys Gly Arg
305                 310                 315                 320

Val Ala Ala Ile Met Thr His Ser Ile Leu Pro Cys Tyr Lys Ile Thr
                325                 330                 335

Cys Pro Thr Cys Ala Gln Gln Tyr Ala Asn Leu Pro Ala Ser Asp Leu
                340                 345                 350

Leu Lys Ile Leu His Lys His Ala Ser Asp Gly Leu Asn Arg Leu Gly
            355                 360                 365

Ala Asp Lys Asp Arg Phe Val His Val Lys Lys Phe Leu Thr Ile Leu
        370                 375                 380

Glu His Leu Thr Glu Pro Val Asp Leu Ser Leu Glu Ile Phe Asn Glu
385                 390                 395                 400

Val Phe Lys Ser Ile Gly Glu Lys Gln Gln Ser Pro Phe Lys Asn Leu
                405                 410                 415

Asn Ile Leu Asn Asn Phe Phe Leu Lys Gly Lys Glu Asn Thr Ala Arg
```

```
                420             425             430
Glu Trp Gln Val Ala Gln Leu Ser Leu Leu Glu Leu Ala Arg Phe Gln
            435                 440                 445
Lys Asn Arg Thr Asp Asn Ile Lys Lys Gly Asp Ile Ser Phe Phe Arg
450                 455                 460
Asn Lys Leu Ser Ala Lys Ala Asn Trp Asn Leu Tyr Leu Ser Cys Asp
465                 470                 475                 480
Asn Gln Leu Asp Lys Asn Ala Ser Phe Leu Trp Gly Gln Arg Glu Tyr
                485                 490                 495
His Ala Lys Arg Phe Ser Asn Tyr Phe Glu Glu Ile Asp Pro Ala
            500                 505                 510
Lys Gly Tyr Ser Ala Tyr Glu Asn Arg Leu His Pro Asn Gly Thr Arg
            515                 520                 525
Lys Leu Ala Ile Gly Asn Leu Ile Val Pro Leu Asp Leu Ala Glu Phe
            530                 535                 540
Arg Arg Lys Met Lys Gly Asp Tyr Lys Arg Gln Pro Gly Val Ser Lys
545                 550                 555                 560
Lys Cys Thr Ser Lys Asp Gly Asn Tyr Val Tyr Pro Cys Cys Cys
                565                 570                 575
Thr Thr Leu Asp Asp Gly Ser Ala Val Glu Ser Thr Phe Tyr Pro Pro
                580                 585                 590
Thr Lys Lys His Leu Val Ile Gly Asn Ser Gly Asp Gln Lys Tyr Val
                595                 600                 605
Asp Leu Pro Lys Gly Asn Ser Glu Met Leu Tyr Ile Ala Arg Gln Gly
            610                 615                 620
Phe Cys Tyr Ile Asn Ile Phe Leu Ala Met Leu Ile Asn Ile Ser Glu
625                 630                 635                 640
Glu Asp Ala Lys Asp Phe Thr Lys Lys Val Arg Asp Met Cys Val Pro
                645                 650                 655
Lys Leu Gly Thr Trp Pro Thr Met Met Asp Leu Ala Thr Thr Cys Ala
                660                 665                 670
Gln Met Lys Ile Phe Tyr Pro Asp Val His Asp Ala Glu Leu Pro Arg
            675                 680                 685
Ile Leu Val Asp His Glu Thr Gln Thr Cys His Val Val Asp Ser Phe
            690                 695                 700
Gly Ser Gln Thr Thr Gly Tyr His Ile Leu Lys Ala Ser Ser Val Ser
705                 710                 715                 720
Gln Leu Ile Leu Phe Ala Asn Asp Glu Leu Glu Ser Asp Ile Lys His
                725                 730                 735
Tyr Arg Val Gly Gly Ile Pro Gly Ala Cys Pro Glu Leu Gly Ser Thr
            740                 745                 750
Ile Ser Pro Phe Arg Glu Gly Gly Ile Ile Met Ser Glu Ser Ala Ala
            755                 760                 765
Leu Lys Leu Leu Lys Gly Ile Phe Arg Pro Lys Val Met Lys Gln
            770                 775                 780
Leu Leu Leu Asp Glu Pro Tyr Leu Leu Ile Leu Ser Ile Leu Ser Pro
785                 790                 795                 800
Gly Ile Leu Met Ala Met Tyr Asn Asn Gly Ile Phe Glu Leu Ala Val
                805                 810                 815
Lys Leu Trp Ile Asn Glu Lys Gln Ser Ile Ala Met Ile Ala Ser Leu
            820                 825                 830
Leu Ser Ala Leu Ala Leu Arg Val Ser Ala Ala Glu Thr Leu Val Ala
            835                 840                 845
```

-continued

```
Gln Arg Ile Ile Ile Asp Thr Ala Ala Thr Asp Leu Leu Asp Ala Thr
            850                 855                 860

Cys Asp Gly Phe Asn Leu Asn Leu Thr Tyr Pro Thr Ala Leu Met Val
865                 870                 875                 880

Leu Gln Val Val Lys Asn Arg Asn Glu Cys Asp Asp Thr Leu Phe Lys
                    885                 890                 895

Ala Gly Phe Ser His Tyr Asn Met Ser Val Val Gln Ile Met Glu Lys
                900                 905                 910

Asn Tyr Leu Ser Leu Leu Gly Asp Ala Trp Lys Asp Leu Thr Trp Arg
            915                 920                 925

Glu Lys Leu Ser Ala Thr Trp His Ser Tyr Lys Ala Lys Arg Ser Ile
930                 935                 940

Thr Gln Phe Ile Lys Pro Ile Gly Lys Ala Asp Leu Lys Gly Leu Tyr
945                 950                 955                 960

Asn Ile Ser Pro Gln Ala Phe Leu Gly Gln Gly Val Gln Arg Val Lys
                    965                 970                 975

Gly Thr Ala Ser Gly Leu Asn Glu Arg Leu Asn Asn Tyr Ile Asn Thr
                980                 985                 990

Lys Cys Val Asn Ile Ser Ser Phe Phe Ile Arg Arg Ile Phe Arg Arg
            995                 1000                1005

Leu Pro Thr Phe Val Thr Phe Ile Asn Ser Leu Leu Val Ile Ser Met
1010                1015                1020

Leu Thr Ser Val Val Ala Val Cys Gln Ala Ile Ile Leu Asp Gln Arg
1025                1030                1035                1040

Lys Tyr Arg Lys Glu Ile Glu Leu Met Gln Ile Glu Lys Asn Glu Ile
                    1045                1050                1055

Val Cys Met Glu Leu Tyr Ala Ser Leu Gln Arg Lys Leu Glu Arg Glu
                1060                1065                1070

Phe Thr Trp Asp Glu Tyr Met Glu Tyr Leu Lys Ser Val Asn Pro Gln
                1075                1080                1085

Ile Val Gln Phe Ala Gln Ala Gln Met Glu Glu Tyr Asn Val Arg His
            1090                1095                1100

Gln Arg Ser Thr Pro Gly Val Lys Asn Leu Glu Gln Val Ala Phe
1105                1110                1115                1120

Ile Thr Leu Ile Ile Met Met Phe Asp Ala Glu Arg Ser Asp Cys Val
                    1125                1130                1135

Phe Lys Thr Leu Asn Lys Phe Lys Gly Ile Val Ser Ser Met Asp His
                1140                1145                1150

Glu Val Lys His Gln Ser Leu Asp Asp Val Ile Lys Asn Phe Asp Glu
            1155                1160                1165

Arg Asn Glu Val Ile Asp Phe Glu Leu Asn Glu Asp Thr Ile Lys Thr
1170                1175                1180

Ser Ser Val Leu Asp Thr Lys Phe Ser Asp Trp Trp Asp Arg Gln Ile
1185                1190                1195                1200

Gln Met Gly His Thr Leu Pro His Tyr Arg Thr Glu Gly His Phe Met
                    1205                1210                1215

Glu Phe Thr Arg Ala Thr Ala Val Gln Val Ala Asn Asp Ile Ala His
                1220                1225                1230

Ser Glu His Leu Asp Phe Leu Val Arg Gly Ala Val Gly Ser Gly Lys
            1235                1240                1245

Ser Thr Gly Leu Pro Val His Leu Ser Ala Ala Gly Ser Val Leu Leu
1250                1255                1260

Ile Glu Pro Thr Arg Pro Leu Ala Glu Asn Val Phe Lys Gln Leu Ser
1265                1270                1275                1280
```

```
Ser Glu Pro Phe Phe Lys Lys Pro Thr Leu Arg Met Arg Gly Asn Ser
            1285                1290                1295

Val Phe Gly Ser Ser Pro Ile Ser Ile Met Thr Ser Gly Phe Ala Leu
            1300                1305                1310

His Tyr Tyr Ala Asn Asn Arg Ser Gln Leu Thr Gln Phe Asn Phe Ile
            1315                1320                1325

Ile Phe Asp Glu Cys His Val Leu Asp Pro Ser Ala Met Ala Phe Arg
            1330                1335                1340

Ser Leu Leu Ser Val Tyr His Gln Thr Cys Lys Val Leu Lys Val Ser
1345                1350                1355                1360

Ala Thr Pro Val Gly Arg Glu Val Glu Phe Thr Thr Gln Gln Pro Val
            1365                1370                1375

Lys Leu Val Val Glu Asp Thr Leu Ser Phe Gln Ser Phe Val Asp Ala
            1380                1385                1390

Gln Gly Ser Lys Thr Asn Ala Asp Val Val Gln His Gly Ser Asn Ile
            1395                1400                1405

Leu Val Tyr Val Ser Ser Tyr Asn Glu Val Asp Thr Leu Ala Lys Leu
            1410                1415                1420

Leu Thr Asp Arg Asn Met Val Val Ser Lys Val Asp Gly Arg Thr Met
1425                1430                1435                1440

Lys His Gly Cys Leu Glu Ile Val Thr Lys Gly Thr Ser Ala Lys Pro
            1445                1450                1455

His Phe Val Val Ala Thr Asn Ile Ile Glu Asn Gly Val Thr Leu Asp
            1460                1465                1470

Ile Asp Val Val Val Asp Phe Gly Leu Lys Val Ser Pro Phe Leu Asp
            1475                1480                1485

Ile Asp Asn Arg Ser Ile Ala Tyr Asn Lys Ile Ser Val Ser Tyr Gly
            1490                1495                1500

Glu Arg Ile Gln Arg Leu Gly Arg Val Gly Arg Phe Lys Lys Gly Val
1505                1510                1515                1520

Ala Leu Arg Ile Gly His Thr Glu Lys Gly Ile Ile Glu Ile Pro Ser
            1525                1530                1535

Met Ile Ala Ser Glu Ala Ala Leu Ala Cys Phe Ala Tyr Asn Leu Pro
            1540                1545                1550

Val Met Thr Gly Gly Val Ser Thr Ser Leu Ile Gly Asn Cys Thr Val
            1555                1560                1565

Arg Gln Val Lys Thr Met Gln Gln Phe Glu Leu Ser Pro Phe Phe Ile
1570                1575                1580

Gln Asn Phe Val Ala His Asp Gly Ser Met His Pro Val Ile His Asp
1585                1590                1595                1600

Ile Leu Lys Lys Tyr Lys Leu Arg Asp Cys Met Thr Pro Leu Cys Asp
            1605                1610                1615

Gln Ser Ile Pro Tyr Arg Ala Ser Ser Thr Trp Leu Ser Val Ser Glu
            1620                1625                1630

Tyr Glu Arg Leu Gly Val Val Leu Asp Ile Pro Lys Gln Ile Lys Ile
            1635                1640                1645

Ala Phe His Ile Lys Asp Ile Pro Pro Lys Leu His Glu Met Leu Trp
            1650                1655                1660

Glu Thr Val Ile Lys Tyr Lys Asp Val Cys Leu Phe Pro Ser Ile Arg
1665                1670                1675                1680

Ala Ser Ser Ile Ser Lys Ile Ala Tyr Thr Leu Arg Thr Asp Leu Phe
            1685                1690                1695

Ala Ile Pro Arg Thr Leu Ile Leu Val Glu Arg Leu Ile Glu Glu Glu
```

```
                        1700                1705                1710
Arg Val Lys Gln Ser Gln Phe Arg Ser Leu Ile Asp Glu Gly Cys Ser
            1715                1720                1725
Ser Met Phe Ser Ile Val Asn Leu Thr Asn Thr Leu Arg Ala Arg Tyr
        1730                1735                1740
Ala Lys Asp Tyr Thr Ala Glu Asn Ile Gln Lys Leu Glu Lys Val Arg
1745                1750                1755                1760
Ser Gln Leu Lys Glu Phe Ser Asn Leu Asn Gly Ser Ala Cys Glu Glu
                1765                1770                1775
Asn Leu Met Lys Arg Tyr Glu Ser Leu Gln Phe Val His His Gln Ala
            1780                1785                1790
Thr Thr Ser Leu Ala Lys Asp Leu Lys Leu Lys Gly Val Trp Lys Lys
        1795                1800                1805
Ser Leu Val Val Gln Asp Leu Leu Ile Ala Gly Ala Val Ala Ile Gly
    1810                1815                1820
Gly Ile Gly Leu Ile Tyr Ser Trp Phe Thr Gln Ser Val Glu Thr Val
1825                1830                1835                1840
Ser His Gln Gly Lys Asn Lys Ser Lys Arg Ile Gln Ala Leu Lys Phe
                1845                1850                1855
Arg His Ala Arg Asp Lys Arg Ala Gly Phe Glu Ile Asp Asn Asn Asp
            1860                1865                1870
Asp Thr Ile Glu Glu Phe Gly Ser Ala Tyr Arg Lys Lys Gly Lys
        1875                1880                1885
Gly Lys Gly Thr Thr Val Gly Met Gly Lys Ser Ser Arg Arg Phe Val
    1890                1895                1900
Asn Met Tyr Gly Phe Asp Pro Thr Glu Tyr Ser Phe Ile Gln Phe Val
1905                1910                1915                1920
Asp Pro Leu Thr Gly Ala Gln Ile Glu Glu Asn Val Tyr Ala Asp Ile
                1925                1930                1935
Arg Asp Ile Gln Glu Arg Phe Ser Asp Val Arg Lys Lys Met Val Glu
            1940                1945                1950
Asp Asp Glu Ile Glu Leu Gln Ala Leu Gly Ser Asn Thr Thr Ile His
        1955                1960                1965
Ala Tyr Phe Arg Lys Asp Trp Ser Asp Lys Ala Leu Lys Ile Asp Leu
    1970                1975                1980
Met Pro His Asn Pro Leu Lys Ile Cys Asp Lys Ser Asn Gly Ile Ala
1985                1990                1995                2000
Lys Phe Pro Glu Arg Glu Leu Glu Leu Arg Gln Thr Gly Pro Ala Ile
                2005                2010                2015
Glu Val Asp Val Lys Asp Ile Pro Lys Gln Glu Val Glu His Glu Ala
            2020                2025                2030
Lys Ser Leu Met Arg Gly Leu Arg Asp Phe Asn Pro Ile Ala Gln Thr
        2035                2040                2045
Val Cys Arg Val Lys Val Ser Val Glu Tyr Gly Thr Ser Glu Met Tyr
    2050                2055                2060
Gly Phe Gly Phe Gly Ala Tyr Ile Ile Val Asn His His Leu Phe Lys
2065                2070                2075                2080
Ser Phe Asn Gly Ser Met Glu Val Arg Ser Met His Gly Thr Phe Arg
                2085                2090                2095
Val Lys Asn Leu His Ser Leu Ser Val Leu Pro Ile Lys Gly Arg Asp
            2100                2105                2110
Ile Ile Ile Ile Lys Met Pro Lys Asp Phe Pro Val Phe Pro Gln Lys
        2115                2120                2125
```

-continued

```
Leu His Phe Arg Ala Pro Val Gln Asn Glu Arg Ile Cys Leu Val Gly
         2130                2135                2140

Thr Asn Phe Gln Glu Lys His Ala Ser Ser Ile Ile Thr Glu Thr Ser
2145                2150                2155                2160

Thr Thr Tyr Asn Val Pro Gly Ser Thr Phe Trp Lys His Trp Ile Glu
             2165                2170                2175

Thr Asn Asp Gly His Cys Gly Leu Pro Val Val Ser Thr Ala Asp Gly
         2180                2185                2190

Cys Leu Val Gly Ile His Ser Leu Ala Asn Asn Val Gln Thr Thr Asn
             2195                2200                2205

Tyr Tyr Ser Ala Phe Asp Glu Asp Phe Glu Ser Lys Tyr Leu Arg Thr
2210                2215                2220

Asn Glu His Asn Glu Trp Thr Lys Ser Trp Val Tyr Asn Pro Asp Thr
2225                2230                2235                2240

Val Leu Trp Gly Pro Leu Lys Leu Lys Glu Ser Thr Pro Lys Gly Leu
             2245                2250                2255

Phe Lys Thr Thr Lys Leu Val Gln Asp Leu Ile Asp His Asp Val Val
         2260                2265                2270

Val Glu Gln Ala Lys His Ser Ala Trp Met Tyr Glu Ala Leu Thr Gly
         2275                2280                2285

Asn Leu Gln Ala Val Ala Thr Met Lys Ser Gln Leu Val Thr Lys His
         2290                2295                2300

Val Val Lys Gly Glu Cys Arg His Phe Lys Glu Phe Leu Thr Val Asp
2305                2310                2315                2320

Ser Glu Ala Glu Ala Phe Phe Arg Pro Leu Met Asp Ala Tyr Gly Lys
             2325                2330                2335

Ser Leu Leu Asn Arg Glu Ala Tyr Ile Lys Asp Ile Met Lys Tyr Ser
             2340                2345                2350

Lys Pro Ile Asp Val Gly Ile Val Asp Cys Asp Ala Phe Glu Glu Ala
             2355                2360                2365

Ile Asn Arg Val Ile Ile Tyr Leu Gln Val His Gly Phe Gln Lys Cys
         2370                2375                2380

Asn Tyr Ile Thr Asp Glu Gln Glu Ile Phe Lys Ala Leu Asn Met Lys
2385                2390                2395                2400

Ala Ala Val Gly Ala Met Tyr Gly Gly Lys Lys Lys Asp Tyr Phe Glu
             2405                2410                2415

His Phe Thr Glu Ala Asp Lys Glu Glu Ile Val Met Gln Ser Cys Phe
             2420                2425                2430

Arg Leu Tyr Lys Gly Ser Leu Gly Ile Trp Asn Gly Ser Leu Lys Ala
             2435                2440                2445

Glu Leu Arg Cys Lys Glu Lys Ile Leu Ala Asn Lys Thr Arg Thr Phe
         2450                2455                2460

Thr Ala Ala Pro Leu Asp Thr Leu Leu Gly Gly Lys Val Cys Val Asp
2465                2470                2475                2480

Asp Phe Asn Asn Gln Phe Tyr Ser Lys Asn Ile Glu Cys Cys Trp Thr
             2485                2490                2495

Val Gly Met Thr Lys Phe Tyr Gly Gly Trp Asp Lys Leu Leu Arg Arg
             2500                2505                2510

Leu Pro Glu Asn Trp Val Tyr Cys Asp Ala Asp Gly Ser Gln Phe Asp
             2515                2520                2525

Ser Ser Leu Thr Pro Tyr Leu Ile Asn Ala Val Leu Ile Ile Arg Ser
         2530                2535                2540

Thr Tyr Met Glu Asp Trp Asp Leu Gly Leu Gln Met Leu Arg Asn Leu
2545                2550                2555                2560
```

Tyr Thr Glu Ile Ile Tyr Thr Pro Ile Ser Thr Pro Asp Gly Thr Ile
                2565                2570                2575

Val Lys Lys Phe Arg Gly Asn Asn Ser Gly Gln Pro Ser Thr Val Val
                2580                2585                2590

Asp Asn Ser Leu Met Val Val Leu Ala Met His Tyr Ala Leu Ile Lys
            2595                2600                2605

Glu Cys Val Glu Phe Glu Ile Asp Ser Thr Cys Val Phe Phe Val
            2610                2615                2620

Asn Gly Asp Asp Leu Leu Ile Ala Val Asn Pro Glu Lys Glu Ser Ile
2625                2630                2635                2640

Leu Asp Arg Met Ser Gln His Phe Ser Asp Leu Gly Leu Asn Tyr Asp
                2645                2650                2655

Phe Ser Ser Arg Thr Arg Arg Lys Glu Glu Leu Trp Phe Met Ser His
                2660                2665                2670

Arg Gly Leu Leu Ile Glu Asp Met Tyr Val Pro Lys Leu Glu Glu Glu
            2675                2680                2685

Arg Ile Val Ser Ile Leu Gln Trp Asp Arg Ala Asp Leu Pro Glu His
2690                2695                2700

Arg Leu Glu Ala Ile Cys Ala Ala Met Ile Glu Ser Trp Gly Tyr Phe
2705                2710                2715                2720

Glu Leu Thr His Gln Ile Arg Arg Phe Tyr Ser Trp Leu Leu Gln Gln
            2725                2730                2735

Gln Pro Phe Ser Thr Ile Ala Gln Glu Gly Lys Ala Pro Tyr Ile Ala
                2740                2745                2750

Ser Met Ala Leu Lys Lys Leu Tyr Met Asn Arg Thr Val Asp Glu Glu
            2755                2760                2765

Glu Leu Lys Ala Phe Thr Glu Met Met Val Ala Leu Asp Asp Glu Phe
            2770                2775                2780

Glu Cys Asp Thr Tyr Glu Val His His Gln Gly Asn Asp Thr Ile Asp
2785                2790                2795                2800

Ala Gly Gly Ser Thr Lys Lys Asp Ala Lys Gln Glu Gln Gly Ser Ile
                2805                2810                2815

Gln Pro Asn Leu Asn Lys Glu Lys Glu Lys Asp Val Asn Val Gly Thr
            2820                2825                2830

Ser Gly Thr His Thr Val Pro Arg Ile Lys Ala Ile Thr Ser Lys Met
            2835                2840                2845

Lys Met Pro Lys Ser Lys Gly Ala Thr Val Leu Asn Leu Glu His Leu
            2850                2855                2860

Leu Glu Tyr Ala Pro Gln Gln Ile Asp Ile Ser Asn Thr Arg Ala Thr
2865                2870                2875                2880

Gln Ser Gln Phe Asp Thr Trp Tyr Glu Ala Val Gln Leu Ala Tyr Asp
                2885                2890                2895

Ile Gly Glu Thr Glu Met Pro Thr Val Met Asn Gly Leu Met Val Trp
            2900                2905                2910

Cys Ile Glu Asn Gly Thr Ser Pro Asn Ile Asn Gly Val Trp Val Met
            2915                2920                2925

Met Asp Gly Asn Glu Gln Val Glu Tyr Pro Leu Lys Pro Ile Val Glu
            2930                2935                2940

Asn Ala Lys Pro Thr Leu Arg Gln Ile Met Ala His Phe Ser Asp Val
2945                2950                2955                2960

Ala Glu Ala Tyr Ile Glu Met Arg Asn Lys Lys Glu Pro Tyr Met Pro
                2965                2970                2975

Arg Tyr Gly Leu Val Arg Asn Leu Arg Asp Gly Ser Leu Ala Arg Tyr

-continued

```
            2980                2985                2990

Ala Phe Asp Phe Tyr Glu Val Thr Ser Arg Thr Pro Val Arg Ala Arg
        2995                3000                3005

Glu Ala His Ile Gln Met Lys Ala Ala Ala Leu Lys Ser Ala Gln Ser
    3010                3015                3020

Arg Leu Phe Gly Leu Asp Gly Gly Ile Ser Thr Gln Glu Glu Asn Thr
3025                3030                3035                3040

Glu Arg His Thr Thr Glu Asp Val Ser Pro Ser Met His Thr Leu Leu
                3045                3050                3055

Gly Val Lys Asn Met
            3060

<210> SEQ ID NO 3
<211> LENGTH: 9698
<212> TYPE: DNA
<213> ORGANISM: Potato virus
<220> FEATURE:
<223> OTHER INFORMATION: PVYO-139 sequence

<400> SEQUENCE: 3
aattaaaaca actcaataca acataagaaa aacagcgcaa aaacactcat aaacgcttat     60
tctcactcaa gcatcttgct aagtttcagt ttaaatcatt tccttgcaat tctcttaaac    120
aatattggaa accatttcaa ctcaacaagc aatttcatca cttccaacca atttaaaatc    180
ctcgatggca acttacatgt caacgatctg tttcggttcg tttgaatgca agctaccata    240
ctcacccgcc tcttgcgggc ttattgtgaa ggaacgagaa gtgctggctt ccgttaatcc    300
tttcgcagat ctggaaacac aacttagtgc acgattgctc aagcaagaat atgctactgt    360
tcgtgtgctc aagaacggta cttttacgta tcgatacaag actgatgccc agataaagcg    420
cattcagaag aaactggaga ggaaggatag ggaagaatat cacttccaaa tggccgctcc    480
tagtattgtg tcaaaaatta ctatagctgg tggagatcct ccatcaaagt ctgagccaca    540
agcaccaaga gggatcattc atacaactcc aagggtgcgt aaagtcaaga cacgccccat    600
aataaagttg acagaaggcc agatgaatca tttcattaag caggtaaagc agattatgtc    660
ggagaagaga gggtctgtcc acttaattaa taagaagacc actcatgttc aatataagga    720
gatacttggt gcatactccg ccacggttcg aactgcacat atgatgggtt tgcgacggag    780
agtggacttc cgatgtgata tgtggacagt tggacttttg caacgtctcg ctcggacgga    840
caaatggtcc aatcaagtcc gcactatcaa catacgaagg ggtgatagtg gagtcatctt    900
gaacacaaaa agcctcaaag gccactttgg tagaagttca ggagacttgt tcatagtgcg    960
cggatcacat gaagggaaat tgtacgatgc acgttctaga gttactcaga gtgttttgga   1020
ctcaatgatc cagttttcga atgctgataa tttttggaag ggtctggacg gcaattgggc   1080
acgaatgaga tatccttcgg atcacacatg tgtagctggt ttacctgtcg aagattgtgg   1140
tagggttgct gcattgatgg cacacagtat cctcccatgc tataagataa cctgccccac   1200
ctgtgctcaa cagtatgcca gcttgccggt tagcgatctg tttaagctgt tgcataaaca   1260
tgcaagagat ggtttgaacc gattgggagc agataaagac cggtttatac atgttaataa   1320
gttcttgata gcgttagagc atctaactga accggtggat ttgaatctcg agcttttcaa   1380
tgagatattt aaatccatag gggagaagca gcaagcaccg ttcaagaatt taaatgtctt   1440
gaataatttc ttcctgaaag gaaaagaaaa tacagctcat gaatggcagg tggctcaatt   1500
gagtttgctc gaattagcaa ggttccagaa gaatagaact gataacatca agaaaggtga   1560
tatatccttc ttcagaaata aattatttgc caaggcaaat tggaatctgt atttgtcgtg   1620
```

```
cgacaaccaa ttggacaaaa atgcaaattt cctgtgggga caaagggagt atcatgctaa   1680
gcggtttttc tcaaacttct ttgaggaaat tgatccagca aagggatact cagcatatga   1740
aatccgcaag catccaagtg gaacaaggaa gctctcaatt ggtaacttag ttgtcccact   1800
tgatttagct gagtttaggc agaagatgaa aggtgactat aggaaacaac cagggtcag    1860 cagaaagtgc acgagttcga agatggtaa ttatgtgtat ccctgttgtt gcacaacact    1920
tgatgatggt tcagccattg aatcaacatt ctatccacca actaaaaagc accttgtaat   1980
aggcaatagt ggtgaccaaa agtttgttga tttaccaaaa ggggattcag agatgttata   2040
cattgccaag cagggttatt gttatattaa cgtgtttctt gcaatgctaa ttaacattgg   2100
cgaggaggat gcaaaggatt tcacaaagaa agtccgcgac atgtgtgtgc gaagcttgg   2160 aacctggcca actatgatgg atttggcgac cacttgtgct caaatgagaa tattctatcc   2220
tgacgtgcat gatgcagagc tgcctagttt attggttgac catgacactc aaacgtgtca   2280
tgtggttgac tcatttggct cgcagacaac tggatatcat attctaaaag catccagcgt   2340
gtctcaactt atcttgtttg caaatgatga attagaatct gatataaaac attatagagt   2400
tggtggcgtt cctaatgcat gccctgaact tgggtccacg atatcacctt ttagagaagg   2460
aggagttata atgtctgagt cggcagcgct gaaactgctt ttgaagggaa ttttagacc    2520 taaggtgatg agacagttgc tgttagatga gccttacctg ttgattctat caatattatc   2580
ccctggcata ctgatggcta tgtataataa tgggattttt gaacttgcgg taagattgtg   2640
gattaatgag aaacaatcca tagctatgat agcatcgcta ctatcagctt tagccctacg   2700
agtgtcagcg gcagaaacac tcgtcgcaca gagaattata attgatgctg cagctacaga   2760
cctccttgat gctacgtgtg atggattcaa cctacatcta acgtacccca ctgcattaat   2820
ggtgttgcaa gttgttaaga atagaaatga atgtgatgat ccctattca aggcgggttt    2880 tccaagttac aacacgagtg ttgtgcagat tatggaaaaa aattatctaa gtctcttgga   2940
cgatgcttgg aaagatttaa cttggcggga aaaattatcc gcaacatggt actcatacag   3000
agcaaaacgc tctatcactc ggtacataaa acccacagga agggcagatt tgaaagggtt   3060
atacaacata tcaccacaag cattcttggg ccgaagcgcc caggtggtca aaggcactgc   3120
ctcaggattg agcgagcgat ttaataatta tttcaatact aagtgtgtaa atatttcatc   3180 tttttttcatt cgtagaatct ttaggcgttt gccaactttc gtcacttttg ttaactcatt   3240
attagttatt agtatgttaa ctagcgtagt ggcagtgtgt caggcaataa ttttagatca   3300
gaggaagtat aggagagaaa tcgagttgat gcagatagag aagaatgaga ttgtctgcat   3360
ggagctatat gcaagtttac agcgcaaact tgaacgcgat ttcacatggg atgagtacat   3420
tgagtatttg aagtcagtga accctcagat agttcagttt gctcaagcgc agatggaaga   3480
atatgatgtg cgacaccagc gttccacacc aggtgttaaa aatttggaac aagaggtagc   3540
atttatggct ttagtcatca tggtgttcga tgctgaaagg agtgattgcg ttttcaaaac   3600
tctcaataaa tttaagggtg tccttttcctc gctggaccat gaagttcgac atcagtcctt   3660
agacgatgtg atcaagaatt ttgatgagag gaatgagatt attgattttg agttgagtga   3720
ggacacaatt cgaacatcat cagtgctaga tacaaagttt agtgattggt gggaccgaca   3780
aatccagatg ggacatacac ttccacatta cagaaccgag gggcacttca tggaatttac   3840
aagagcaact gctgttcaag tggctaatga cattgcccat agtgaacacc tagactttt    3900 agtaagggga gctgttgggt ctggaaagtc aactgggttg cctgttcatc ttagtgtagc   3960
cggatctgtg ctttttaattg aaccaacgcg accactagcg gagaacgttt tcaaacagct   4020
```

```
atctagtgaa ccattcttca agaagccaac actgcgtatg cgcggaaata gtatatttgg   4080
ctcttctcca atctccgtca tgactagcgg attcgcgcta cactacttcg ccaataaccg   4140
ctcccaatta gctcagttca actttgtaat atttgatgag tgccatgttc tggatccttc   4200
cgcaatggcg ttccgcagtc tgctgagtgt ttatcatcaa gcatgcaaag tattaaaagt   4260
gtcagctact ccagtgggaa gagaggttga attcacaaca cagcagccag tcaagttgat   4320
agtggaggac acactgtctt tccaatcatt tgttgatgca caaggttcta aaactaatgc   4380
tgatgttgtt cagtttggtt caaacgtact tgtgtatgtg tcgagctaca atgaagttga   4440
taccttggct aagctcctaa cagacaagaa tatgatggtc acaaaggttg atggcagaac   4500
aatgaagcac ggttgcctag aaattgtcac aaaaggaacc agtgcgagac cacattttgt   4560
tgtagcaacc aacataattg aaaatggagt aactttggac atagacgtgg ttgtggattt   4620
tgggttgaaa gtctcaccat tcttggacat tgacaatagg agcattgcct acaataagga   4680
gagtgttagc tatggtgaaa gaattcaaag gttgggtcgt gttggacgct tcaagaaagg   4740
agtagcattg cgcattggac acactgagaa gggaattatt gaaattccaa gcatggttgc   4800
tactgaggcg gctcttgctt gctttgcata aacttgcca gtgatgacag gcggcgtctc   4860
aactagtctg attggcaatt gtactgtgcg ccaggttaaa acaatgcagc aatttgaatt   4920
gagtcccttc tttatccaga atttcgttgc tcatgatgga tcaatgcatc ctgtcataca   4980
tgacattctt aaaaagtata aacttcgaga ttgtatgaca cctttgtgcg atcagtctat   5040
accatacagg gcatcgtgca cttggttatc ggttagtgaa tatgagcgac ttggagtggc   5100
cttagaaatt ccaaagcaaa tcaaaattgc attccatatc aaagagatcc ctcctaagct   5160
ccacgaaatg ctttgggaaa cggttgtcaa atacaaagac gtttgcttat ttccaagcat   5220
tcgagcatcg tccatcagca aaatcgcata cacattgcgt acagacctct tcgccatccc   5280
aagaactcta atattggtgg agagattact tgaagaggag cgagtgaagc agagccaatt   5340
cagaagtctc atcgatgaag ggtgctcaag tatgttttca attgttaact tgaccaacac   5400
tctcagagct agatatgcaa aagattacac cgcagagaac atacaaaaac ttgagaaagt   5460
gagaagtcaa ttaaaagaat tctcaaatct ggatggttct gcatgtgagg agaatttaat   5520
aaagaggtat gagtctttgc agttcgttca tcaccaagct gcgacgtcac ttgcaaagga   5580
tctcaagttg aaggggacct ggaagaaatc attagtggct aaagacttga tcatagcagg   5640
cgctgttgca attggtggta taggactcat atatagttgg ttcacacaat cagttgagac   5700
tgtgtcccac caagggaaaa ataaatccaa aagaatccaa gccttgaagt ttcgccatgc   5760
tcgtgacaaa agggctggct ttgaaattga caacaatgat gacacaatag aggaattctt   5820
tggatctgca tataggaaaa agggaaaagg taaaggtacc acagttggta tgggcaagtc   5880
aagcaggaag ttcatcaaca tgtatgggtt tgatccaaca gagtactcat tcatccagtt   5940
cgttgatcca ctcactgggg cgcaaatagg agagaatgtc tatgctgaca ttagagacat   6000
tcaagataga tttagtgaag tgcgaagaaa aatggttgag aatgatgaca ttgaaatgca   6060
agccttgggt agtaacacaa ccatacatgc atacttcagg aaagattggt ctgacaaagc   6120
tttgaagatt gacttaatgc cacacaaccc actcaaagtt tgtgacaaaa caaatggcat   6180
tgcaaaattt cctgagagag agctcgaact aaggcagact gggccagctg tagaagtcaa   6240
tgtgaaggac ataccagcac aggaggtgga gcatgaagct aaatcgctca tgagaggctt   6300
gagagacttc aatccaattg cccaaacagt ttgtaggctg aaagtatctg ttgaatatgg   6360
gacatcagag atgtacggtt ttggatttgg agcatacata atagcgaacc accatttgtt   6420
```

```
taggagttac aatggttcca tggaggtgca atccatgcac ggtacattca gggtgaagaa    6480
tctacacagt ttgagcgttc tgccaattaa aggtagggac atcatcctca tcaaaatgcc    6540
gaaagatttc cctgtctttc cacagaaatt gcatttccga gctcctatac agaatgaaag    6600
agtttgttta gttgggacca actttcagga gaagtatgca tcgtcaatca tcacagaaac    6660
aagcactact tacaatatac caggcagcac attctggaag cattggattg aaacagataa    6720
tggacattgt ggactaccag tggtaagcac tgccgatgga tgtctagtcg aattcacag    6780 tttggcaaac aatgcacaca ccacgaacta ctactcagcc ttcgatgagg attttgaaag    6840
caagtacctc cgggccaatg agcacaatga atgggtcaag tcttggaaat ataatccaga    6900
cacagtgttg tggggcccgt tgaaacttaa agacagcact cccaaagggt tatttaaaac    6960
aacaaagctt gtgcaagatc taatcgagca tgatgtagtg gtggagcaag ctaagcactc    7020
tgcgtggatg tttgaagcct tgacaggaaa tttgcaagct gtcgcaacaa tgaagagcca    7080
attagtaacc aagcatgtag ttaaaggaga gtgtcgacac ttcaaggagt tcctgactgt    7140
ggatgcagaa gcagaggcat tcttcaggcc tttgatggat gcgtatggga aaagcttgct    7200
gaacagagat gcgtacatca aggacataat gaagtattca aaacctatag atgttggtat    7260
cgtggattgt gatgcattcg aggaagccat caatagggtt atcatctacc tgcaagtgca    7320
cggcttcaag aagtgtgcat atgtcactga cgagcaagaa attttcaaag cgcttaacat    7380
gaaagctgca gtcggagcca tgtatggtgg caaaaagaaa gactactttg agcatttcac    7440
tgatgcagac aaggaagaaa tagtcatgca aagctgtctg cgattgtata aaggcttgct    7500
cggcatttgg aatggatcat tgaaggcaga gctccggtgt aaggaaaaga tacttgcaaa    7560
taagacgagg acattcactg ctgcacctct agacactttg ctgggtggta agtgtgtgt    7620 tgacgacttc aataatcaat tttattcaaa gaatattgag tgctgttgga cagttgggat    7680
gactaagttt tatggtggtt gggataaact gcttcggcgt ttacctgaga attgggtata    7740
ctgtgatgct gatggctcac agtttgatag ttcactaact ccatacttat tcaatgctgt    7800
tctcaccatc agaagcacat acatggaaga ctgggatgtg gggctgcaaa tgctgcgtaa    7860
tttatacact gagattgttt acacacctat ttcaactcca gatggaacaa ttgttaagaa    7920
gttcagagga ataacagtg gtcagccttc tactgttgtg gacaactctc ttatggtcgt    7980
ccttgccatg cactatgctt tcatcagaga aggcattgag tttgaagaaa ctgacagcac    8040
gtgcgtgttc tttgtcaatg gtgatgattt gctgattgct gtgaatccgg ataaagagga    8100
cattcttgac agattgtcac aacacttctc agatcttggc ttaaattatg atttctcgtc    8160
aagaacaaga aataaggaag agttgtggtt tatgtctcat aggggcctac tgattgaggg    8220
catgtacgtg ccgaaacttg aagaagaaag gattgtgtcc attctccaat gggacagagc    8280
agacttggct gaacacaggc ttgaggcgat ttgcgcacgt atgatagagt cctgggggtta    8340 ttctgaacta acacaccaaa tcaggagatt ctactcatgg ttattgcaac agcaaccttt    8400
tgcaacaata gcgcaggagg ggaaggctcc ttatatagca agcatggcat taaggaaact    8460
gtatatggat agggctgtgg atgaggaaga gcttagagcc ttcactgaaa tgatggtcgc    8520
attagacgat gagtttgagt ttgactctta tgaagtatac catcaagcaa atgacacaat    8580
tgatgcagga ggaagcaaca agaaagatac aaaaccagag caaagcagca tccagtcaaa    8640
cccgaacaaa ggaaaagata agatgtgaa tgccggcaca tctgggacac acactgtacc    8700
gagaatcaag gctatcacgt ccaaaatgag aatgcccaaa agcaagggag cagctgtgct    8760
gaatttagaa cacttgcttg agtatgctcc acaacaaatt gatatttcaa atactcgggc    8820
```

```
aactcaatca cagtttgata cgtggtatga agcagtgcgg atggcatacg acataggaga    8880
aactgagatg ccaactgtga tgaatgggct tatggtttgg tgcattgaaa atggaacctc    8940
gccaaatgtc aacggagttt gggttatgat ggatgggaat gaacaagttg agtacccgtt    9000
gaaaccaatc gttgagaatg caaaaccaac ccttaggcaa atcatggcac atttctcaga    9060
tgttgcagaa gcgtatatag aaatgcgcaa caaaaaggaa ccatatatgc cacgatatgg    9120
tttaattcga atctgcggg atatgggttt agcgcgttat gcttttgact tttatgaggt     9180
cacatcacga acaccagtga gggctaggga agcgcaaatt caaatgaagg ccgcagcatt    9240
gaaatcagcc caacctcgac ttttcgggtt ggacggtggc atcagtacac aagaggagaa    9300
cacagagagg cacaccaccg aggatgtctc tccaagtatg catactctac ttggagtcaa    9360
gaacatgtga tgtagtgtct ctccggacga tatataaata tttacatatg cagtaagtat    9420
tttggctttt cctgtactac ttttatcata attaataatc agtttgaata ttactaatag    9480
atagaggtgg cagggtgatt tcgtcattgt ggtgactcta tctgttaatt tcgcattatt    9540
aagtcttaga taaaagtgcc gggttgtcgt tgttgtggat gattcatcga ttaggtgatg    9600
ttgcgattct gtcgtagcag tgactatgtc tggatctatc tgcttgggtg atgttgtgat    9660
tttgtcataa cagtgactgt aaacttcaat caggagac                            9698

<210> SEQ ID NO 4
<211> LENGTH: 3081
<212> TYPE: PRT
<213> ORGANISM: Potato virus
<220> FEATURE:
<223> OTHER INFORMATION: Polyprotein containing HC-PRO of PVYO-139

<400> SEQUENCE: 4

Met Glu Thr Ile Ser Thr Gln Gln Ala Ile Ser Ser Leu Pro Thr Asn
 1               5                  10                  15

Leu Lys Ser Ser Met Ala Thr Tyr Met Ser Thr Ile Cys Phe Gly Ser
            20                  25                  30

Phe Glu Cys Lys Leu Pro Tyr Ser Pro Ala Ser Cys Gly Leu Ile Val
        35                  40                  45

Lys Glu Arg Glu Val Leu Ala Ser Val Asn Pro Phe Ala Asp Leu Glu
    50                  55                  60

Thr Gln Leu Ser Ala Arg Leu Leu Lys Gln Glu Tyr Ala Thr Val Arg
65                  70                  75                  80

Val Leu Lys Asn Gly Thr Phe Thr Tyr Arg Tyr Lys Thr Asp Ala Gln
                85                  90                  95

Ile Lys Arg Ile Gln Lys Lys Leu Glu Arg Lys Asp Arg Glu Glu Tyr
            100                 105                 110

His Phe Gln Met Ala Ala Pro Ser Ile Val Ser Lys Ile Thr Ile Ala
        115                 120                 125

Gly Gly Asp Pro Pro Ser Lys Ser Glu Pro Gln Ala Pro Arg Gly Ile
    130                 135                 140

Ile His Thr Thr Pro Arg Val Arg Lys Val Lys Thr Arg Pro Ile Ile
145                 150                 155                 160

Lys Leu Thr Glu Gly Gln Met Asn His Phe Ile Lys Gln Val Lys Gln
                165                 170                 175

Ile Met Ser Glu Lys Arg Gly Ser Val His Leu Ile Asn Lys Lys Thr
            180                 185                 190

Thr His Val Gln Tyr Lys Glu Ile Leu Gly Ala Tyr Ser Ala Thr Val
        195                 200                 205
```

-continued

```
Arg Thr Ala His Met Met Gly Leu Arg Arg Arg Val Asp Phe Arg Cys
210                 215                 220

Asp Met Trp Thr Val Gly Leu Leu Gln Arg Leu Ala Arg Thr Asp Lys
225                 230                 235                 240

Trp Ser Asn Gln Val Arg Thr Ile Asn Ile Arg Arg Gly Asp Ser Gly
                245                 250                 255

Val Ile Leu Asn Thr Lys Ser Leu Lys Gly His Phe Gly Arg Ser Ser
                260                 265                 270

Gly Asp Leu Phe Ile Val Arg Gly Ser His Glu Gly Lys Leu Tyr Asp
                275                 280                 285

Ala Arg Ser Arg Val Thr Gln Ser Val Leu Asp Ser Met Ile Gln Phe
290                 295                 300

Ser Asn Ala Asp Asn Phe Trp Lys Gly Leu Asp Gly Asn Trp Ala Arg
305                 310                 315                 320

Met Arg Tyr Pro Ser Asp His Thr Cys Val Ala Gly Leu Pro Val Glu
                325                 330                 335

Asp Cys Gly Arg Val Ala Ala Leu Met Ala His Ser Ile Leu Pro Cys
                340                 345                 350

Tyr Lys Ile Thr Cys Pro Thr Cys Ala Gln Gln Tyr Ala Ser Leu Pro
                355                 360                 365

Val Ser Asp Leu Phe Lys Leu Leu His Lys His Ala Arg Asp Gly Leu
370                 375                 380

Asn Arg Leu Gly Ala Asp Lys Asp Arg Phe Ile His Val Asn Lys Phe
385                 390                 395                 400

Leu Ile Ala Leu Glu His Leu Thr Glu Pro Val Asp Leu Asn Leu Glu
                405                 410                 415

Leu Phe Asn Glu Ile Phe Lys Ser Ile Gly Glu Lys Gln Gln Ala Pro
                420                 425                 430

Phe Lys Asn Leu Asn Val Leu Asn Asn Phe Phe Leu Lys Gly Lys Glu
                435                 440                 445

Asn Thr Ala His Glu Trp Gln Val Ala Gln Leu Ser Leu Leu Glu Leu
450                 455                 460

Ala Arg Phe Gln Lys Asn Arg Thr Asp Asn Ile Lys Lys Gly Asp Ile
465                 470                 475                 480

Ser Phe Phe Arg Asn Lys Leu Phe Ala Lys Ala Asn Trp Asn Leu Tyr
                485                 490                 495

Leu Ser Cys Asp Asn Gln Leu Asp Lys Asn Ala Asn Phe Leu Trp Gly
                500                 505                 510

Gln Arg Glu Tyr His Ala Lys Arg Phe Phe Ser Asn Phe Glu Glu
                515                 520                 525

Ile Asp Pro Ala Lys Gly Tyr Ser Ala Tyr Glu Ile Arg Lys His Pro
530                 535                 540

Ser Gly Thr Arg Lys Leu Ser Ile Gly Asn Leu Val Val Pro Leu Asp
545                 550                 555                 560

Leu Ala Glu Phe Arg Gln Lys Met Lys Gly Asp Tyr Arg Lys Gln Pro
                565                 570                 575

Gly Val Ser Arg Lys Cys Thr Ser Lys Asp Gly Asn Tyr Val Tyr
                580                 585                 590

Pro Cys Cys Cys Thr Thr Leu Asp Asp Gly Ser Ala Ile Glu Ser Thr
                595                 600                 605

Phe Tyr Pro Pro Thr Lys Lys His Leu Val Ile Gly Asn Ser Gly Asp
610                 615                 620

Gln Lys Phe Val Asp Leu Pro Lys Gly Asp Ser Glu Met Leu Tyr Ile
625                 630                 635                 640
```

```
Ala Lys Gln Gly Tyr Cys Tyr Ile Asn Val Phe Leu Ala Met Leu Ile
            645                 650                 655

Asn Ile Gly Glu Glu Asp Ala Lys Asp Phe Thr Lys Lys Val Arg Asp
            660                 665                 670

Met Cys Val Pro Lys Leu Gly Thr Trp Pro Thr Met Met Asp Leu Ala
            675                 680                 685

Thr Thr Cys Ala Gln Met Arg Ile Phe Tyr Pro Asp Val His Asp Ala
            690                 695                 700

Glu Leu Pro Ser Leu Leu Val Asp His Asp Thr Gln Thr Cys His Val
705                 710                 715                 720

Val Asp Ser Phe Gly Ser Gln Thr Thr Gly Tyr His Ile Leu Lys Ala
                725                 730                 735

Ser Ser Val Ser Gln Leu Ile Leu Phe Ala Asn Asp Glu Leu Glu Ser
                740                 745                 750

Asp Ile Lys His Tyr Arg Val Gly Gly Val Pro Asn Ala Cys Pro Glu
                755                 760                 765

Leu Gly Ser Thr Ile Ser Pro Phe Arg Glu Gly Val Ile Met Ser
770                 775                 780

Glu Ser Ala Ala Leu Lys Leu Leu Lys Gly Ile Phe Arg Pro Lys
785                 790                 795                 800

Val Met Arg Gln Leu Leu Asp Glu Pro Tyr Leu Ile Leu Ser
                805                 810                 815

Ile Leu Ser Pro Gly Ile Leu Met Ala Met Tyr Asn Asn Gly Ile Phe
                820                 825                 830

Glu Leu Ala Val Arg Leu Trp Ile Asn Glu Lys Gln Ser Ile Ala Met
                835                 840                 845

Ile Ala Ser Leu Leu Ser Ala Leu Ala Leu Arg Val Ser Ala Ala Glu
            850                 855                 860

Thr Leu Val Ala Gln Arg Ile Ile Ile Asp Ala Ala Thr Asp Leu
865                 870                 875                 880

Leu Asp Ala Thr Cys Asp Gly Phe Asn Leu His Leu Thr Tyr Pro Thr
                885                 890                 895

Ala Leu Met Val Leu Gln Val Val Lys Asn Arg Asn Glu Cys Asp Asp
                900                 905                 910

Thr Leu Phe Lys Ala Gly Phe Pro Ser Tyr Asn Thr Ser Val Val Gln
                915                 920                 925

Ile Met Glu Lys Asn Tyr Leu Ser Leu Leu Asp Asp Ala Trp Lys Asp
            930                 935                 940

Leu Thr Trp Arg Glu Lys Leu Ser Ala Thr Trp Tyr Ser Tyr Arg Ala
945                 950                 955                 960

Lys Arg Ser Ile Thr Arg Tyr Ile Lys Pro Thr Gly Arg Ala Asp Leu
                965                 970                 975

Lys Gly Leu Tyr Asn Ile Ser Pro Gln Ala Phe Leu Gly Arg Ser Ala
                980                 985                 990

Gln Val Val Lys Gly Thr Ala Ser Gly Leu Ser Glu Arg Phe Asn Asn
                995                 1000                1005

Tyr Phe Asn Thr Lys Cys Val Asn Ile Ser Ser Phe Phe Ile Arg Arg
            1010                1015                1020

Ile Phe Arg Arg Leu Pro Thr Phe Val Thr Phe Val Asn Ser Leu Leu
1025                1030                1035                1040

Val Ile Ser Met Leu Thr Ser Val Val Ala Val Cys Gln Ala Ile Ile
                1045                1050                1055

Leu Asp Gln Arg Lys Tyr Arg Arg Glu Ile Glu Leu Met Gln Ile Glu
```

```
                    1060            1065            1070
Lys Asn Glu Ile Val Cys Met Glu Leu Tyr Ala Ser Leu Gln Arg Lys
        1075            1080            1085

Leu Glu Arg Asp Phe Thr Trp Asp Glu Tyr Ile Glu Tyr Leu Lys Ser
        1090            1095            1100

Val Asn Pro Gln Ile Val Gln Phe Ala Gln Ala Gln Met Glu Glu Tyr
1105            1110            1115            1120

Asp Val Arg His Gln Arg Ser Thr Pro Gly Val Lys Asn Leu Glu Gln
                1125            1130            1135

Glu Val Ala Phe Met Ala Leu Val Ile Met Val Phe Asp Ala Glu Arg
            1140            1145            1150

Ser Asp Cys Val Phe Lys Thr Leu Asn Lys Phe Lys Gly Val Leu Ser
        1155            1160            1165

Ser Leu Asp His Glu Val Arg His Gln Ser Leu Asp Asp Val Ile Lys
        1170            1175            1180

Asn Phe Asp Glu Arg Asn Glu Ile Ile Asp Phe Glu Leu Ser Glu Asp
1185            1190            1195            1200

Thr Ile Arg Thr Ser Ser Val Leu Asp Thr Lys Phe Ser Asp Trp Trp
                1205            1210            1215

Asp Arg Gln Ile Gln Met Gly His Thr Leu Pro His Tyr Arg Thr Glu
            1220            1225            1230

Gly His Phe Met Glu Phe Thr Arg Ala Thr Ala Val Gln Val Ala Asn
        1235            1240            1245

Asp Ile Ala His Ser Glu His Leu Asp Phe Leu Val Arg Gly Ala Val
    1250            1255            1260

Gly Ser Gly Lys Ser Thr Gly Leu Pro Val His Leu Ser Val Ala Gly
1265            1270            1275            1280

Ser Val Leu Leu Ile Glu Pro Thr Arg Pro Leu Ala Glu Asn Val Phe
            1285            1290            1295

Lys Gln Leu Ser Ser Glu Pro Phe Phe Lys Lys Pro Thr Leu Arg Met
        1300            1305            1310

Arg Gly Asn Ser Ile Phe Gly Ser Ser Pro Ile Ser Val Met Thr Ser
        1315            1320            1325

Gly Phe Ala Leu His Tyr Phe Ala Asn Asn Arg Ser Gln Leu Ala Gln
        1330            1335            1340

Phe Asn Phe Val Ile Phe Asp Glu Cys His Val Leu Asp Pro Ser Ala
1345            1350            1355            1360

Met Ala Phe Arg Ser Leu Leu Ser Val Tyr His Gln Ala Cys Lys Val
            1365            1370            1375

Leu Lys Val Ser Ala Thr Pro Val Gly Arg Glu Val Glu Phe Thr Thr
        1380            1385            1390

Gln Gln Pro Val Lys Leu Ile Val Glu Asp Thr Leu Ser Phe Gln Ser
        1395            1400            1405

Phe Val Asp Ala Gln Gly Ser Lys Thr Asn Ala Asp Val Val Gln Phe
        1410            1415            1420

Gly Ser Asn Val Leu Val Tyr Val Ser Ser Tyr Asn Glu Val Asp Thr
1425            1430            1435            1440

Leu Ala Lys Leu Leu Thr Asp Lys Asn Met Met Val Thr Lys Val Asp
                1445            1450            1455

Gly Arg Thr Met Lys His Gly Cys Leu Glu Ile Val Thr Lys Gly Thr
            1460            1465            1470

Ser Ala Arg Pro His Phe Val Val Ala Thr Asn Ile Ile Glu Asn Gly
        1475            1480            1485
```

-continued

Val Thr Leu Asp Ile Asp Val Val Asp Phe Gly Leu Lys Val Ser
    1490                1495                1500

Pro Phe Leu Asp Ile Asp Asn Arg Ser Ile Ala Tyr Asn Lys Glu Ser
1505                1510                1515                1520

Val Ser Tyr Gly Glu Arg Ile Gln Arg Leu Gly Arg Val Gly Arg Phe
        1525                1530                1535

Lys Lys Gly Val Ala Leu Arg Ile Gly His Thr Glu Lys Gly Ile Ile
        1540                1545                1550

Glu Ile Pro Ser Met Val Ala Thr Glu Ala Ala Leu Ala Cys Phe Ala
    1555                1560                1565

Tyr Asn Leu Pro Val Met Thr Gly Gly Val Ser Thr Ser Leu Ile Gly
    1570                1575                1580

Asn Cys Thr Val Arg Gln Val Lys Thr Met Gln Gln Phe Glu Leu Ser
1585                1590                1595                1600

Pro Phe Phe Ile Gln Asn Phe Val Ala His Asp Gly Ser Met His Pro
            1605                1610                1615

Val Ile His Asp Ile Leu Lys Lys Tyr Lys Leu Arg Asp Cys Met Thr
        1620                1625                1630

Pro Leu Cys Asp Gln Ser Ile Pro Tyr Arg Ala Ser Cys Thr Trp Leu
        1635                1640                1645

Ser Val Ser Glu Tyr Glu Arg Leu Gly Val Ala Leu Glu Ile Pro Lys
    1650                1655                1660

Gln Ile Lys Ile Ala Phe His Ile Lys Glu Ile Pro Pro Lys Leu His
1665                1670                1675                1680

Glu Met Leu Trp Glu Thr Val Val Lys Tyr Lys Asp Val Cys Leu Phe
            1685                1690                1695

Pro Ser Ile Arg Ala Ser Ser Ile Ser Lys Ile Ala Tyr Thr Leu Arg
        1700                1705                1710

Thr Asp Leu Phe Ala Ile Pro Arg Thr Leu Ile Leu Val Glu Arg Leu
    1715                1720                1725

Leu Glu Glu Glu Arg Val Lys Gln Ser Gln Phe Arg Ser Leu Ile Asp
        1730                1735                1740

Glu Gly Cys Ser Ser Met Phe Ser Ile Val Asn Leu Thr Asn Thr Leu
1745                1750                1755                1760

Arg Ala Arg Tyr Ala Lys Asp Tyr Thr Ala Glu Asn Ile Gln Lys Leu
            1765                1770                1775

Glu Lys Val Arg Ser Gln Leu Lys Glu Phe Ser Asn Leu Asp Gly Ser
        1780                1785                1790

Ala Cys Glu Glu Asn Leu Ile Lys Arg Tyr Gly Ser Leu Gln Phe Val
    1795                1800                1805

His His Gln Ala Ala Thr Ser Leu Ala Lys Asp Leu Lys Leu Lys Gly
    1810                1815                1820

Thr Trp Lys Lys Ser Leu Val Ala Lys Asp Leu Ile Ile Ala Gly Ala
1825                1830                1835                1840

Val Ala Ile Gly Gly Ile Gly Leu Ile Tyr Ser Trp Phe Thr Gln Ser
            1845                1850                1855

Val Glu Thr Val Ser His Gln Gly Lys Asn Lys Ser Lys Arg Ile Gln
        1860                1865                1870

Ala Leu Lys Phe Arg His Ala Arg Asp Lys Arg Ala Gly Phe Glu Ile
    1875                1880                1885

Asp Asn Asn Asp Asp Thr Ile Glu Glu Phe Phe Gly Ser Ala Tyr Arg
    1890                1895                1900

Lys Lys Gly Lys Gly Lys Gly Thr Thr Val Gly Met Gly Lys Ser Ser
1905                1910                1915                1920

-continued

Arg Lys Phe Ile Asn Met Tyr Gly Phe Asp Pro Thr Glu Tyr Ser Phe
            1925                1930                1935
Ile Gln Phe Val Asp Pro Leu Thr Gly Ala Gln Ile Glu Glu Asn Val
            1940                1945                1950
Tyr Ala Asp Ile Arg Asp Ile Gln Asp Arg Phe Ser Glu Val Arg Lys
            1955                1960                1965
Lys Met Val Glu Asn Asp Asp Ile Glu Met Gln Ala Leu Gly Ser Asn
            1970                1975                1980
Thr Thr Ile His Ala Tyr Phe Arg Lys Asp Trp Ser Asp Lys Ala Leu
1985                1990                1995                2000
Lys Ile Asp Leu Met Pro His Asn Pro Leu Lys Val Cys Asp Lys Thr
            2005                2010                2015
Asn Gly Ile Ala Lys Phe Pro Glu Arg Glu Leu Glu Leu Arg Gln Thr
            2020                2025                2030
Gly Pro Ala Val Glu Val Asn Val Lys Asp Ile Pro Ala Gln Glu Val
            2035                2040                2045
Glu His Glu Ala Lys Ser Leu Met Arg Gly Leu Arg Asp Phe Asn Pro
            2050                2055                2060
Ile Ala Gln Thr Val Cys Arg Leu Lys Val Ser Val Glu Tyr Gly Thr
2065                2070                2075                2080
Ser Glu Met Tyr Gly Phe Gly Phe Gly Ala Tyr Ile Ile Ala Asn His
            2085                2090                2095
His Leu Phe Arg Ser Tyr Asn Gly Ser Met Glu Val Gln Ser Met His
            2100                2105                2110
Gly Thr Phe Arg Val Lys Asn Leu His Ser Leu Ser Val Leu Pro Ile
            2115                2120                2125
Lys Gly Arg Asp Ile Ile Leu Ile Lys Met Pro Lys Asp Phe Pro Val
            2130                2135                2140
Phe Pro Gln Lys Leu His Phe Arg Ala Pro Ile Gln Asn Glu Arg Val
2145                2150                2155                2160
Cys Leu Val Gly Thr Asn Phe Gln Glu Lys Tyr Ala Ser Ser Ile Ile
            2165                2170                2175
Thr Glu Thr Ser Thr Thr Tyr Asn Ile Pro Gly Ser Thr Phe Trp Lys
            2180                2185                2190
His Trp Ile Glu Thr Asp Asn Gly His Cys Gly Leu Pro Val Val Ser
            2195                2200                2205
Thr Ala Asp Gly Cys Leu Val Gly Ile His Ser Leu Ala Asn Asn Ala
            2210                2215                2220
His Thr Thr Asn Tyr Tyr Ser Ala Phe Asp Glu Asp Phe Glu Ser Lys
2225                2230                2235                2240
Tyr Leu Arg Ala Asn Glu His Asn Glu Trp Val Lys Ser Trp Lys Tyr
            2245                2250                2255
Asn Pro Asp Thr Val Leu Trp Gly Pro Leu Lys Leu Lys Asp Ser Thr
            2260                2265                2270
Pro Lys Gly Leu Phe Lys Thr Thr Lys Leu Val Gln Asp Leu Ile Glu
            2275                2280                2285
His Asp Val Val Val Glu Gln Ala Lys His Ser Ala Trp Met Phe Glu
            2290                2295                2300
Ala Leu Thr Gly Asn Leu Gln Ala Val Ala Thr Met Lys Ser Gln Leu
2305                2310                2315                2320
Val Thr Lys His Val Val Lys Gly Glu Cys Arg His Phe Lys Glu Phe
            2325                2330                2335
Leu Thr Val Asp Ala Glu Ala Glu Ala Phe Phe Arg Pro Leu Met Asp

```
                    2340            2345            2350
Ala Tyr Gly Lys Ser Leu Leu Asn Arg Asp Ala Tyr Ile Lys Asp Ile
                2355            2360            2365
Met Lys Tyr Ser Lys Pro Ile Asp Val Gly Ile Val Asp Cys Asp Ala
                2370            2375            2380
Phe Glu Glu Ala Ile Asn Arg Val Ile Ile Tyr Leu Gln Val His Gly
2385            2390            2395            2400
Phe Lys Lys Cys Ala Tyr Val Thr Asp Glu Gln Glu Ile Phe Lys Ala
                2405            2410            2415
Leu Asn Met Lys Ala Ala Val Gly Ala Met Tyr Gly Gly Lys Lys Lys
                2420            2425            2430
Asp Tyr Phe Glu His Phe Thr Asp Ala Asp Lys Glu Glu Ile Val Met
                2435            2440            2445
Gln Ser Cys Leu Arg Leu Tyr Lys Gly Leu Leu Gly Ile Trp Asn Gly
                2450            2455            2460
Ser Leu Lys Ala Glu Leu Arg Cys Lys Glu Lys Ile Leu Ala Asn Lys
2465            2470            2475            2480
Thr Arg Thr Phe Thr Ala Ala Pro Leu Asp Thr Leu Leu Gly Gly Lys
                2485            2490            2495
Val Cys Val Asp Asp Phe Asn Asn Gln Phe Tyr Ser Lys Asn Ile Glu
                2500            2505            2510
Cys Cys Trp Thr Val Gly Met Thr Lys Phe Tyr Gly Gly Trp Asp Lys
                2515            2520            2525
Leu Leu Arg Arg Leu Pro Glu Asn Trp Val Tyr Cys Asp Ala Asp Gly
                2530            2535            2540
Ser Gln Phe Asp Ser Ser Leu Thr Pro Tyr Leu Phe Asn Ala Val Leu
2545            2550            2555            2560
Thr Ile Arg Ser Thr Tyr Met Glu Asp Trp Asp Val Gly Leu Gln Met
                2565            2570            2575
Leu Arg Asn Leu Tyr Thr Glu Ile Val Tyr Thr Pro Ile Ser Thr Pro
                2580            2585            2590
Asp Gly Thr Ile Val Lys Lys Phe Arg Gly Asn Asn Ser Gly Gln Pro
                2595            2600            2605
Ser Thr Val Val Asp Asn Ser Leu Met Val Val Leu Ala Met His Tyr
                2610            2615            2620
Ala Phe Ile Arg Glu Gly Ile Glu Phe Glu Glu Thr Asp Ser Thr Cys
2625            2630            2635            2640
Val Phe Phe Val Asn Gly Asp Asp Leu Leu Ile Ala Val Asn Pro Asp
                2645            2650            2655
Lys Glu Asp Ile Leu Asp Arg Leu Ser Gln His Phe Ser Asp Leu Gly
                2660            2665            2670
Leu Asn Tyr Asp Phe Ser Ser Arg Thr Arg Asn Lys Glu Glu Leu Trp
                2675            2680            2685
Phe Met Ser His Arg Gly Leu Leu Ile Glu Gly Met Tyr Val Pro Lys
                2690            2695            2700
Leu Glu Glu Glu Arg Ile Val Ser Ile Leu Gln Trp Asp Arg Ala Asp
2705            2710            2715            2720
Leu Ala Glu His Arg Leu Glu Ala Ile Cys Ala Arg Met Ile Glu Ser
                2725            2730            2735
Trp Gly Tyr Ser Glu Leu Thr His Gln Ile Arg Arg Phe Tyr Ser Trp
                2740            2745            2750
Leu Leu Gln Gln Gln Pro Phe Ala Thr Ile Ala Gln Glu Gly Lys Ala
                2755            2760            2765
```

```
Pro Tyr Ile Ala Ser Met Ala Leu Arg Lys Leu Tyr Met Asp Arg Ala
        2770                2775                2780

Val Asp Glu Glu Glu Leu Arg Ala Phe Thr Glu Met Met Val Ala Leu
2785                2790                2795                2800

Asp Asp Glu Phe Glu Phe Asp Ser Tyr Glu Val Tyr His Gln Ala Asn
            2805                2810                2815

Asp Thr Ile Asp Ala Gly Gly Ser Asn Lys Lys Asp Thr Lys Pro Glu
        2820                2825                2830

Gln Ser Ser Ile Gln Ser Asn Pro Asn Lys Gly Lys Asp Lys Asp Val
            2835                2840                2845

Asn Ala Gly Thr Ser Gly Thr His Thr Val Pro Arg Ile Lys Ala Ile
        2850                2855                2860

Thr Ser Lys Met Arg Met Pro Lys Ser Lys Gly Ala Ala Val Leu Asn
2865                2870                2875                2880

Leu Glu His Leu Leu Glu Tyr Ala Pro Gln Gln Ile Asp Ile Ser Asn
            2885                2890                2895

Thr Arg Ala Thr Gln Ser Gln Phe Asp Thr Trp Tyr Glu Ala Val Arg
        2900                2905                2910

Met Ala Tyr Asp Ile Gly Glu Thr Glu Met Pro Thr Val Met Asn Gly
        2915                2920                2925

Leu Met Val Trp Cys Ile Glu Asn Gly Thr Ser Pro Asn Val Asn Gly
        2930                2935                2940

Val Trp Val Met Met Asp Gly Asn Glu Gln Val Glu Tyr Pro Leu Lys
2945                2950                2955                2960

Pro Ile Val Glu Asn Ala Lys Pro Thr Leu Arg Gln Ile Met Ala His
        2965                2970                2975

Phe Ser Asp Val Ala Glu Ala Tyr Ile Glu Met Arg Asn Lys Lys Glu
        2980                2985                2990

Pro Tyr Met Pro Arg Tyr Gly Leu Ile Arg Asn Leu Arg Asp Met Gly
        2995                3000                3005

Leu Ala Arg Tyr Ala Phe Asp Phe Tyr Glu Val Thr Ser Arg Thr Pro
    3010                3015                3020

Val Arg Ala Arg Glu Ala Gln Ile Gln Met Lys Ala Ala Ala Leu Lys
3025                3030                3035                3040

Ser Ala Gln Pro Arg Leu Phe Gly Leu Asp Gly Gly Ile Ser Thr Gln
        3045                3050                3055

Glu Glu Asn Thr Glu Arg His Thr Thr Glu Asp Val Ser Pro Ser Met
            3060                3065                3070

His Thr Leu Leu Gly Val Lys Asn Met
        3075                3080

<210> SEQ ID NO 5
<211> LENGTH: 161
<212> TYPE: DNA
<213> ORGANISM: Potato virus
<220> FEATURE:
<223> OTHER INFORMATION: PVY-N sequence

<400> SEQUENCE: 5
cctggccaac catgatggat ctggctacaa cttgtgctca aatgaaaata ttctaccctg    60
atgttcatga tgcagaactg cctagaatac tagtcgatca cgaaacgcag acatgccatg   120
tagttgactc gtttggctca caacaactg ggtatcatat t                        161

<210> SEQ ID NO 6
<211> LENGTH: 161
<212> TYPE: DNA
```

<213> ORGANISM: Potato virus
<220> FEATURE:
<223> OTHER INFORMATION: PVYo sequence

<400> SEQUENCE: 6

```
cctggccaac tatgatggat ttggcgacca cttgtgctca aatgagaata ttctatcctg    60
acgtgcatga tgcagagctg cctagtttat tggttgacca tgacactcaa acgtgtcatg   120
tggttgactc atttggctcg cagacaactg gatatcatat t                       161
```

<210> SEQ ID NO 7
<211> LENGTH: 20
<212> TYPE: DNA
<213> ORGANISM: Artificial Sequence
<220> FEATURE:
<223> OTHER INFORMATION: PVYN (polymorphism 400) probe

<400> SEQUENCE: 7

```
ctcaaatgaa aatattctac                                                20
```

<210> SEQ ID NO 8
<211> LENGTH: 19
<212> TYPE: DNA
<213> ORGANISM: Artificial Sequence
<220> FEATURE:
<223> OTHER INFORMATION: PVYo (polymorphism 400) probe

<400> SEQUENCE: 8

```
ctcaaatgag aatattcta                                                 19
```

<210> SEQ ID NO 9
<211> LENGTH: 19
<212> TYPE: DNA
<213> ORGANISM: Artificial Sequence
<220> FEATURE:
<223> OTHER INFORMATION: PVYN (polymorphism 419) probe

<400> SEQUENCE: 9

```
cgatcacgaa acgcagaca                                                 19
```

<210> SEQ ID NO 10
<211> LENGTH: 15
<212> TYPE: DNA
<213> ORGANISM: Artificial Sequence
<220> FEATURE:
<223> OTHER INFORMATION: PVYo (polymorphism 419) probe

<400> SEQUENCE: 10

```
accatgacac tcaaa                                                     15
```

<210> SEQ ID NO 11
<211> LENGTH: 40
<212> TYPE: DNA
<213> ORGANISM: Artificial Sequence
<220> FEATURE:
<223> OTHER INFORMATION: Primer sense nucleotide 2079 to 2108 of
     PVYo-139 with NruI site

<400> SEQUENCE: 11

```
aacgtgtttc tcgcgatgct aattaacatt ggcgaggagg                          40
```

<210> SEQ ID NO 12
<211> LENGTH: 40
<212> TYPE: DNA
<213> ORGANISM: Artificial Sequence
<220> FEATURE:
<223> OTHER INFORMATION: Primer antisense nucleotide 2592 to 2561 of -continued PVYo-139 with BstZ17I site

<400> SEQUENCE: 12
agccatcagt ataccagggg ataatattga tagaatcaac          40

<210> SEQ ID NO 13
<211> LENGTH: 20
<212> TYPE: DNA
<213> ORGANISM: Artificial Sequence
<220> FEATURE:
<223> OTHER INFORMATION: Primer for reverse transcriptase

<400> SEQUENCE: 13
gtctcctgat tgaagtttac          20

<210> SEQ ID NO 14
<211> LENGTH: 163
<212> TYPE: DNA
<213> ORGANISM: Artificial Sequence
<220> FEATURE:
<223> OTHER INFORMATION: PVY-N-K400-E419

<400> SEQUENCE: 14
cctggccaac catgatggat ctggctacaa cttgtgctca aatgaaaata ttctaccctg          60
atgttcatga tgcagaactg cctagaatac tagtcgatca cgaaacgcag acatgccatg         120
tagttgactc gtttggctca caaacaactg ggtatcatat ttt          163

<210> SEQ ID NO 15
<211> LENGTH: 161
<212> TYPE: DNA
<213> ORGANISM: Artificial Sequence
<220> FEATURE:
<223> OTHER INFORMATION: PVYo-R400-D419

<400> SEQUENCE: 15
cctggccaac tatgatggat ttggcgacca cttgtgctca aatgagaata ttctatcctg          60
acgtgcatga tgcagagctg cctagttat tggttgacca tgacactcaa acgtgtcatg         120
tggttgactc atttggctcg cagacaactg gatatcatat t          161

<210> SEQ ID NO 16
<211> LENGTH: 163
<212> TYPE: DNA
<213> ORGANISM: Artificial Sequence
<220> FEATURE:
<223> OTHER INFORMATION: PVY-NTPN-K400-D419

<400> SEQUENCE: 16
cctggccaac catgatggat ctggctacaa cttgtgctca aatgaaaata ttctaccctg          60
atgttcatga tgcagaactg cctagaatac tagtcgatca cgacacgcag acatgccatg         120
tagttgactc gtttggctca caaacaactg ggtatcatat ttt          163

<210> SEQ ID NO 17
<211> LENGTH: 163
<212> TYPE: DNA
<213> ORGANISM: Artificial Sequence
<220> FEATURE:
<223> OTHER INFORMATION: PVY-NTPN-R400-E419

<400> SEQUENCE: 17
cctggccaac catgatggat ctggctacaa cttgtgctca aatgagaata ttctaccctg          60
atgttcatga tgcagaactg cctagaatac tagtcgatca cgaaacgcag acatgccatg         120
tagttgactc gtttggctca caaacaactg ggtatcatat ttt        163

<210> SEQ ID NO 18
<211> LENGTH: 161
<212> TYPE: DNA
<213> ORGANISM: Artificial Sequence
<220> FEATURE:
<223> OTHER INFORMATION: PVY-NTPo-R400-E419

<400> SEQUENCE: 18
cctggccaac tatgatggat ttggcgacca cttgtgctca aatgagaata ttctatcctg        60
acgtgcatga tgcagagctg cctagtttat tggttgacca tgaaactcaa acgtgtcatg       120
tggttgactc atttggctcg cagacaactg gatatcatat t                           161

<210> SEQ ID NO 19
<211> LENGTH: 161
<212> TYPE: DNA
<213> ORGANISM: Artificial Sequence
<220> FEATURE:
<223> OTHER INFORMATION: PVY-NTPo-K400-D429

<400> SEQUENCE: 19
cctggccaac tatgatggat ttggcgacca cttgtgctca aatgaaaata ttctatcctg        60
acgtgcatga tgcagagctg cctagtttat tggttgacca tgacactcaa acgtgtcatg       120
tggttgactc atttggctcg cagacaactg gatatcatat t                           161

<210> SEQ ID NO 20
<211> LENGTH: 17
<212> TYPE: DNA
<213> ORGANISM: Artificial Sequence
<220> FEATURE:
<223> OTHER INFORMATION: PVYN (polymorphism 419) probe

<400> SEQUENCE: 20
atcacgaaac gcagaca                                                       17

<210> SEQ ID NO 21
<211> LENGTH: 16
<212> TYPE: DNA
<213> ORGANISM: Artificial Sequence
<220> FEATURE:
<223> OTHER INFORMATION: PVYo (polymorphism 419) probe

<400> SEQUENCE: 21
tgaccatgac actcaa                                                        16

<210> SEQ ID NO 22
<211> LENGTH: 28
<212> TYPE: DNA
<213> ORGANISM: Artificial Sequence
<220> FEATURE:
<223> OTHER INFORMATION: Primer sense for YN

<400> SEQUENCE: 22
atgatgcaga actgcctaga atactagt                                           28

<210> SEQ ID NO 23
<211> LENGTH: 29
<212> TYPE: DNA
<213> ORGANISM: Artificial Sequence
<220> FEATURE:
<223> OTHER INFORMATION: Primer sense for YN

<400> SEQUENCE: 23

```
atgatgcaga actgcctaga atactagtc                                         29

<210> SEQ ID NO 24
<211> LENGTH: 27
<212> TYPE: DNA
<213> ORGANISM: Artificial Sequence
<220> FEATURE:
<223> OTHER INFORMATION: Primer sense for YN

<400> SEQUENCE: 24
catgatgcag aactgcctag aatacta                                           27

<210> SEQ ID NO 25
<211> LENGTH: 24
<212> TYPE: DNA
<213> ORGANISM: Artificial Sequence
<220> FEATURE:
<223> OTHER INFORMATION: Primer sense for YO

<400> SEQUENCE: 25
gcagagctgc ctagtttatt ggtt                                              24

<210> SEQ ID NO 26
<211> LENGTH: 25
<212> TYPE: DNA
<213> ORGANISM: Artificial Sequence
<220> FEATURE:
<223> OTHER INFORMATION: Primer sense for YO

<400> SEQUENCE: 26
atgatgcaga gctgcctagt ttatt                                             25

<210> SEQ ID NO 27
<211> LENGTH: 23
<212> TYPE: DNA
<213> ORGANISM: Artificial Sequence
<220> FEATURE:
<223> OTHER INFORMATION: Primer sense for YO

<400> SEQUENCE: 27
tgcagagctg cctagtttat tgg                                               23

<210> SEQ ID NO 28
<211> LENGTH: 24
<212> TYPE: DNA
<213> ORGANISM: Artificial Sequence
<220> FEATURE:
<223> OTHER INFORMATION: Primer antisense for YN

<400> SEQUENCE: 28
gtgagccaaa cgagtcaact acat                                              24

<210> SEQ ID NO 29
<211> LENGTH: 24
<212> TYPE: DNA
<213> ORGANISM: Artificial Sequence
<220> FEATURE:
<223> OTHER INFORMATION: Primer antisense for YN

<400> SEQUENCE: 29
tttgtgagcc aaacgagtca acta                                              24

<210> SEQ ID NO 30
<211> LENGTH: 22
<212> TYPE: DNA
<213> ORGANISM: Artificial Sequence
<220> FEATURE:
```

<223> OTHER INFORMATION: Primer antisense for YN

<400> SEQUENCE: 30
ttgtgagcca aacgagtcaa ct                                              22

<210> SEQ ID NO 31
<211> LENGTH: 22
<212> TYPE: DNA
<213> ORGANISM: Artificial Sequence
<220> FEATURE:
<223> OTHER INFORMATION: Primer antisense for YO

<400> SEQUENCE: 31
gccaaatgag tcaaccacat ga                                              22

<210> SEQ ID NO 32
<211> LENGTH: 22
<212> TYPE: DNA
<213> ORGANISM: Artificial Sequence
<220> FEATURE:
<223> OTHER INFORMATION: Primer antisense for YO

<400> SEQUENCE: 32
agccaaatga gtcaaccaca tg                                              22

<210> SEQ ID NO 33
<211> LENGTH: 23
<212> TYPE: DNA
<213> ORGANISM: Artificial Sequence
<220> FEATURE:
<223> OTHER INFORMATION: Primer antisense for YO

<400> SEQUENCE: 33
ccaaatgagt caaccacatg aca                                             23

<210> SEQ ID NO 34
<211> LENGTH: 20
<212> TYPE: DNA
<213> ORGANISM: Artificial Sequence
<220> FEATURE:
<223> OTHER INFORMATION: Sequence of primer sense Oli1

<400> SEQUENCE: 34
gacaacttgt gctcaaatga                                                 20

<210> SEQ ID NO 35
<211> LENGTH: 25
<212> TYPE: DNA
<213> ORGANISM: Artificial Sequence
<220> FEATURE:
<223> OTHER INFORMATION: Sequence of primer sense Oli2

<400> SEQUENCE: 35
ctggcgacaa cttgtgctca aatga                                           25

<210> SEQ ID NO 36
<211> LENGTH: 30
<212> TYPE: DNA
<213> ORGANISM: Artificial Sequence
<220> FEATURE:
<223> OTHER INFORMATION: Sequence of primer sense Oli3

<400> SEQUENCE: 36
tggatctggc gacaacttgt gctcaaatga                                      30

<210> SEQ ID NO 37

```
<211> LENGTH: 35
<212> TYPE: DNA
<213> ORGANISM: Artificial Sequence
<220> FEATURE:
<223> OTHER INFORMATION: Sequence of primer sense Oli4

<400> SEQUENCE: 37
catgatggat ctggcgacaa cttgtgctca aatga                          35

<210> SEQ ID NO 38
<211> LENGTH: 40
<212> TYPE: DNA
<213> ORGANISM: Artificial Sequence
<220> FEATURE:
<223> OTHER INFORMATION: Sequence of primer sense Oli5

<400> SEQUENCE: 38
ccaaccatga tggatctggc gacaacttgt gctcaaatga                     40

<210> SEQ ID NO 39
<211> LENGTH: 20
<212> TYPE: DNA
<213> ORGANISM: Artificial Sequence
<220> FEATURE:
<223> OTHER INFORMATION: Sequence of primer sense Oli6

<400> SEQUENCE: 39
gaacatcagg gtagaatatt                                           20

<210> SEQ ID NO 40
<211> LENGTH: 25
<212> TYPE: DNA
<213> ORGANISM: Artificial Sequence
<220> FEATURE:
<223> OTHER INFORMATION: Sequence of primer sense Oli7

<400> SEQUENCE: 40
atcatgaaca tcagggtaga atatt                                     25

<210> SEQ ID NO 41
<211> LENGTH: 30
<212> TYPE: DNA
<213> ORGANISM: Artificial Sequence
<220> FEATURE:
<223> OTHER INFORMATION: Sequence of primer sense Oli8

<400> SEQUENCE: 41
tctgcatcat gaacatcagg gtagaatatt                                30

<210> SEQ ID NO 42
<211> LENGTH: 35
<212> TYPE: DNA
<213> ORGANISM: Artificial Sequence
<220> FEATURE:
<223> OTHER INFORMATION: Sequence of primer sense Oli9

<400> SEQUENCE: 42
gcagttctgc atcatgaaca tcagggtaga atatt                          35

<210> SEQ ID NO 43
<211> LENGTH: 40
<212> TYPE: DNA
<213> ORGANISM: Artificial Sequence
<220> FEATURE:
<223> OTHER INFORMATION: Sequence of primer sense Oli10

<400> SEQUENCE: 43
```

```
tctaggcagt ctgcatcat gaacatcagg gtagaatatt                     40
```

<210> SEQ ID NO 44
<211> LENGTH: 24
<212> TYPE: DNA
<213> ORGANISM: Artificial Sequence
<220> FEATURE:
<223> OTHER INFORMATION: Sequence of primer sense Oli11

<400> SEQUENCE: 44

```
gcctagaata ctagtcgatc acga                                     24
```

<210> SEQ ID NO 45
<211> LENGTH: 29
<212> TYPE: DNA
<213> ORGANISM: Artificial Sequence
<220> FEATURE:
<223> OTHER INFORMATION: Sequence of primer sense Oli12

<400> SEQUENCE: 45

```
gaactgccta gaatactagt cgatcacga                                29
```

<210> SEQ ID NO 46
<211> LENGTH: 29
<212> TYPE: DNA
<213> ORGANISM: Artificial Sequence
<220> FEATURE:
<223> OTHER INFORMATION: Sequence of primer sense Oli13

<400> SEQUENCE: 46

```
gaactgccta gaatattggt tgaccatga                                29
```

<210> SEQ ID NO 47
<211> LENGTH: 34
<212> TYPE: DNA
<213> ORGANISM: Artificial Sequence
<220> FEATURE:
<223> OTHER INFORMATION: Sequence of primer sense Oli14

<400> SEQUENCE: 47

```
atgcagaact gcctagaata ctagtcgatc acga                          34
```

<210> SEQ ID NO 48
<211> LENGTH: 34
<212> TYPE: DNA
<213> ORGANISM: Artificial Sequence
<220> FEATURE:
<223> OTHER INFORMATION: Sequence of primer sense Oli15

<400> SEQUENCE: 48

```
atgcagaact gcctagaata ttggttgacc atga                          34
```

<210> SEQ ID NO 49
<211> LENGTH: 24
<212> TYPE: DNA
<213> ORGANISM: Artificial Sequence
<220> FEATURE:
<223> OTHER INFORMATION: Sequence of primer antisense Oli16

<400> SEQUENCE: 49

```
gtcgaccaca tggcatgtct gagt                                     24
```

<210> SEQ ID NO 50
<211> LENGTH: 29
<212> TYPE: DNA
<213> ORGANISM: Artificial Sequence
<220> FEATURE:

```
<223> OTHER INFORMATION: Sequence of primer antisense Oli17

<400> SEQUENCE: 50
aacgagtcga ccacatggca tgtctgagt                                              29

<210> SEQ ID NO 51
<211> LENGTH: 29
<212> TYPE: DNA
<213> ORGANISM: Artificial Sequence
<220> FEATURE:
<223> OTHER INFORMATION: Sequence of primer antisense Oli18

<400> SEQUENCE: 51
aacgagtcaa ctacatggca tgtctgcgt                                              29

<210> SEQ ID NO 52
<211> LENGTH: 34
<212> TYPE: DNA
<213> ORGANISM: Artificial Sequence
<220> FEATURE:
<223> OTHER INFORMATION: Sequence of primer antisense Oli19

<400> SEQUENCE: 52
aaccaaacga gtcgaccaca tggcatgtct gagt                                        34

<210> SEQ ID NO 53
<211> LENGTH: 34
<212> TYPE: DNA
<213> ORGANISM: Artificial Sequence
<220> FEATURE:
<223> OTHER INFORMATION: Sequence of primer antisense Oli20

<400> SEQUENCE: 53
agccaaacga gtcaactaca tggcatgtct gcgt                                        34
```